(12) United States Patent
Nakano et al.

(10) Patent No.: US 8,218,138 B2
(45) Date of Patent: *Jul. 10, 2012

(54) APPARATUS AND METHOD FOR INSPECTING DEFECTS

(75) Inventors: Hiroyuki Nakano, Chigasaki (JP); Akira Hamamatsu, Yokohama (JP); Sachio Uto, Yokohama (JP); Yoshimasa Oshima, Yokohama (JP); Hidetoshi Nishiyama, Hitachinaka (JP); Yuta Urano, Yokohama (JP); Shunji Maeda, Yokohama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/172,233

(22) Filed: Jun. 29, 2011

(65) Prior Publication Data

US 2011/0255074 A1    Oct. 20, 2011

Related U.S. Application Data

(63) Continuation of application No. 12/950,243, filed on Nov. 19, 2010, now Pat. No. 7,973,920, which is a continuation of application No. 12/827,470, filed on Jun. 30, 2010, now abandoned, which is a continuation of application No. 12/328,357, filed on Dec. 4, 2008, now Pat. No. 7,768,635, which is a continuation of application No. 12/029,660, filed on Feb. 12, 2008, now abandoned, which is a continuation of application No. 11/653,322, filed on Jan. 16, 2007, now Pat. No. 7,333,192.

(30) Foreign Application Priority Data

Jan. 23, 2006    (JP) .................................. 2006-013285

(51) Int. Cl.
*G01N 21/00* (2006.01)
*G01N 21/88* (2006.01)

(52) U.S. Cl. ................ 356/237.2; 356/237.1; 356/237.3; 356/237.4; 356/237.5

(58) Field of Classification Search .... 356/237.1–237.5; 250/492.1, 492.2, 559.42; 438/14, 16

See application file for complete search history.

(56) References Cited

U.S. PATENT DOCUMENTS 4,423,331 A    12/1983    Koizumi et al.
(Continued)

FOREIGN PATENT DOCUMENTS

JP    61-169815    7/1986
(Continued)

*Primary Examiner* — Sang Nguyen
(74) *Attorney, Agent, or Firm* — Antonelli, Terry, Stout & Kraus, LLP.

(57) ABSTRACT

A defect inspection apparatus and method includes utilizing an irradiation optical system that focuses a beam flux emitted from a laser light source and formed into a slit-shaped beam so as to irradiate the beam onto the surface of the substrate to be inspected, utilizing a detection optical system that detects light from the substrate that has been irradiated with the slit-shaped beam, and utilizing a signal processor that processes a signal output from the detection optical system. The irradiation optical system includes a cylindrical lens for focusing the beam that has been emitted from the laser light source onto the substrate to be inspected, as the slit-shaped beam, wherein the cylindrical lens is disposed so as to obtain a distance between an incidence surface or emitting surface thereof and the slit-shaped beam upon the substrate to be inspected to be equal to a focal distance of the cylindrical lens.

11 Claims, 42 Drawing Sheets

U.S. PATENT DOCUMENTS

| | | | |
|---|---|---|---|
| 4,508,453 A | 4/1985 | Hara et al. |
| 4,521,075 A | 6/1985 | Obenschain et al. |
| 4,619,508 A | 10/1986 | Shibuya |
| 5,029,975 A | 7/1991 | Pease |
| 5,120,126 A | 6/1992 | Wertz |
| 5,161,139 A | 11/1992 | Inoue |
| 5,359,407 A | 10/1994 | Suzuki et al. |
| 5,528,360 A | 6/1996 | Kohno |
| 5,975,701 A | 11/1999 | Takagi et al. |
| 6,031,607 A | 2/2000 | Miyazaki |
| 6,072,631 A | 6/2000 | Guenther |
| 6,084,664 A | 7/2000 | Matsumoto |
| 6,091,488 A | 7/2000 | Bishop |
| 6,107,637 A | 8/2000 | Watanabe |
| 6,169,634 B1 | 1/2001 | Sirat |
| 6,262,845 B1 | 7/2001 | Sweatt |
| 6,288,780 B1 | 9/2001 | Fairley |
| 6,366,352 B1 | 4/2002 | Goldberg et al. |
| 6,369,888 B1 | 4/2002 | Karpol |
| 6,400,454 B1 | 6/2002 | Noguchi |
| 6,411,377 B1 | 6/2002 | Noguchi et al. |
| 6,479,832 B1 | 11/2002 | Naraki et al. |
| 6,556,290 B2 | 4/2003 | Maeda et al. |
| 6,608,676 B1 | 8/2003 | Zhao et al. |
| 6,621,571 B1 | 9/2003 | Maeda et al. |
| 6,700,658 B2 | 3/2004 | Leonard |
| 6,774,991 B1 | 8/2004 | Danko |
| 6,800,859 B1 | 10/2004 | Shishido et al. |
| 6,895,149 B1 | 5/2005 | Jacob |
| 6,924,891 B2 | 8/2005 | Karpol et al. |
| 6,927,847 B2 | 8/2005 | Yoshida et al. |
| 7,098,055 B2 | 8/2006 | Noguchi et al. |
| 7,205,549 B2 | 4/2007 | Yoshida et al. |
| 7,248,354 B2 | 7/2007 | Kreh et al. |
| 7,333,192 B2 | 2/2008 | Nakano et al. |
| 7,465,935 B2 | 12/2008 | Urano et al. |
| 7,768,635 B2 | 8/2010 | Nakano et al. |
| 2002/0030807 A1 | 3/2002 | Maeda |
| 2002/0168787 A1* | 11/2002 | Noguchi et al. ............ 438/16 |
| 2003/0048439 A1 | 3/2003 | Yoshida |
| 2003/0197858 A1 | 10/2003 | Karpol |
| 2004/0124363 A1 | 7/2004 | Yoshida et al. |
| 2005/0219518 A1 | 10/2005 | Korngut |
| 2005/0264797 A1 | 12/2005 | Nakano et al. |
| 2006/0124874 A1 | 6/2006 | Uto et al. |

FOREIGN PATENT DOCUMENTS

| | | |
|---|---|---|
| JP | 01-117024 | 5/1989 |
| JP | 02-276027 | 11/1990 |
| JP | 06-167640 | 6/1994 |
| JP | 06-249789 | 9/1994 |
| JP | 06-258239 | 9/1994 |
| JP | 08-210989 | 8/1996 |
| JP | 11-030590 | 2/1999 |
| JP | 2000-105203 | 4/2000 |
| JP | 2000-121836 | 4/2000 |
| JP | 2000-162141 | 6/2000 |
| JP | 2000-223541 | 8/2000 |
| JP | 2000-315712 | 11/2000 |
| JP | 2003-311926 | 11/2000 |
| JP | 2001-060607 | 3/2001 |
| JP | 2001-194323 | 7/2001 |
| JP | 2001-250852 | 9/2001 |
| JP | 2001-264264 | 9/2001 |
| JP | 2002-257533 | 9/2002 |
| JP | 2002-261139 | 9/2002 |
| JP | 2003-035680 | 2/2003 |
| JP | 2003-167213 | 6/2003 |
| JP | 2003-177102 | 6/2003 |
| JP | 2003-197699 | 7/2003 |
| JP | 2003-329610 | 11/2003 |
| JP | 2004-039252 | 3/2004 |
| JP | 2004-177284 | 6/2004 |
| JP | 2004-177377 | 6/2004 |
| JP | 2004-184142 | 7/2004 |
| JP | 2004-301847 | 10/2004 |
| JP | 2005-156537 | 6/2005 |
| JP | 2005-283190 | 10/2005 |
| JP | 2005-300553 | 10/2005 |
| JP | 2005-337851 | 12/2005 |
| JP | 2006-029881 | 2/2006 |
| JP | 2006-119142 | 5/2006 |
| JP | 2006-132947 | 5/2006 |
| JP | 2006-201044 | 8/2006 |

* cited by examiner

FIG. 11A
FIG. 11B
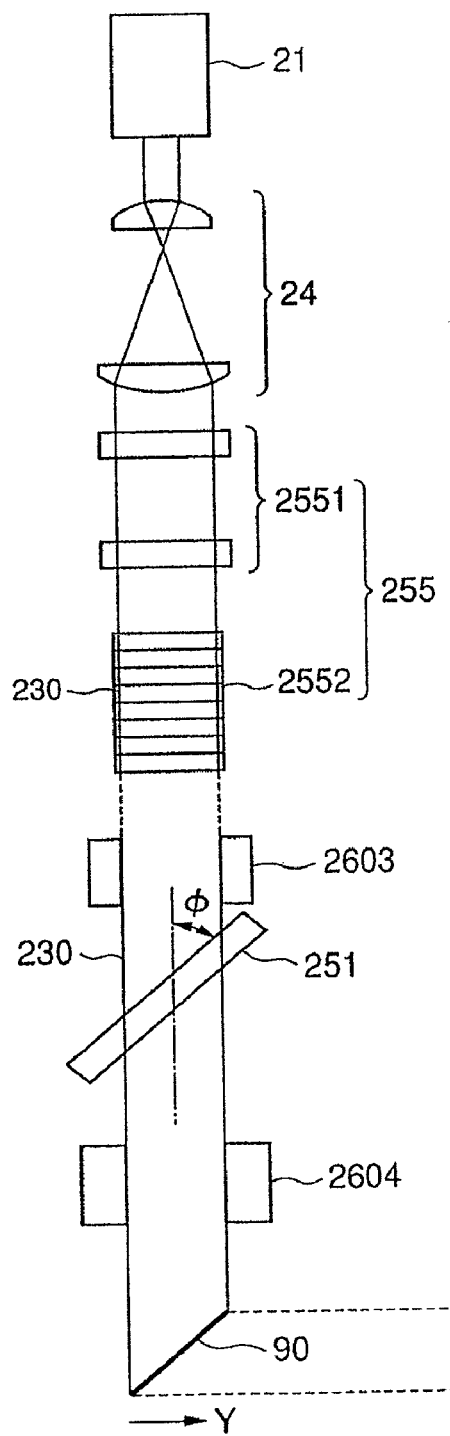
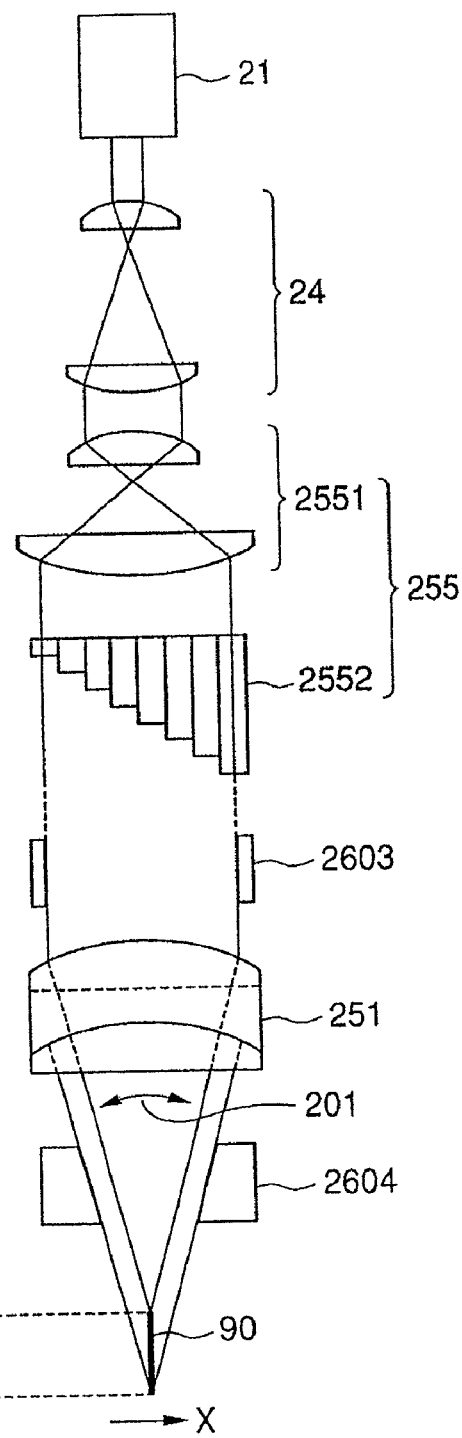

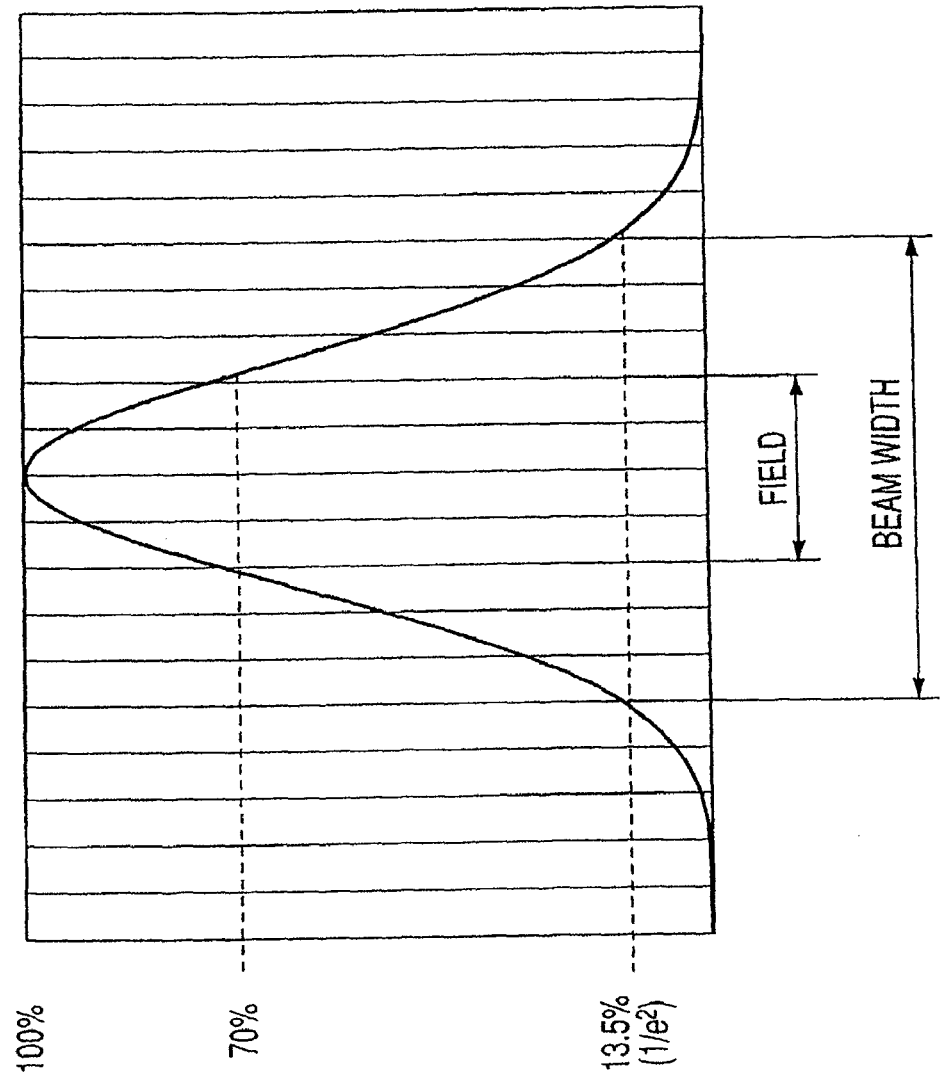

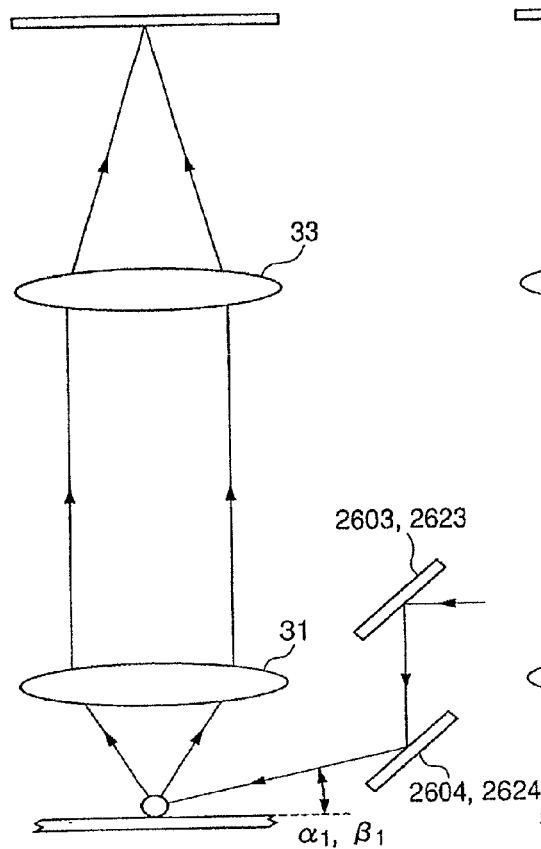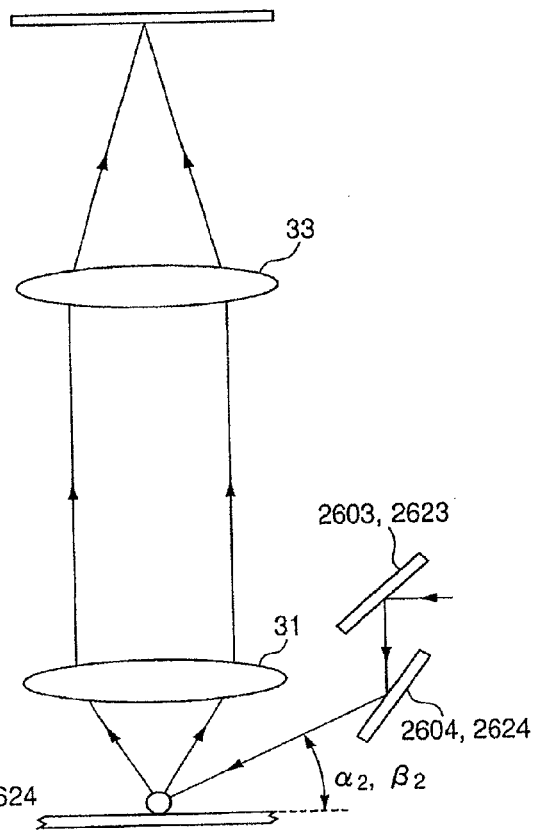

FIG. 21A
CHIP LAYOUT
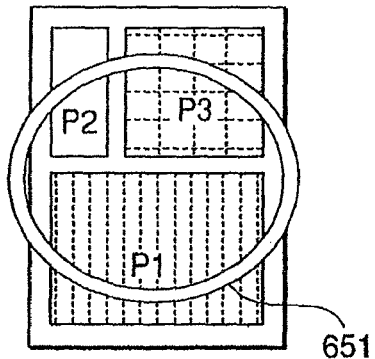
651
FIG. 21B
| PATTERN ON WAFER | P1 | P2 | P3 |
|---|---|---|---|
| DIFFRACTED LIGHT PATTERN | FP1 | FP2 | FP3 |
FIG. 21C
LOGICAL SUM OF THE FOURIER TRANSFORM
IMAGES FP1, FP2, AND FP3 OBSERVED
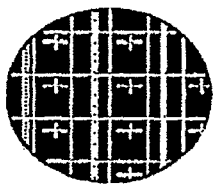

|  |  | PROCESSING IN 1×1 PIXEL FORMAT | |
|---|---|---|---|
|  |  | DETECTED | UNDETECTED |
| PROCESSING IN 5×5 PIXEL FORMAT | DETECTED | LARGE CONTAMINATION | CONTAMINATION SMALL IN HEIGHT |
|  | UNDETECTED | MICROCONTAMINATION | — |

APPARATUS AND METHOD FOR INSPECTING DEFECTS

CROSS REFERENCE TO RELATED APPLICATIONS

This application is a continuation application of U.S. application Ser. No. 12/950,243, filed Nov. 19, 2010, now U.S. Pat. No. 7,973,920, which is a continuation application of U.S. application Ser. No. 12/827,470, filed Jun. 30, 2010, now abandoned, which is a continuation of U.S. application Ser. No. 12/328,357, filed Dec. 4, 2008, now U.S. Pat. No. 7,768,635, which is a continuation of U.S. application Ser. No. 12/029,660, filed Feb. 12, 2008, now abandoned, which is a continuation application of U.S. application Ser. No. 11/653,322, filed Jan. 16, 2007, now U.S. Pat. No. 7,333,192, which claims the benefit of Japanese Application No. JP 2006-013285, filed Jan. 23, 2006 in the Japanese Patent Office, the disclosures of which are incorporated herein by reference.

BACKGROUND OF THE INVENTION

The present invention relates to an apparatus and method for inspecting defects, adapted to detect and analyze contamination and other defects occurring during the manufacturing processes of a desired object that include forming patterns on a substrate, to provide appropriate measures against contamination and other defects, and to inspect the occurrence status thereof. The manufacturing processes include semiconductor manufacturing processes, liquid-crystal display device manufacturing processes, printed-circuit board manufacturing processes, and the like.

During conventional semiconductor-manufacturing processes, the presence of dust particles or other foreign substances (hereinafter, referred to collectively as contamination) on the surface of a semiconductor substrate (wafer) causes defects such as the improper insulation or short-circuiting of wiring. In addition, if a semiconductor device becomes fine-structured to form fine-structured contamination in the semiconductor substrate, the formation of the contamination results in the improper insulation of capacitors and/or in damage to gate oxide films or the like. Such contamination gets entrapped in various forms for various reasons. For example, the contamination may have stemmed from the movable section of a transport device, from the human body, or from an internal reaction product of a processing device due to a process gas, or may have been included in a chemical or a material. The occurrence of contamination or some other defect on patterns during liquid-crystal display device manufacturing processes similar to the above manufacturing processes renders the display device inoperative. The same situation also arises during printed-circuit board manufacturing processes; the presence of contamination causes pattern short-circuiting and/or improper connection.

A known technique for inspecting the above-mentioned contamination is by irradiating a wafer with coherent light, spatially filtering away the light exited from an iterative pattern present on the wafer, and detecting non-repeatable contamination or other defects in edge-enhanced form. Also, Japanese Laid-Open Patent Application Publication (JP Kokai) No. Hei 01-117024 (Patent Document 1) discloses a contamination inspection apparatus constructed such that a circuit pattern formed on a wafer is irradiated from a direction inclined at 45 degrees to a major straight-line group of the circuit pattern to prevent the zeroth-order diffracted light from the major straight-line group from being input to an aperture of an objective lens. It is also described that in the conventional technique of Patent Document 1, straight lines not belonging to the main straight-line group are light-shielded with a spatial filter. In addition, other known apparatuses and methods for inspecting contamination and other defects are described in JP Kokai Nos. Hei 06-258239 (Patent Document 2), Hei 08-210989 (Patent Document 3), 2000-105203 (Patent Document 4), 2004-93252 (Patent Document 5), 2004-177284 (Patent Document 6), and 2004-184142 (Patent Document 7). That is to say, Patent Documents 2 and 7 describe a technique using a pitch-variable spatial filter. Patent Document 3 describes a technique in which, after a plurality of light fluxes spatially incoherent with each other have been obtained by splitting a beam emitted from a laser source and combining mirrors for the fluxes to differ from one another in optical path length, a desired section on a substrate is irradiated with the obtained plurality of fluxes obliquely at mutually different angles of incidence and then the reflected/scattered light arising from very small defects on the substrate during the irradiation is converged via detection optics and received with photoelectric conversion means. Patent Document 7 further describes a technique using various forms of spatial filters, inclusive of a transmissive type of liquid-crystal filter. Patent Documents 4, 5, and 6 describe an apparatus for inspecting defects such as contamination, equipped with highly efficient illumination optics to emit a slit-shaped beam of illumination light from a direction of 45 degrees for reduced incidence of pattern-scattered light on an objective lens.

SUMMARY OF THE INVENTION

In Patent Documents 1-7 outlined above, however, sufficient consideration has not been paid to a design capable of inspecting very small particle-like contamination, thin-film-like contamination, scratches, and other defects present on various types of substrates that is to be inspected, in a simple configuration. The various types of substrates includes substrates having various regions (such as a region with the rough edges of an ultrafine-structured circuit pattern, a region with an iterative pattern and a non-iterative pattern in mixed form, a region different in pattern density from other regions, and a region with a transparent film).

In order to solve the above problem, the present invention provides an apparatus and method for inspecting defects, constructed such that very small particle-like contamination, thin-film-like contamination, scratches, and other defects present on various types of substrates to be inspected can be inspected in a simple apparatus configuration at high speed and with high accuracy. The various types of substrates include substrates with various regions.

The present invention also provides an apparatus and method for inspecting defects, adapted such that a highly efficient manufacturing line for substrates can be constructed by using the apparatus as an in-line monitor.

An aspect of the present invention is an apparatus and a method for inspecting defects, the apparatus including: a stage that moves with a substrate (to be inspected) being rested thereon, the substrate including a circuit pattern formed thereon; an irradiation optical system that guides a flux of beams emitted from a laser light source, from a principal optical path to a first or second optical path, then focuses the beam flux that has been guided to the first or second optical path into a slit-shaped beam formed of fluxes of light that are substantially parallel in a longitudinal direction of the slit-shaped beam, from a direction having a required inclination extending horizontally with respect to a major straight-line group of the circuit pattern and at a required angle of inclination to the surface of the substrate, and irradiates the substrate with the slit-shaped beam such that the longitudinal direction is at a substantially right angle to a traveling direction of the stage; a detection optical system that uses an objective lens to converge reflected/scattered light obtained from contamination or defects present on the substrate that has been irradiated with the slit-shaped beam, and uses an image sensor to receive the reflected/scattered light that has been converged, convert the received light into a signal, and detect the signal; and an image processor which, on the basis of the signal that has been detected by the image sensor of the detection optical system, extracts a signal indicative of the defect such as contamination. The irradiation optical system in the above apparatus and method for inspecting defects includes a mirror that reflects and directs downward the beam flux that was guided to the first or second optical path, and a cylindrical lens and inclined mirror for focusing the beam flux that has been directed downward by the foregoing mirror onto the substrate, from the direction having the required inclination extending horizontally and at the required inclination angle, and thus obtaining the slit-shaped beam.

Also, the inclined mirror in the above irradiation optical system is constructed to make the slit-shaped beam selectively usable for irradiation at both a high angle of inclination and a low angle of inclination.

Another aspect of the present invention is an apparatus and method for inspecting defects, the apparatus including: a stage which is caused to travel after a substrate to be inspected has been rested on the stage, the substrate including a circuit pattern formed thereon; an irradiation optical system which, after emitting a flux of beams from a laser light source, guides the beam flux from a principal optical path to a first optical path, a second optical path, and a third optical path each, then focuses the beam flux that has been guided as a first beam flux to the first optical path into a first slit-shaped beam, from a clockwise direction having a required inclination extending horizontally with respect to an X-axis direction of a major straight-line group of the circuit pattern and at a required angle of inclination to the surface of the substrate to be inspected, the first slit-shaped beam being formed of fluxes substantially parallel in a longitudinal direction, and irradiates the substrate with the first slit-shaped beam such that the longitudinal direction is substantially at right angles to a traveling direction of the stage, focuses the beam flux that has been guided as a second beam flux to the second optical path into a second slit-shaped beam from a counterclockwise direction having a required inclination extending horizontally with respect to the X-axis direction and at a required angle of inclination to the surface of the substrate to be inspected, the second slit-shaped beam being formed up by fluxes substantially parallel in a longitudinal direction, and irradiates the substrate with the second slit-shaped beam such that the longitudinal direction is at a substantially right angle to the traveling direction of the stage, and focuses the beam flux that has been guided as a third beam flux to the third optical path into a third slit-shaped beam, from the X-axis direction extending horizontally and at a required angle of inclination to the surface of the substrate, the third slit-shaped beam being formed of fluxes substantially parallel in a longitudinal direction, and irradiates the substrate with the third slit-shaped beam such that the longitudinal direction is at a substantially right angle to the traveling direction of the stage; a detection optical system which uses an objective lens to converge reflected/scattered light obtained from contamination or some other defect present on the substrate that has been irradiated with the slit-shaped beam, the detection optical system further using an image sensor to receive the reflected/scattered light that has been converged, convert the received light into a signal, and detect the signal; and an image processor which, on the basis of the signal that has been detected by the image sensor of the detection optical system, extracts a signal indicative of the defect such as contamination.

The irradiation optical system in the above apparatus and method for inspecting defects includes: a first mirror which reflects and directs downward the first beam flux that has been guided to the first optical path; a first cylindrical lens and a first inclined mirror for focusing the beam flux that has been directed downward by the first mirror onto the substrate, from a clockwise direction having the required inclination extending horizontally and at the required inclination angle, and thus obtaining the first slit-shaped beam; a second mirror which reflects and directs downward the second beam flux that has been guided to the second optical path; a second cylindrical lens and a second inclined mirror for focusing the beam flux that has been directed downward by the second mirror onto the substrate, from the counterclockwise direction having the required inclination extending horizontally and at the required inclination angle, and thus obtaining the second slit-shaped beam; a third mirror which reflects and directs downward the third beam flux that was guided to the third optical path; and a third cylindrical lens and a third inclined mirror for focusing the beam flux that has been directed downward by the third mirror onto the substrate, from the X-axis direction extending horizontally and at the required inclination angle, and thus obtaining the third slit-shaped beam.

Also, the irradiation optical system in the above apparatus and method for inspecting defects is constructed such that principal-beam expanding optics for expanding beams in diameter is disposed in the principal optical path and such that beam-expanding optics for expanding the third beam flux further in diameter and matching the first, second, and third slit-shaped beams in longitudinal length on the substrate is disposed in the third optical path.

In addition, the irradiation optical system in the above apparatus and method for inspecting defects is constructed such that an optical member group formed by stacking a plurality of plate-shaped optical members each having a different optical path length in at least a light-converging direction of the second cylindrical lens is disposed on the first, second, or third optical path to receive a coherent second beam flux obtained from the principal optical path, and emit a plurality of slit-shaped beams each spatially reduced in coherency, in the light-converging direction of at least the second cylindrical lens.

Furthermore, the irradiation optical system in the above apparatus and method for inspecting defects is constructed such that beam-expanding optics for expanding the incident beam flux in diameter in at least a stacking direction of the plurality of plate-shaped optical members is disposed at an incident side of the optical member group.

Further, the irradiation optical system in the above apparatus and method for inspecting defects is constructed such that an optical member group formed by stacking a plurality of plate-shaped optical members each having a different optical path length in at least a light-converging direction of a cylindrical lens provided on at least a selected path is disposed on the principal optical path so as to be movable in and out with respect thereto for receiving a coherent beam flux obtained from the laser light source, and emit a plurality of slit-shaped beams each spatially reduced in coherency, in the light-converging direction of the cylindrical lens.

Furthermore, the first, second, and third inclined mirrors in the above irradiation optical system are constructed so as to allow the slit-shaped beams to be switched for irradiation at a high angle of inclination and irradiation at a low angle of inclination.

Furthermore, the detection optical system in the above apparatus and method for inspecting defects is constructed such that a spatial filter for light-shielding an interference pattern formed from an iterative circuit pattern present on the substrate is disposed at a position conjugate to a pupil of the objective lens.

Further, the irradiation optical system in the above apparatus and method for inspecting defects is constructed such that a luminous quantity adjusting filter for adjusting the amount of light is disposed on the principal optical path. The irradiation optical system in the above apparatus and method for inspecting defects is further constructed such that a polarizing plate for conducting polarization control is disposed on the principal optical path, and the detection optical system is constructed to include an analyzer that controls and detects polarization.

Moreover, the laser light source in the above apparatus and method for inspecting defects is constructed to emit UV or DUV laser light. The above apparatus and method for inspecting defects is further constructed to make a magnification of detected image formation variable in the detection optical system.

These and other objects, features and advantages of the invention will be apparent from the following more particular description of preferred embodiments of the invention, as illustrated in the accompanying drawings.

BRIEF DESCRIPTION OF THE DRAWINGS

FIGS. 11A and 11B are diagrams illustrating an example of a section which consists of, in the present invention, coherency reduction optics and φ-angled irradiation optics including a cylindrical lens and a mirror and adapted for slit-shaped beam irradiation, the two kinds of optics being shown in a form developed in an optical-axis direction;

FIG. 14 is a diagram representing a relationship between a field of view and a Gaussian intensity distribution of the laser beam flux emitted from a laser light source according to the present invention;

FIGS. 15A and 15B are diagrams that show irradiations with a slit-shaped beam at a low angle and a high angle with an inclined mirror in the φ-angled irradiation optics and X-axial irradiation optics of the present invention, respectively, the angle being capable of being switched by switching the angle of the inclined mirror;

FIGS. 21A to 21C are diagrams that show chip layout based on the present invention, the Fourier transform images observed, and a logical sum thereof, respectively;

DESCRIPTION OF THE PREFERRED EMBODIMENTS

Figure 1:
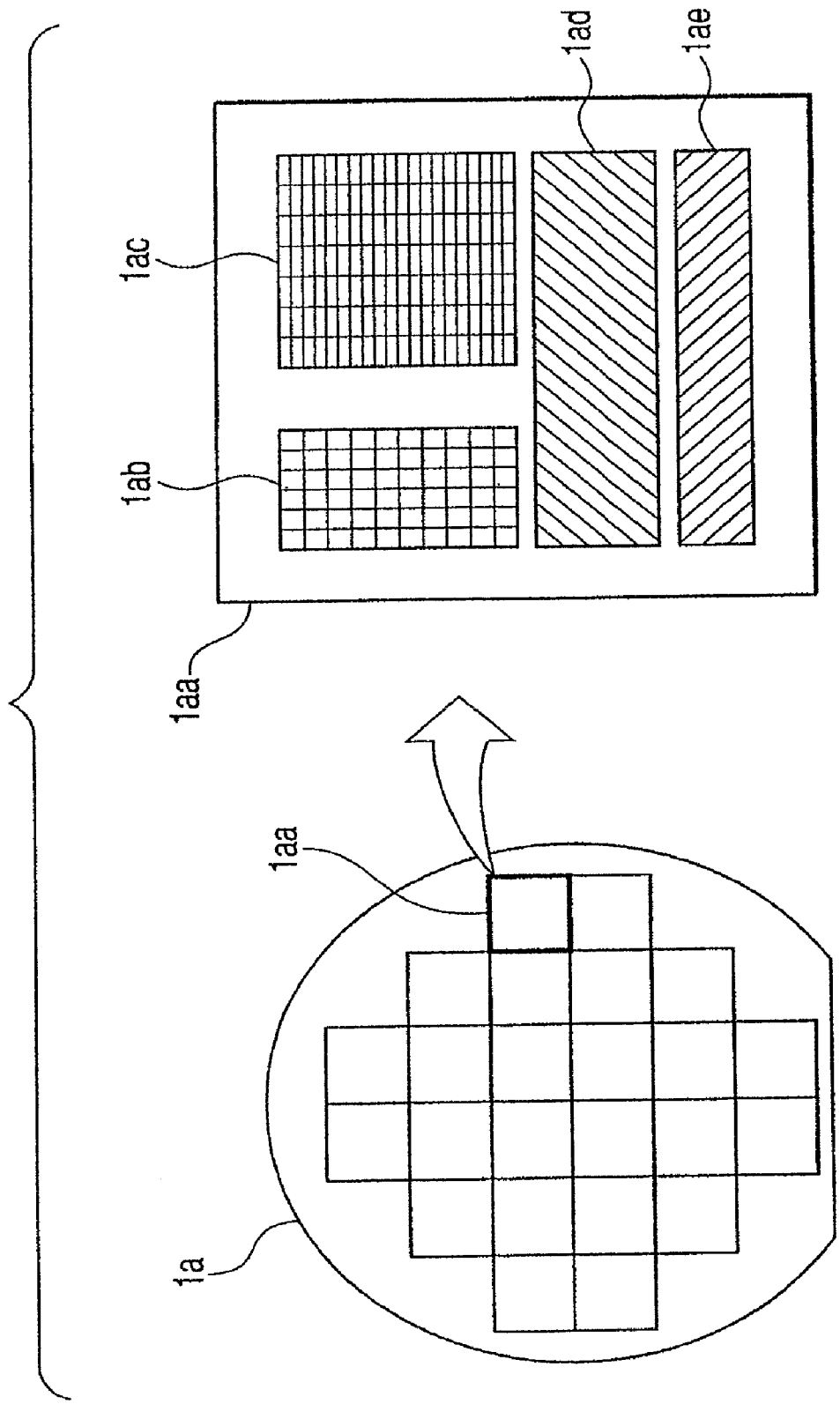
FIG. 1 is a diagram showing an example of a semiconductor wafer which is a substrate to be inspected according to the present invention.

Hereunder, embodiments of the present invention will be described using the accompanying drawings.

One possible kind of object 1 to be subjected to inspection of defects such as contamination, is a semiconductor wafer "1a" with chips "1aa" arrayed two-dimensionally at required spatial intervals (hereinafter, the object 1 is referred to as the inspection target 1). An interior of each chip "1aa" is mainly formed up by a register group region "1ab", a memory region "1ac", a CPU core region "1ad", and an input/output region "1ae". The register group region "1ab" and the memory region "1ac" are both formed by two-dimensionally and regularly arranging patterns with a minimum line width ranging from about 0.05 to 0.02 μm. The CPU core region "1ad" and the input/output region "1ae" are both formed by non-iteration of patterns with a minimum line width ranging from about 0.05 to 0.02 μm. In this way, even when the inspection target 1 for the inspection of contamination and other defects is a semiconductor wafer and chips are regularly arrayed thereon, the inspection target 1 may take various forms; the interior of each chip varies from region to region in terms of minimum line width, patterns are created in iterative or non-iterative form, and/or transparent thin films are formed.

Embodiments of the present invention relating to an apparatus and method for inspecting defects such as contamination are adapted to allow highly-sensitive and high-speed inspection of very small defects ranging from 0.05 μm to 0.10 μm in size, such as contamination, scratches, and pattern defects, that are present on the inspection target 1 which takes various forms as mentioned above. In the above defect inspection apparatus and method, defects can also be classified according to the type thereof.

A first embodiment of an apparatus for inspecting contamination and other defects according to the present invention is described below using FIG. 2. While the embodiment described below relates to inspecting defects such as small/large contamination, pattern defects, and microscratches on a semiconductor wafer, the present invention is not limited to semiconductor wafers and can also be applied to thin-film substrates, thin-film transistors (TFTs), plasma display panels (PDPs), and more.

The first embodiment of an apparatus for inspecting defects such as contamination includes a transport system (stage system) 10, an irradiation optical system 20, a detection optical system 30, an image processor 40, an observation optical system 50, an in-focus control system 60, a total controller 70, and a reviewing optical microscope 80. The transport system (stage system) 10 includes an X-stage 11, Y-stage 12, and Z-stage 13, each for resting thereon and moving the inspection target substrates 1, such as wafers, that are obtained from various product types and various manufacturing process steps. The transport system (stage system) 10 also includes a e-stage 14 (rotary stage in a horizontal plane) and a stage controller 15.

The irradiation optical system 20 includes a laser light source 21, a luminous quantity adjusting filter (luminous attenuation filter) 22 for adjusting the amount of light, a polarizing plate 23 for converting the light into, for example, linearly polarized P- or S-components, principal-beam expanding optics 24 for expanding a beam flux to a certain diameter, and light-converging optics 25 that uses a mirror group 26 and/or other optical members to converge the beam flux upon the substrate 1 in the form of a slit-shaped beam elongated in a direction perpendicular to a traveling direction of the substrate. The irradiation optical system 20 further includes an illumination controller 27 that controls or selects an illumination angle and a filter type under the commands sent from the total controller 70. In consideration of highly sensitive inspection of contamination and other defects and of minimum maintenance costs, a second-harmonic generation (SHG) type of high-output YAG laser with a 532-nm wavelength is preferably used as the laser light source 1. However, the laser light source does not always need to provide 532 nm in wavelength and may emit an ultraviolet (UV) laser, a far-ultraviolet (FUV) or deep-ultraviolet (DUV) laser, a vacuum UV laser, an argon (Ar) laser, a nitrogen laser, a helium-cadmium (He—Cd) laser, an excimer laser, a semiconductor laser, or the like. An advantage obtained from using any of these laser light sources is that since shortening the laser wavelength enhances resolution of the images detected, defects can be inspected with higher sensitivity. For a short wavelength of about 0.34 µm, an objective lens 31 preferably has a numerical aperture (NA) of about 0.4, or for a wavelength of about 0.17 µm, an NA of about 0.2. Thus, a large amount of diffracted light from a defect such as contamination can be made to enter the objective lens 31 for improved detection sensitivity.

Figure 18:
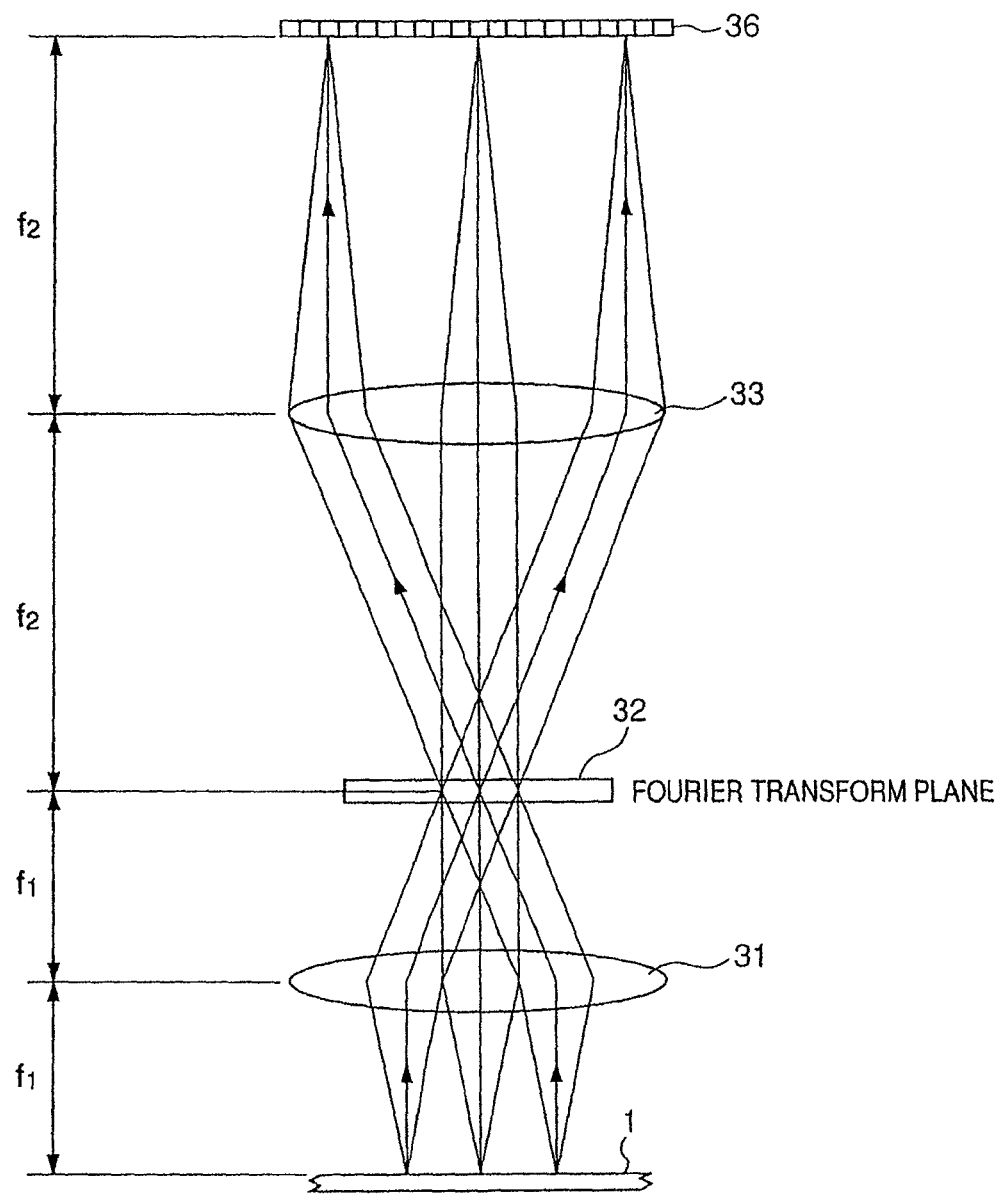
FIG. 18 is a diagram showing an example of a detection optical system according to the present invention.

The detection optical system 30 includes, as shown in FIG. 18, the objective lens 31, a spatial filter 32 provided at a position conjugate to a pupil of the objective lens 31, imaging optics 33, an optical filter group 34 constituted by, for example, an ND (Neutral Density) filter and an analyzer (polarizing filter), and a photodetector (image sensor) 36 such as a TDI (Time Delay Integration) image sensor. Sensitivity can be increased by using a TDI image sensor as the image sensor 36.

The image processor 40 includes: an A/D converter 41 for A/D conversion of an image signal detected by the photodetector 36; a data storage unit 42 for storing the detected image signal "f(i, j)" that has been obtained by the ND conversion; a threshold calculation processor 43 for calculating threshold levels based on the detected image signal; a contamination detection processor 44 for conducting contamination detection processing for each pixel-merging operation, based on the detected image signal obtained from the data storage unit 42 and on the threshold image signal obtained from the threshold calculation processor 43; a feature calculating circuit 45 for calculating features for each merging operation, such as the amount of scattered light that has been obtained from defect detection, and the quantity (area, projection length, or like value) of detected pixels, indicating a spread of the defect; and an integrated processor 46 that classifies on-wafer small/large contamination, pattern defects, microscratches, and other defects into various types of defects on the basis of the features obtained from the feature calculating circuit 45 for each merging operation. Inspection results obtained by the integrated processor 46 are then supplied to the total controller 70 for display in a GUI screen of a display unit 72.

The observing optical system 50 includes a mirror 51 disposed on a detection optical path so as to be movable in and out with respect thereto, as indicated by arrows; an optical branching element 52 such as a half-mirror; observation optics 53 for observing a light-shielding pattern of a spatial filter 32 provided on a Fourier transform plane; and observation optics 54 for observing an image of the wafer surface. The observation optics 53 includes an image-forming lens 531 and an image sensor 532 such as a TV camera. The observation optics 54 also includes an imaging lens 541 and an image sensor 542 such as a TV camera.

The in-focus control system 60 includes: a light source 61 such as a lamp; a striped pattern (grid-shaped pattern) 62 to be projected onto the surface of the wafer by using parallel light fluxes that are emitted from the light source 61; a half-mirror 63; a projection lens 64 for projecting the striped pattern onto the wafer surface; an imaging lens 65 for forming an image of the striped pattern regularly reflected from the wafer surface; a mirror 66 for reflecting the striped pattern formed by the imaging lens 65; an imaging lens 67 that forms an striped pattern obtained through the projection lens 64 and the half-mirror 63 after the striped pattern formed by the imaging lens 65 is reflected by the mirror 66 and returned to parallel light fluxes by the imaging lens 65 to being regularly reflected on the wafer surface; a one-dimensional or two-dimensional linear image sensor 68 for detecting, as a positional shift of the striped pattern, an out-of-focus state on the wafer surface; and an in-focus controller 69 for controlling, for example, the Z-stage 13 according to the out-of-focus state detected by the linear image sensor, and conducting an in-focus matching process on the surface of the wafer.

The total controller 70 includes: an input device 71 (including a keyboard, a mouse, a network interface, and so on) for entering information on the various wafers loaded; the display unit 72 that has modes such as a GUI screen mode for displaying the image acquired by the image sensor 36, the screen image observed through the observation optics 53, 54, and images of the contamination and other defects reviewed through the reviewing optical microscope 80, and displays the threshold level information calculated by the threshold calculation processor 43 or the like, and the inspection results and other data obtained in the integrated processor 46; and a data storage unit 73 for storing various information such as CAD information of the wafers, inspection parameter information on past wafers, and the inspection result information obtained in the integrated processor 46.

The reviewing optical microscope 80 includes a light source 81 for emitting visible light such as white light, a half-mirror 82, an objective lens 83, an imaging lens 84, and an image sensor 85. The microscope 80 acquires images of defects or false defects or the like and supplies the images to the total controller 70, from which the images are then transferred to the display unit 72 for display and classification of each image in GUI screen mode. Thus, information on position coordinates of the defects is acquired and review results are acquired. That is to say, when the stages 11, 12 are moved, the reviewing optical microscope 80 observes images of the contamination or defects (including false defects) on a wafer 1, detected by the image processor 40 of the defect inspection apparatus and stored into the storage unit 73, for example. Next, the microscope 80 acquires review images of the various forms of contamination or defects shown as 3903 in FIG. 42, and supplies the images to the total controller 70. In the total controller 70, the position coordinates and other information of the reviewed defects are then used for the irradiation optical system 20, the detection optical system 30, and the image processor 40 to conduct the defect detection parameter setting steps shown in FIG. 43. This makes it possible to detect the defects that have been located and classified in accordance with the position coordinates and other information. In addition, since the reviewing optical microscope 80 can acquire enlarged images of defects, it is possible to conduct detailed analyses and consequently to estimate causes of the defects.

Next, specific examples of the irradiation optical system 20 which is a feature of the present invention are described below using FIGS. 3 to 12. The description assumes that chips "1aa" are arrayed in X-axis and Y-axis directions on a wafer "1a" and that major straight lines in internal circuit patterns of the chips "1aa" are formed facing in the X-axis and Y-axis directions. The description also assumes that the wafer "1a" is caused to travel in the X-axis direction and that Y-axial movements of the wafer are intermittent.

Figure 3:
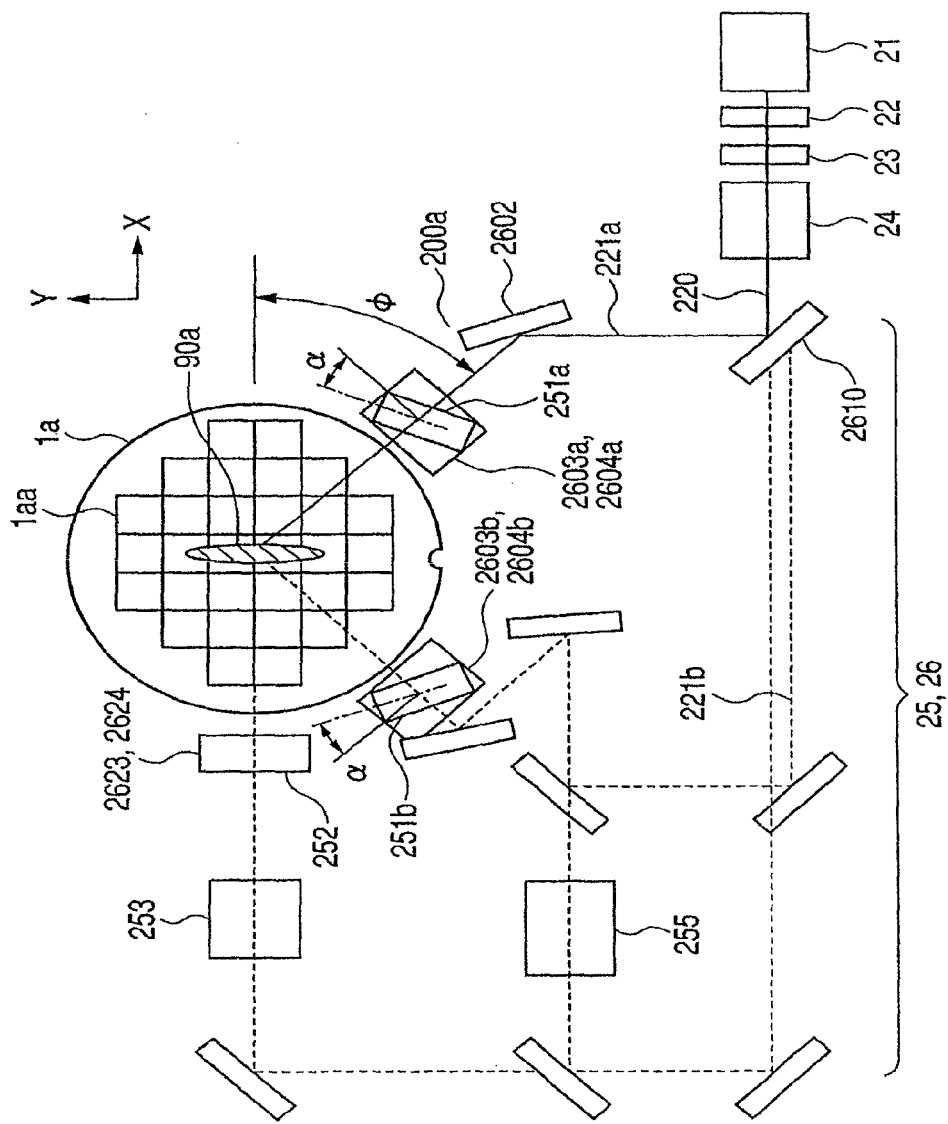
FIG. 3 is a plan view illustrating an example of an irradiation optical system according to the present invention, the example mainly showing a principal optical path and a first optical path.
Figure 9A:
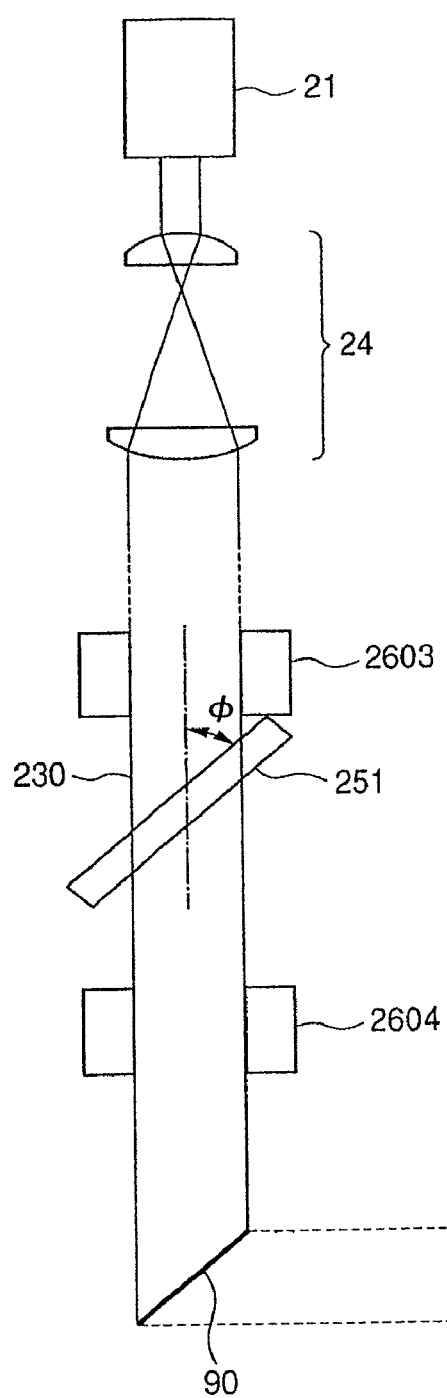
FIGS. 9A and 9B are diagrams illustrating an example of φ-angled irradiation optics including a cylindrical lens and a mirror and adapted for slit-shaped beam irradiation according to the present invention, the irradiation optics being shown in a form developed in an optical-axis direction.
Figure 9B:
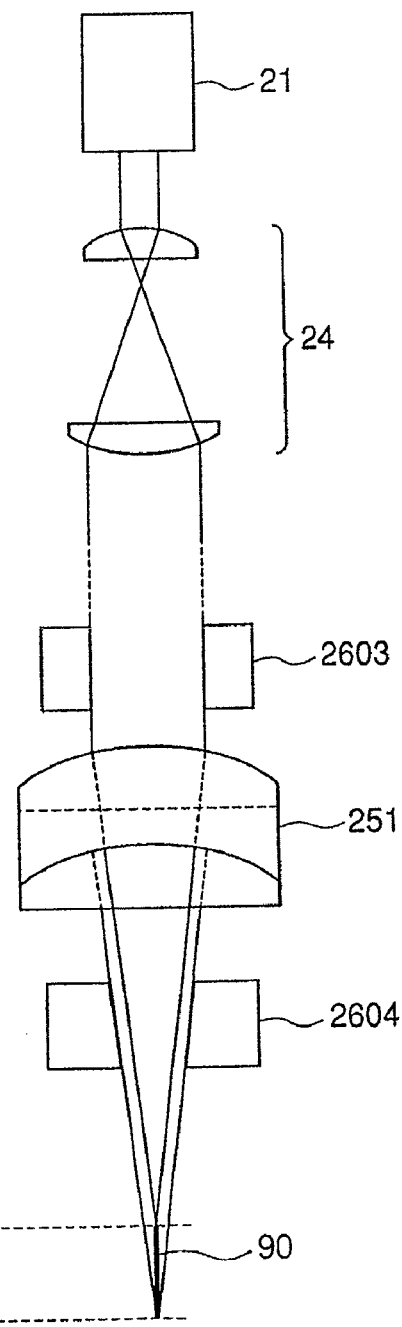
Figure 13A:
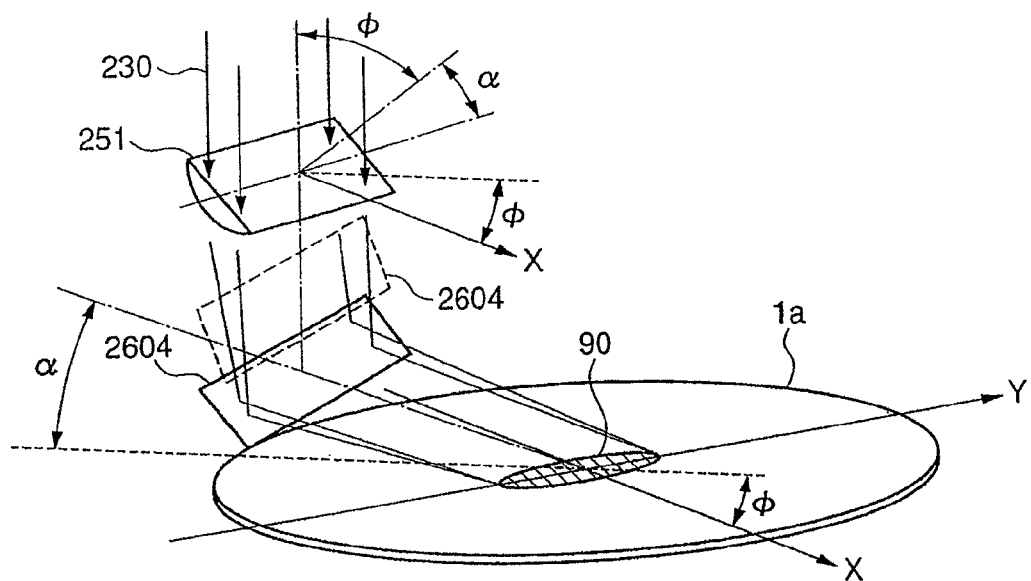
FIG. 13A is a perspective view that shows wafer irradiation with a slit-shaped beam according to the present invention by use of the φ-angled irradiation optics including a cylindrical lens and a mirror.

FIG. 3 shows an example in which, in order to match a longitudinal direction of a first slit-shaped beam 90a to a Y-axis direction, a clockwise φ-angled irradiation optical system 200a irradiates the beam at a clockwise inclination angle φ (e.g., 45 degrees) with respect to an X-axis direction when the beam is viewed from above, and from a direction of an inclination angle $\alpha$ (about 5 to 55 degrees) with respect to a horizontal surface. In the example of FIG. 3, a laser beam that has been expanded in diameter by a principal-beam expanding optics 24 on a principal optical path 220 is reflected by a mirror 2610 and guided to a first optical path 221a. The thus-guided first beam flux is horizontally reflected by a mirror 2602 and then emitted at clockwise inclination angle $\phi$ (e.g., 45 degrees) with respect to the X-axis. More specifically, as shown in FIGS. 9A, 9B, and 13A, the first beam flux, after being reflected directly downward by a first mirror 2603a, is converged in one direction by a first cylindrical lens 251a that is provided obliquely at an inclination angle $\phi$ with respect to an optical axis of a beam flux 230 having an inclination angle $\phi$ extending horizontally, and that is provided rotatedly at an elevation angle $\alpha$ about the optical axis of a beam flux 230, then further reflected by a first inclined mirror 2604a that can be switched, and emitted as the first slit-shaped beam 90a to the surface of the wafer from the direction of the angle $\alpha$. That is to say, to obtain a distance from a surface of incidence or surface of exit of the first cylindrical lens 251a to the slit-shaped beam 90a on the wafer, equal to a focal length of the first cylindrical lens 251a, the lens 251a is provided at the inclination angle $\phi$ with respect to the optical axis of the beam flux 230, and in rotated form with the elevation angle $\alpha$ about the optical axis of the beam flux 230. After being inclined at the angle $\phi$ from the X-axis direction, the first cylindrical lens 251a is further rotated longitudinally through an angle commensurate with the elevation angle $\alpha$ when viewed directly from above. In this way, the irradiation optical system for irradiating the slit-shaped beam 90a at the elevation angle $\alpha$ from the $\phi$ direction when viewed from above can be constructed only with the mirrors 2602, 2603a, 2604a, and the first cylindrical lens 251a. These optical elements (optical components) 251a, 2602, 2603a, 2604a can be manufactured easily and very accurately, which in turn enables easy assembly and adjustment of these elements and extensive cost reduction thereof.

The first inclined mirror 2603a is constructed such that its inclinational can be changed to a low angle of about 5-15 degrees and such that its inclination $\alpha 2$ can be changed to a high angle of about 40-55 degrees.

Figure 4:
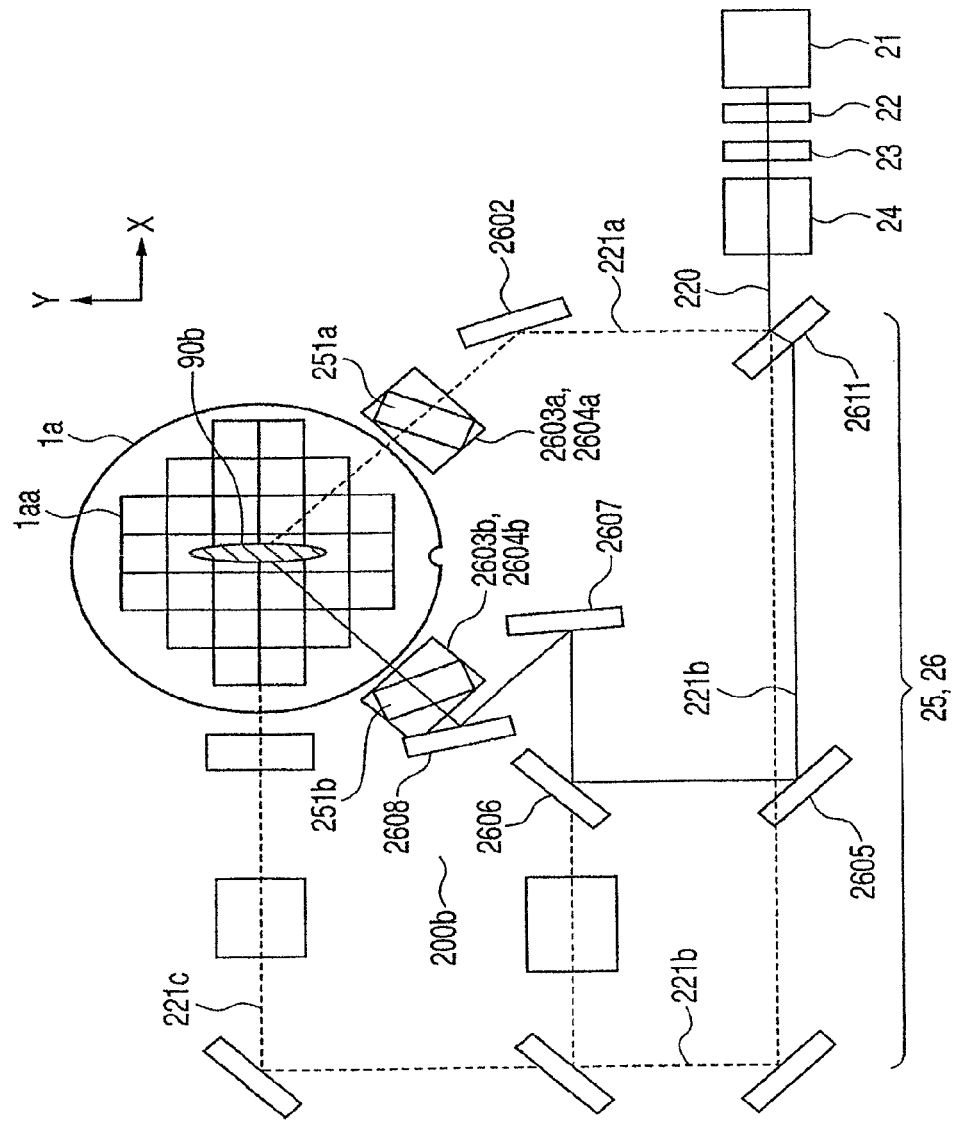
FIG. 4 is a plan view illustrating another example of the irradiation optical system according to the present invention, the example mainly showing a principal optical path and a second optical path.
Figure 5:
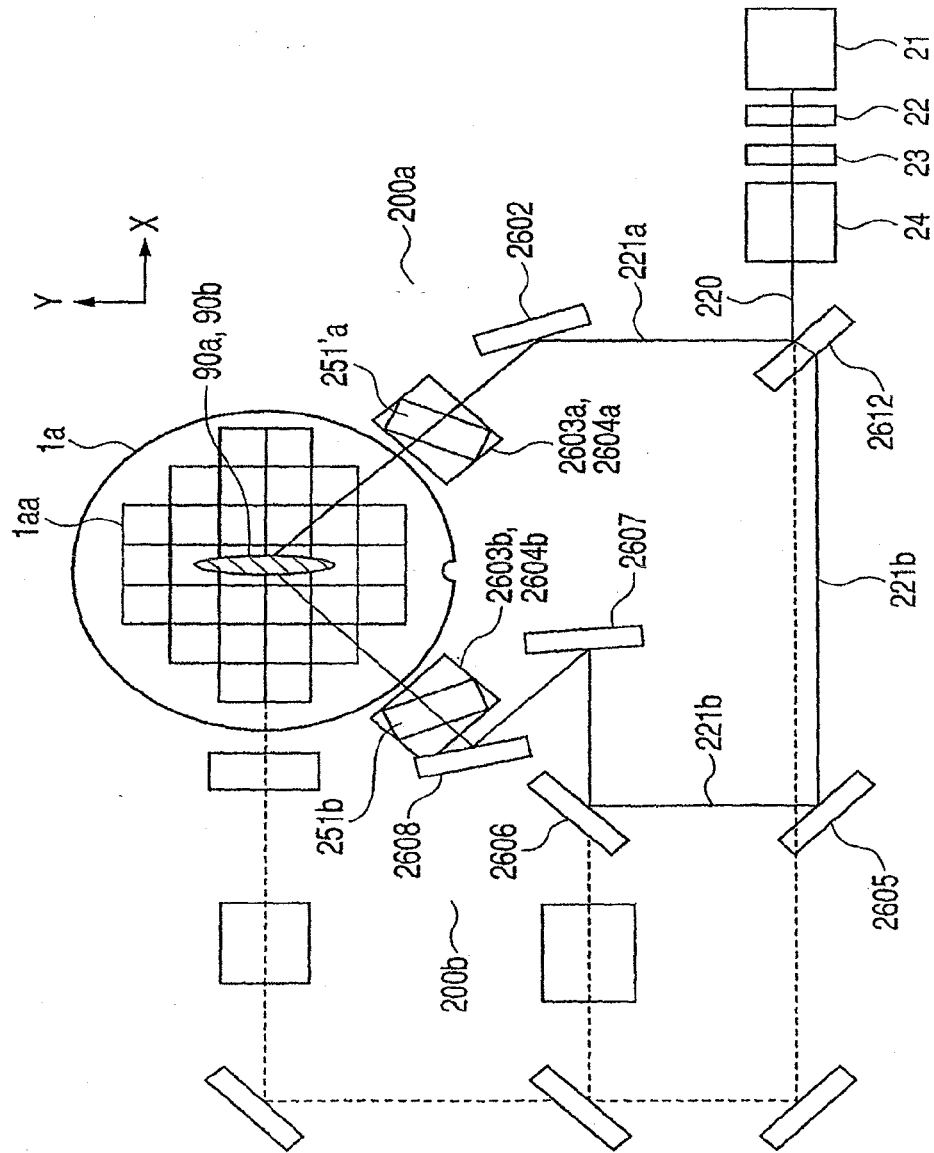
FIG. 5 is a plan view illustrating yet another example of the irradiation optical system according to the present invention, the example mainly showing a principal optical path and first and second optical paths.

FIG. 4 shows an example in which a counterclockwise $\phi$-angled irradiation optical system 200b irradiates a slit-shaped beam 90 in linearly symmetric form with respect to FIG. 3, from the opposite left side therein, that is, at a counterclockwise inclination angle $\phi$ (e.g., 45 degrees) with respect to the X-axis direction when the beam is viewed from above, and from a direction of an inclination angle $\alpha$ (about 5 to 55 degrees) with respect to the horizontal surface (plane). In the example of FIG. 4, transparent plate glass 2611 is used instead of the mirror 2610 such that as shown in FIG. 5, the beam is routed along a second optical path 221b similarly to routing established by using a half-mirror 2612 instead of the mirror 2610. In FIG. 4, a laser beam that has been expanded in diameter by the principal-beam expanding optics 24 is passed through the glass plate 2611 and then guided to selected second optical path 221b. The thus-guided laser beam is reflected by mirrors 2605, 2606, 2607, 2608, and emitted at counterclockwise inclination angle $\phi$ (e.g., 45 degrees) with respect to the X-axis. More specifically, as shown in FIGS. 9A, 9B, and 13A, the laser beam, after being reflected directly downward by a second mirror 2603b, is converged in one direction by a second cylindrical lens 251b provided obliquely at an inclination angle $\phi$ with respect to, and rotatedly through an elevation angle $\alpha$ about, the optical axis of the beam flux 230 having an inclination angle $\phi$ on the plane, then further reflected by a switchable second inclined mirror 2604b, and emitted as a second slit-shaped beam 90b to the surface of the wafer from the direction of the angle $\alpha$. That is to say, in order to obtain a distance from a surface of incidence or surface of exit of the second cylindrical lens 251b to the slit-shaped beam 90b on the wafer equal to a focal length of the second cylindrical lens 251b, the lens 251b is provided at the inclination angle $\phi$ with respect to the optical axis of the beam flux 230, and in rotated form with the elevation angle $\alpha$ about the optical axis of the beam flux 230. After being inclined at the angle $\phi$ from the X-axis direction, the second cylindrical lens 251b is further rotated longitudinally through an angle commensurate with the elevation angle $\alpha$ when viewed directly from above. In this way, the irradiation optical system for irradiating the second slit-shaped beam 90b at the elevation angle $\alpha$ from the $\phi$ direction when viewed from above can be constructed only with the mirrors 2605-2607, 2603b, 2604b, and the second cylindrical lens 251b. These optical elements (optical components) 251a, 2602, 2603a, 2604a can be manufactured easily and very accurately, which in turn enables easy assembly and adjustment of these elements and extensive cost reduction thereof.

FIG. 5 shows an example in which the clockwise $\phi$-angled irradiation optical system 200a and the counterclockwise $\phi$-angled irradiation optical system 200b irradiate the first slit-shaped beam 90a and the second slit-shaped beam 90b, respectively, from both sides in linearly symmetric form, at an inclination angle $\phi$ (e.g., 45 degrees) with respect to the X-axis direction when the beam is viewed from above, and from a direction of an inclination angle $\alpha$ (about 5 to 55 degrees) with respect to the horizontal surface. In the example of FIG. 5, the half-mirror 2612 is used instead of the mirror 2610 or the plate glass 2611. In FIG. 5, therefore, the first slit-shaped beam 90a in FIG. 3 and the second slit-shaped beam 90b shown in FIG. 4 can be irradiated at the same time.

Since, as described above, the slit-shaped beam 90 is irradiated from the direction having the inclination angle $\phi$ with respect to the X-axis direction, the zeroth-order diffracted light arising from the major straight-line group can be prevented from entering the aperture of the objective lens 31. In addition, if the patterns formed on the wafer are contact holes, capacitors, or the like, since these elements have no specific directivity, the beam is preferably irradiated from an oblique direction with the angle $\phi$ of about 45 degrees.

Figure 6:
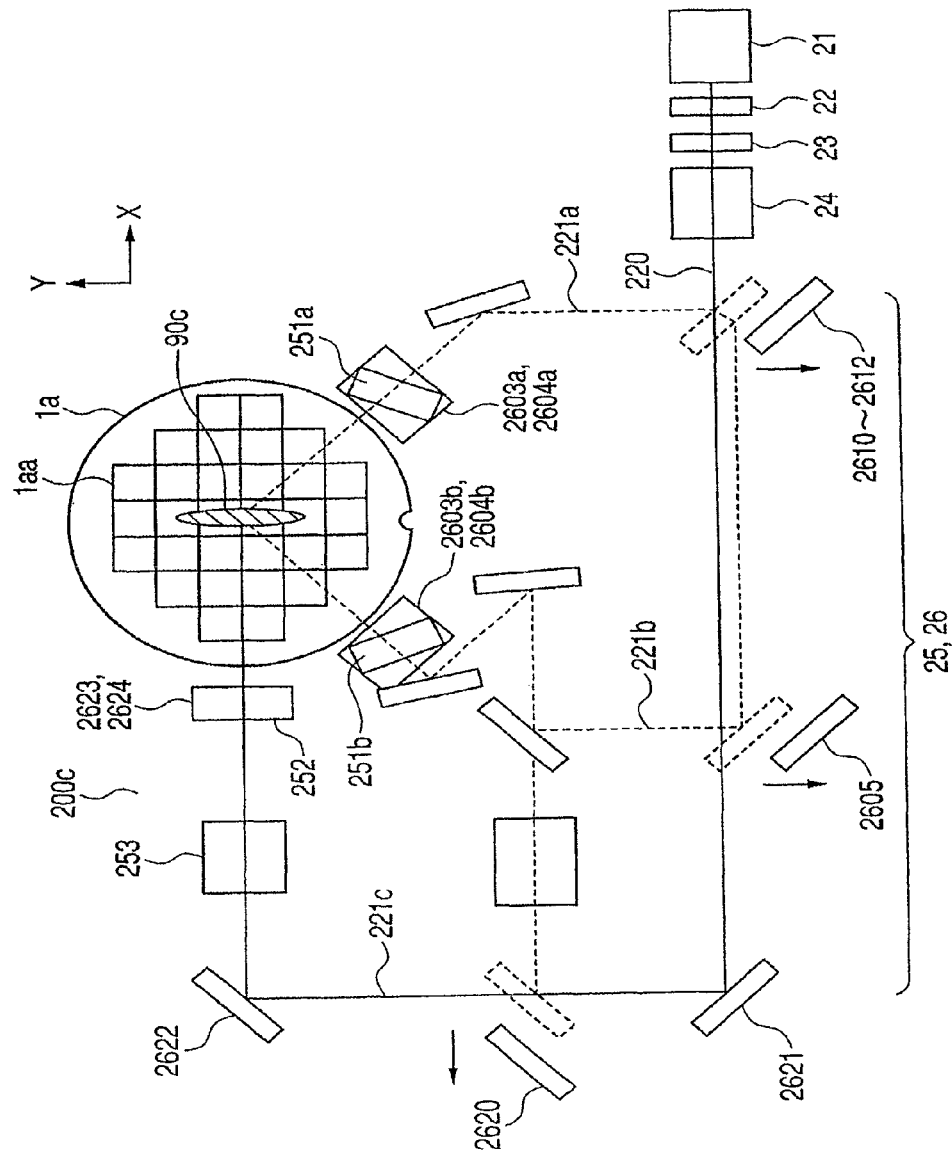
FIG. 6 is a plan view illustrating a further example of the irradiation optical system according to the present invention, the example mainly showing a principal optical path and a third optical path.
Figure 10A:
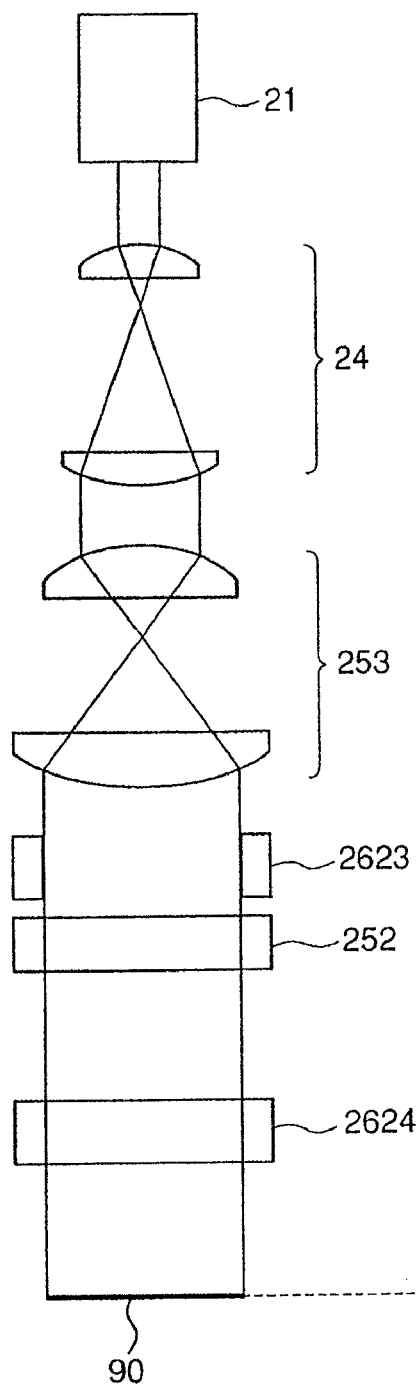
FIGS. 10A and 10B are diagrams illustrating an example of a section which consists of, in the present invention, (1/cos φ)-times beam-expanding optics and X-axial irradiation optics including a cylindrical lens and a mirror and adapted for slit-shaped beam irradiation, the two kinds of optics being shown in a form developed in an optical-axis direction.
Figure 10B:
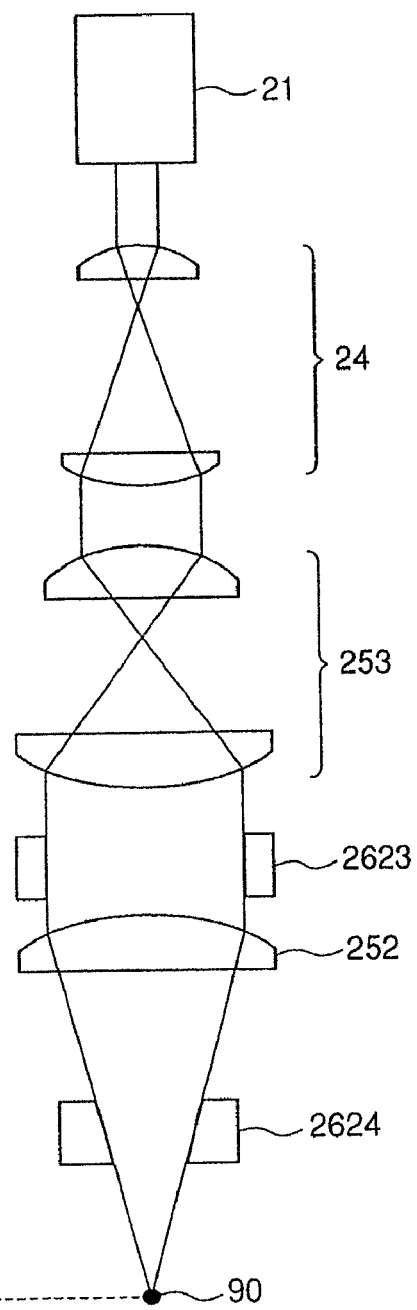
Figure 12:
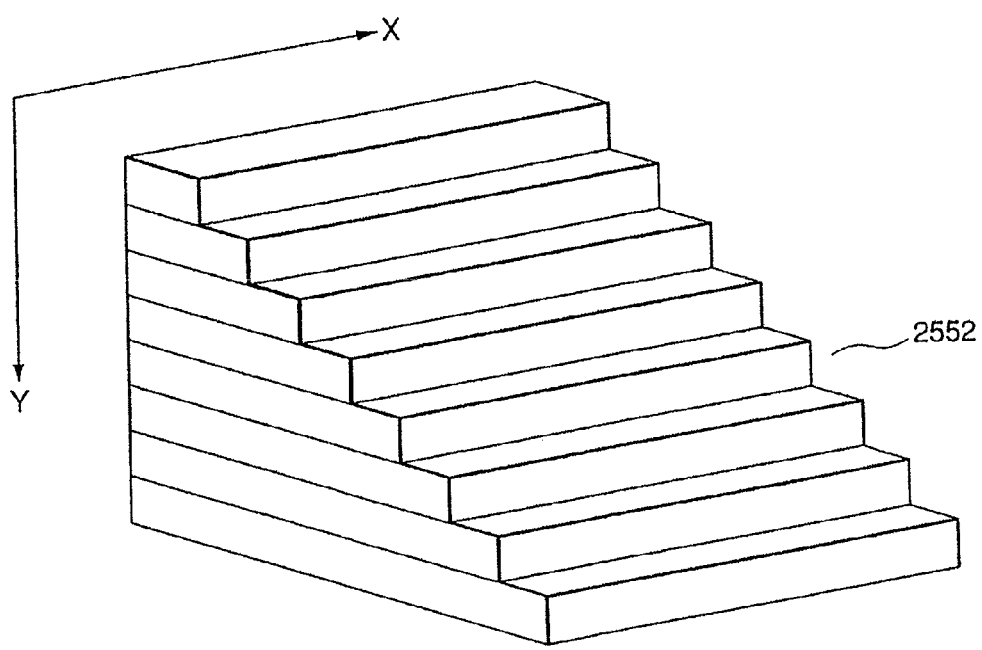
FIG. 12 is a perspective view showing an example of an optical member group used in the coherency reduction optics according to the present invention.
Figure 13B:
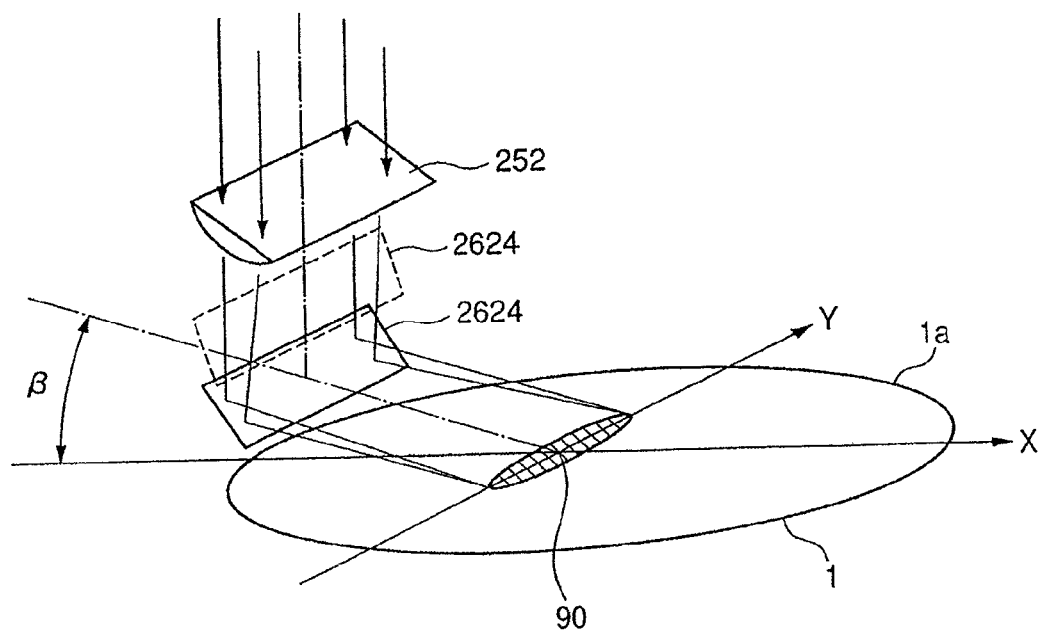
FIG. 13B is a perspective view that shows wafer irradiation with a slit-shaped beam by use of the X-axial irradiation optics including a cylindrical lens and a mirror.

FIG. 6 shows an example in which an X-axial irradiation optical system 200c irradiates a third slit-shaped beam 90c from the X-axis direction, which is a direction that the major straight-line group of the circuit pattern faces. In the irradiation optical system 200c of the FIG. 6, a longitudinal dimension of the third slit-shaped beam 90c needs to be matched to those of the first slit-shaped beam 90a and second slit-shaped beam 90b existing when the latter two beams are irradiated from an oblique direction of, for example, with the angle $\phi$ of about 45 degrees. This is why beam-expanding optics 253 for increasing the beam diameter by a factor of $(1/\cos \phi)$ ($\sqrt{2}$ if $\phi=45$ degrees) exists on a third optical path 221c as shown in FIGS. 10A, 10B. In the example of FIG. 6, after mirrors and/or other optical elements 2610-2612, 2605, 2620 have been moved out from the third optical path 221c, the laser beam that has been expanded in diameter by the principal-beam expanding optics 24 is reflected by mirrors 2621, 2622, and then the beam is further expanded in diameter by a factor of $(1/\cos \phi)$ ($\sqrt{2}$ if $\phi=45$ degrees) by the beam-expanding optics 253. Next as shown in FIG. 13B, the laser beam is further reflected directly downward by a third mirror 2623, then converged in one direction by a third cylindrical lens 252, and further reflected by the switchably disposed third inclined mirror 2624. After this, the laser beam is irradiated from a β-angle direction as the third slit-shaped beam 90c. Diffracted light (scattered light) from any contamination or other defects present in concave portions between the wiring patterns each formed by a major straight-line group can be detected with the image sensor 36 by, as described above, irradiating the third slit-shaped beam 90c obliquely from the X-axis direction. Switchable third inclined mirror 2624c is constructed such that its inclination β1 can be changed to a low angle of about 5-15 degrees and such that its inclination β2 can be changed to a high angle of about 40-55 degrees. For detection of defects present in concave portions between the wiring patterns, the switchable third inclined mirror 2624c is preferably switched to a high angle of inclination.

Figure 7:
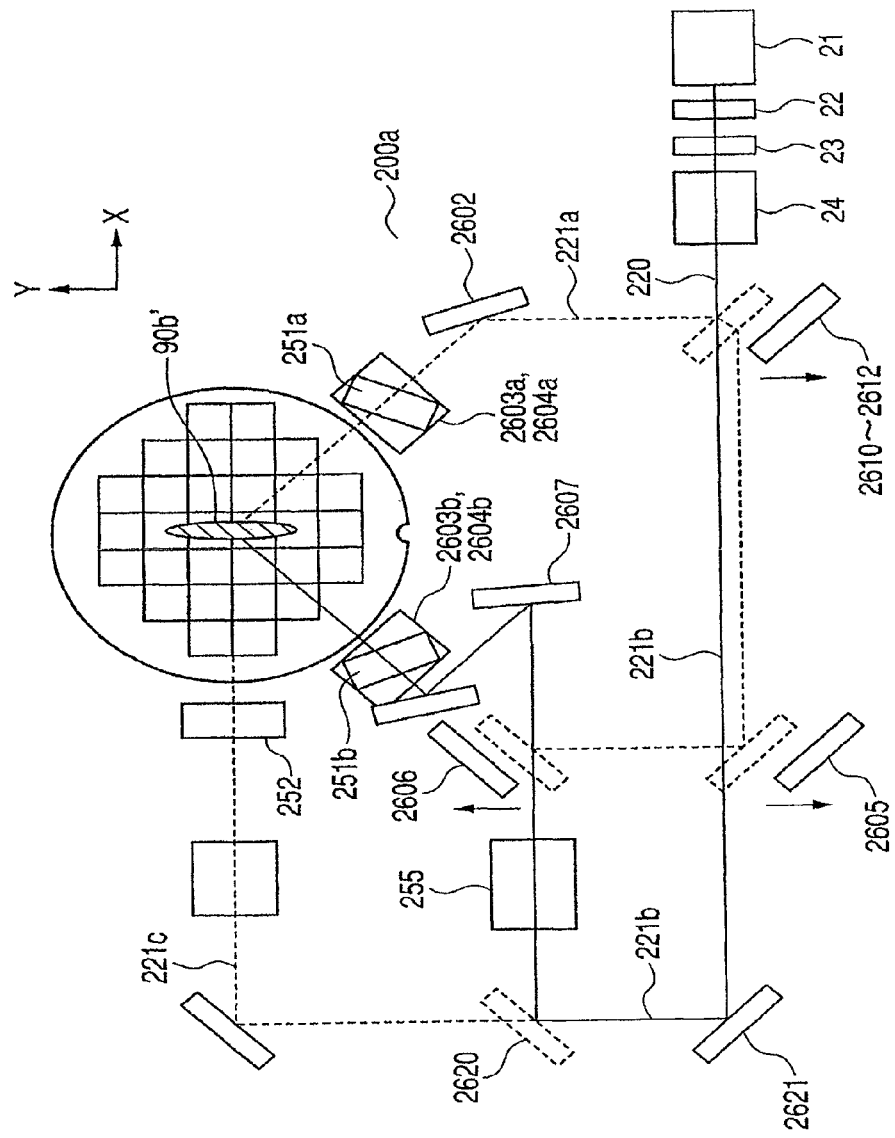
FIG. 7 is a plan view illustrating a further example of the irradiation optical system according to the present invention, the example mainly showing a principal optical path and a second optical path on which coherency reduction optics is installed.

FIG. 7 shows an example in which a coherency reduction optical system 255 of a simple configuration is used to irradiate a beam from the left side at an inclination angle φ (e.g., 45 degrees) with respect to the X-axis direction when the beam is viewed from above, and from a direction of an inclination angle α (about 5 to 55 degrees) with respect to the horizontal surface (plane). In the example of FIG. 7, the mirror 2620 is moved into the second optical path 221b and the mirrors and/or other optical elements 2605, 2606, 2610-2612 are moved out from the second optical path 221b. As described in Japanese Laid-Open Patent Application Publication (JP Kokai) No. 2004-156142 and as shown in FIG. 11B, the coherency reduction optical system 255 includes beam-expanding optics 2551 adapted to expand a beam in diameter in at least one direction (light-converging direction of the cylindrical lens 251b), and an optical member group 2552 formed by stacking a plurality of plate-shaped optical members each having a different optical path length in at least a light-converging direction to allow entry of a coherent laser beam and emit a plurality of slit-shaped beams each spatially reduced in coherency, in the light-converging direction. The coherency reduction optical system 255 further includes the second cylindrical lens 251b and second inclined mirror 2604b constituting the light-converging optics constructed such that the plurality of slit-shaped beams each spatially reduced in coherency are converged in the light-converging direction and irradiated onto the surface of the wafer from an α-angled direction as a slit-shaped beam 90b'. Consequently at the second cylindrical lens 251b, the slit-shaped beam 90b' is converged in the light-converging direction to achieve multi-angle irradiation. In this manner, the plurality of slit-shaped beams each spatially reduced in coherency are converged through the second cylindrical lens 251b by changing an irradiation direction of each beam over a wide range as shown in FIGS. 11A and 11B, and then a rough edge section of an ultrafine-structured circuit pattern is irradiated with the slit-shaped beam 90c'. For this reason, an incoming, smoothed reflection/diffraction pattern (except for the zeroth-order) is converged on the objective lens 31 from the rough edge section of the ultrafine-structured circuit pattern, the light is received by the image sensor 36 such as a TDI sensor, and a smoothed image signal is detected from the rough edge section.

The coherency reduction optical system 255 including the beam-expanding optics 2551 and the optical member group 2552 is built into the counterclockwise θ-angled irradiation optical system 200b, that is, the second optical path 221b. The coherency reduction optical system 255 may be provided in the first optical path 221a or the third optical path 221c if installation space requirements permit this configuration. However, it is possible to install the coherency reduction optical system 255 in any other optical path if this path is formed so as to be insertable into and retreatable from the first optical path 221a or the third optical path 221c or selectable as a shunt to replace either of the latter two paths.

Figure 8:
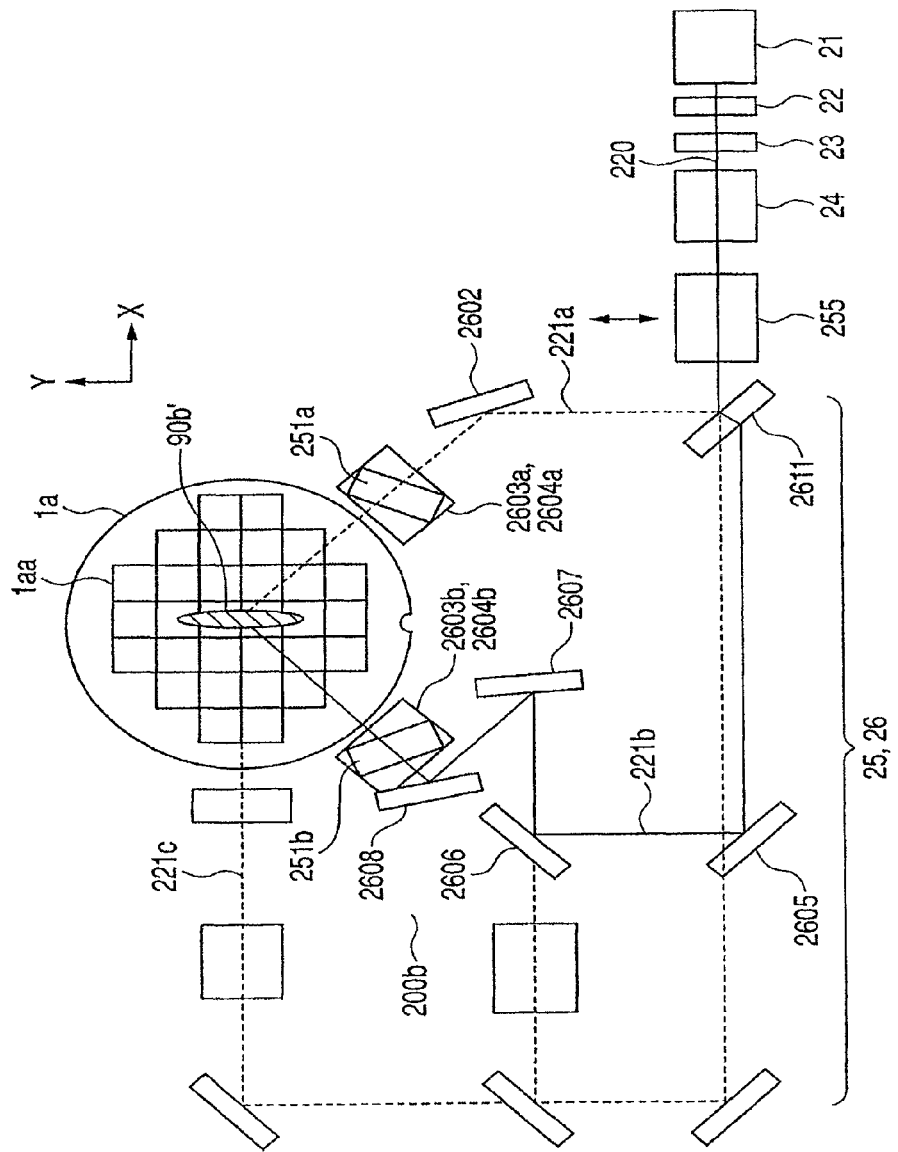
FIG. 8 is a plan view illustrating a further example of the irradiation optical system according to the present invention, the example mainly showing a principal optical path having coherency reduction optics installed thereon, and a second optical path.

Alternatively, if the principal optical path 220 is constructed to be installable, the coherency reduction optical system 255 may be provided between the principal-beam expanding optics 24 forming the principal optical path 220, and the optical elements 2610-2612. In this case, any one of the first optical path 221a, the second optical path 221b and the third optical path 221c can be used to irradiate a beam of reduced coherency, as the slit-shaped beam 90. FIG. 8 shows an example in which the second optical path 221b is used. In this example, since the coherency reduction optical system 255 may be unnecessary, the optical system 255 needs to be constructed such that it can be insertable into and retreatable from the principal optical path 220.

As described above, slit-shaped beam 90, 90' can be irradiated in any one of five ways. In addition, in consideration of using two different values as the inclination angles α and β each, 10 ways are available to irradiate the beam.

The present invention is characterized in that, in the clockwise φ-angled irradiation optical system 200a and the counterclockwise φ-angled irradiation optical system 200b, the same functions as those of the conical lenses described in JP Kokai Nos. 2000-105203 and 2004-177284 are implemented using the cylindrical lens 251 and the switchable inclined mirror 2604. As can be understood from this, since special optical components are not used, the above optical elements (optical components) 251, 2602-2604 can be manufactured easily, and since the cylindrical lens 251, in particular, has a predetermined focal length, adjustment of these elements is easy and extensive cost reduction is possible.

In addition, in the irradiation optical system 20 according to the present invention, if, as shown in FIG. 7, the mirror 2620 is inserted into an optical path, the mirrors and/or other optical elements 2610-2612, 2605, 2606 are moved out from the optical path, and the coherency reduction optical system 255 is installed between the mirrors 2620 and 2607. Thus, the slit-shaped beam 90' of reduced coherency can be irradiated at, for example, 45 degrees with respect to the X-axis direction and a smoothed image signal can be detected from the rough edge section of the ultrafine-structured circuit pattern.

Furthermore, in the irradiation optical system 20 according to the present invention, the laser beam emitted from the laser light source 21 has a Gaussian distribution as shown in FIG. 14. Thus, to suppress the change in illuminance within a detection field 210 (longitudinal width of a rectangular light-receiving surface of the TDI sensor 36), longitudinal width of the slit-shaped beam 90, 90' (i.e., the beam width for a 13.5% illuminance) can be increased by extending the beam width (for the 13.5% illuminance) by use of the beam-expanding optics 24.

Figure 16:
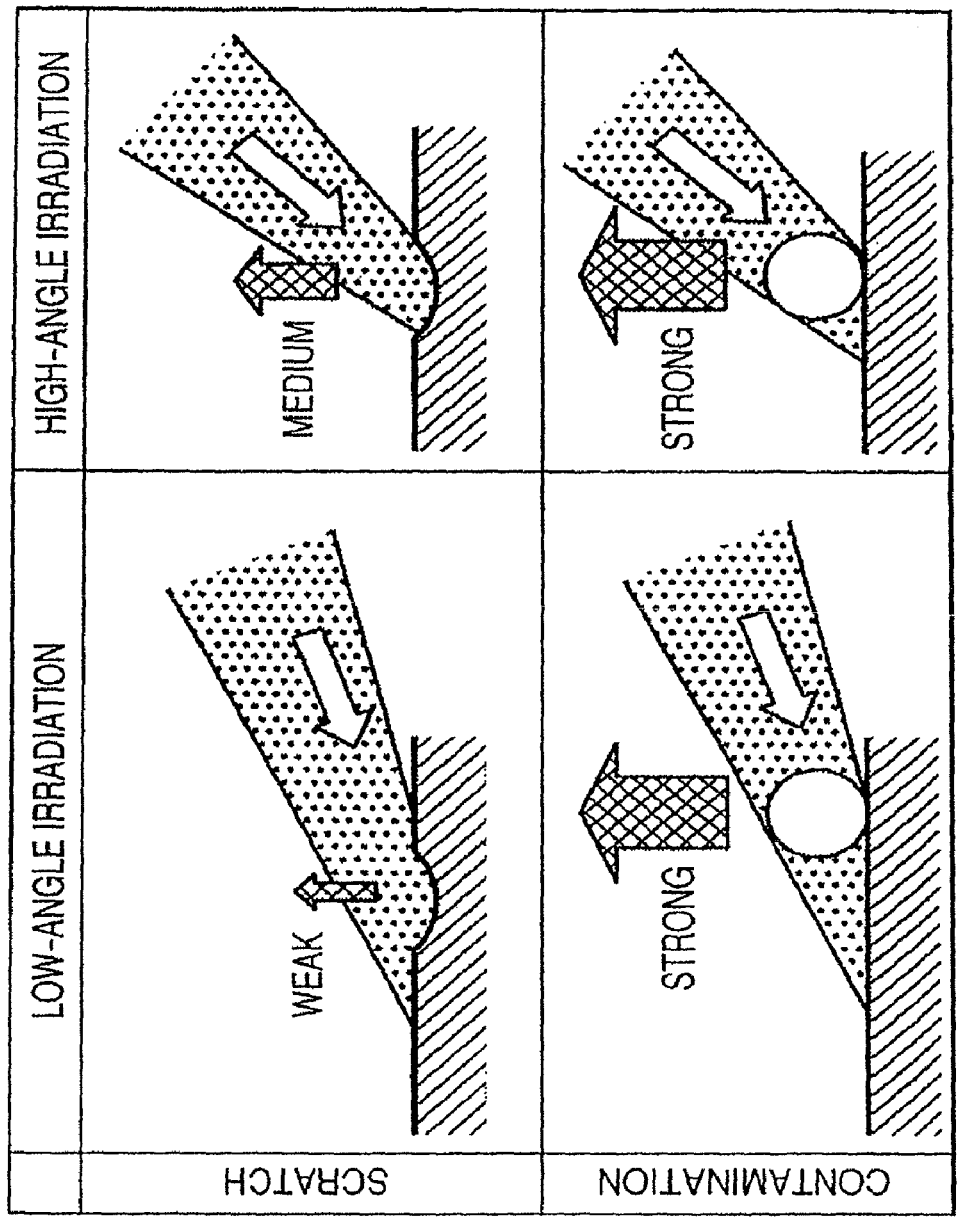
FIG. 16 shows the differences in scattered light intensity, obtained during low-angle and high-angle irradiation of particle-like contamination and a scratch according to the present invention.

Selection of an inclination angle (elevation) α, β by means of the switchable inclined mirror 2604, 2624, is described below using FIGS. 15A, 15B, 16, 17. FIG. 15A shows an example of irradiating the slit-shaped beam 90, 90' at a low angle α1, β1 (about 5 to 10 degrees) using the switchable inclined mirror 2604, 2624, and FIG. 15B shows an example of irradiating the slit-shaped beam 90, 90' at a high angle α2, β2 (about 40 to 50 degrees) using the switchable inclined mirror 2604, 2624. Examples of independent low-angle irradiation and high-angle irradiation for detection of scratches and contamination each are shown in FIG. 16. As is obvious from FIG. 16, during low-angle irradiation, normal particle-like contamination is detected as high-intensity scattered light, and the same also applies to high-angle irradiation.

Figure 17:
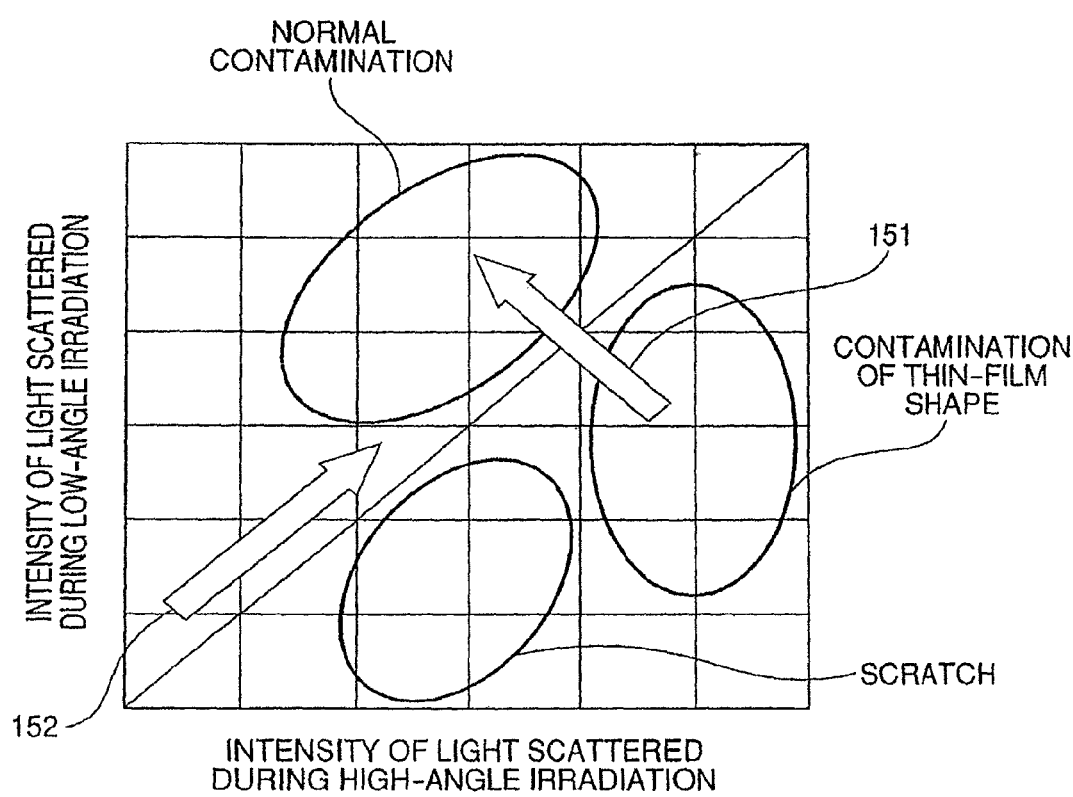
FIG. 17 is an explanatory diagram indicating that it is possible to determine particle-like contamination, thin-film-like contamination, or a scratch, based on the differences in scattered light intensity during low-angle and high-angle irradiation according to the present invention.

Compared with the above contamination, however, scratches are thin in a vertical direction (i.e., small in depth), so during low-angle irradiation, scratches are detected as low-intensity scattered light, and during high-angle irradiation, they are detected as scattered light of a medium intensity level. In addition, as shown in FIG. 17, thin-film-like contamination has a two-dimensional spread, compared with scratches, so during high-angle irradiation, thin-film-like contamination is detected as high-intensity scattered light, and during low-angle irradiation, thin-film-like contamination is detected as scattered light of a medium intensity level. Arrow 151 in FIG. 17 indicates an increase in height of a defect, and arrow 152 indicates an increase in planar area (spread). Partly for discrimination between normal particle-like contamination, scratches, and thin-film-like contamination, therefore, it becomes necessary to select the inclination angle (elevation) $\alpha$, $\beta$ for the split-shaped beam 90, 90c by means of the switchable inclined mirror 2604, 2624.

Next, another example of a detection optical system is described below using FIG. 19. The detection optical system 30' shown as another example in FIG. 19 differs from the detection optical system 30 of FIG. 2 in that in a vertical plane inclusive of the X-axis or in a vertical plane with 45 degrees to the X-axis, a detection optical axis 38 may be inclined to a normal line with respect to the wafer 1, in a direction of opening to the slit-shaped beam of light irradiated. The detection optical axis 30 is shown in a left-inclined condition in FIG. 19, but if the irradiation optical system 20 is constructed as in FIGS. 4 to 7, the detection optical axis 30 will be inclined to the right since the slit-shaped beam 90, 90c will enter from the left side. Inclining the detection optical axis 30 in this way will reduce a ratio of the light diffracted (scattered) from very small concave/convex portions on the wafer surface, with respect to the light diffracted (scattered) from any contamination on the wafer surface. As a result, the light can be made to enter the aperture in the objective lens 31 and a detection signal of the contamination can be improved in S/N ratio.

Figure 2:
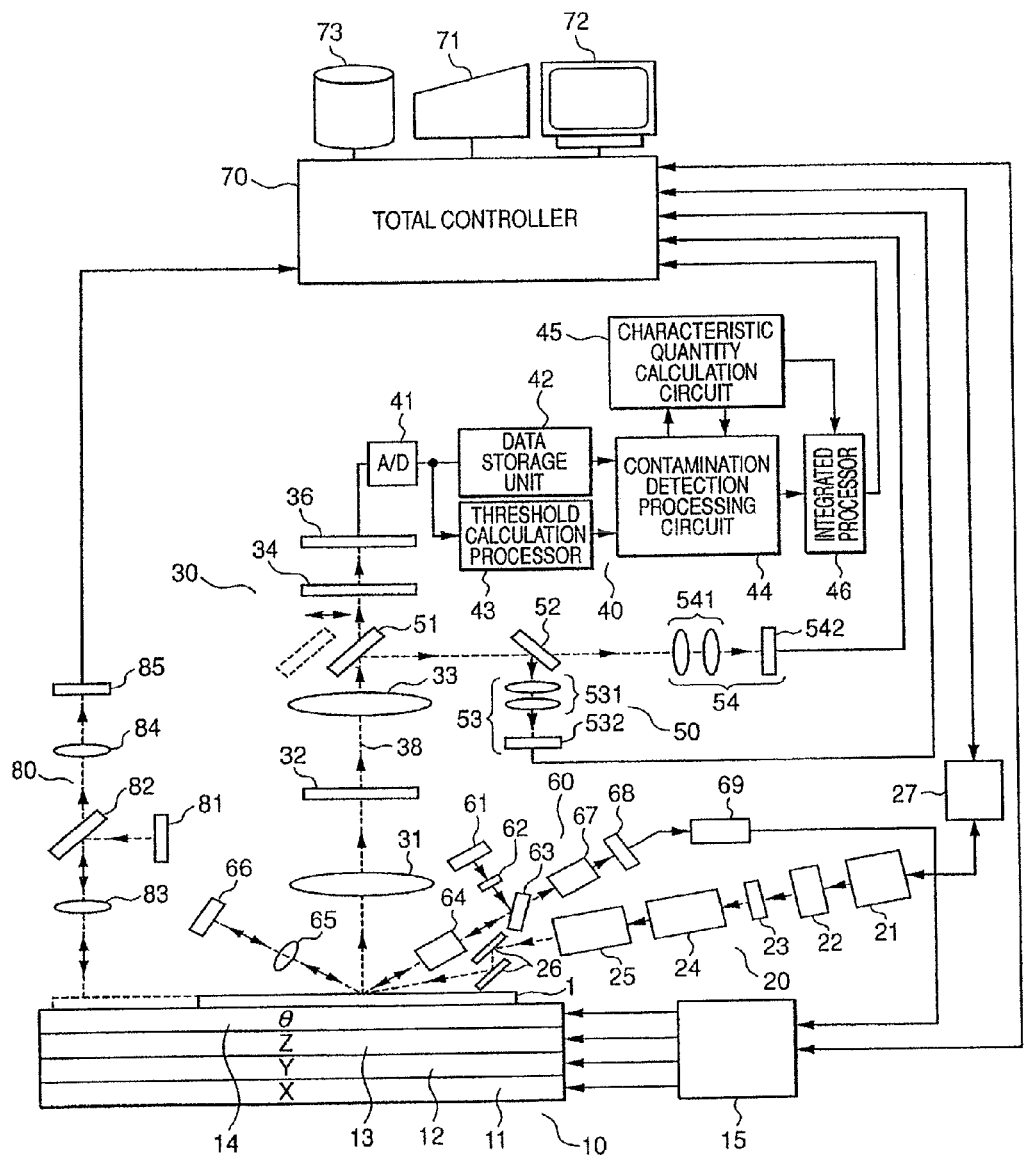
FIG. 2 is a schematic configuration diagram showing an embodiment of a defect inspection apparatus according to the present invention.
Figure 19:
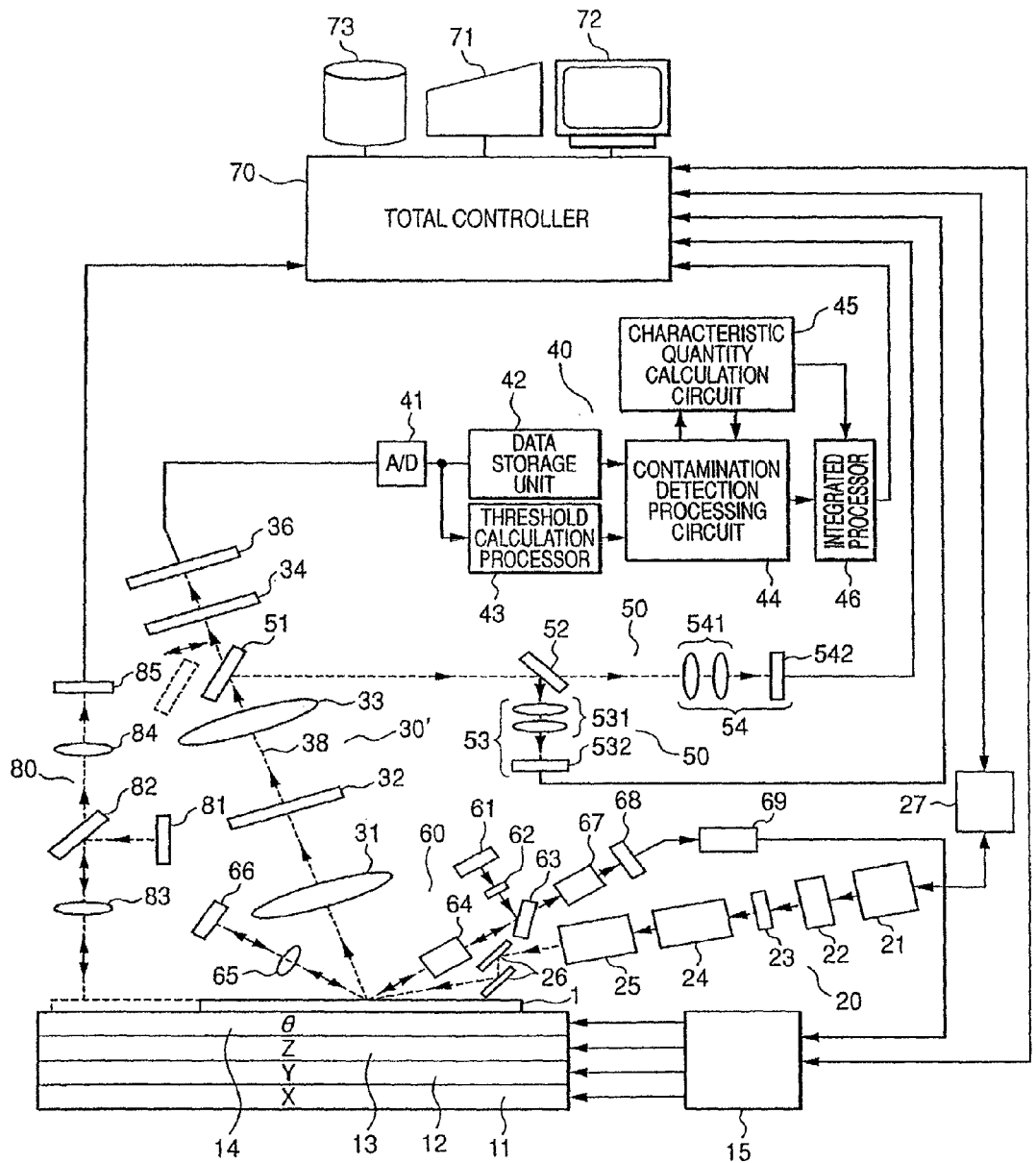
FIG. 19 is a diagram showing a total schematic configuration of the detection optical system in its inclined state according to the present invention.
Figure 20A:
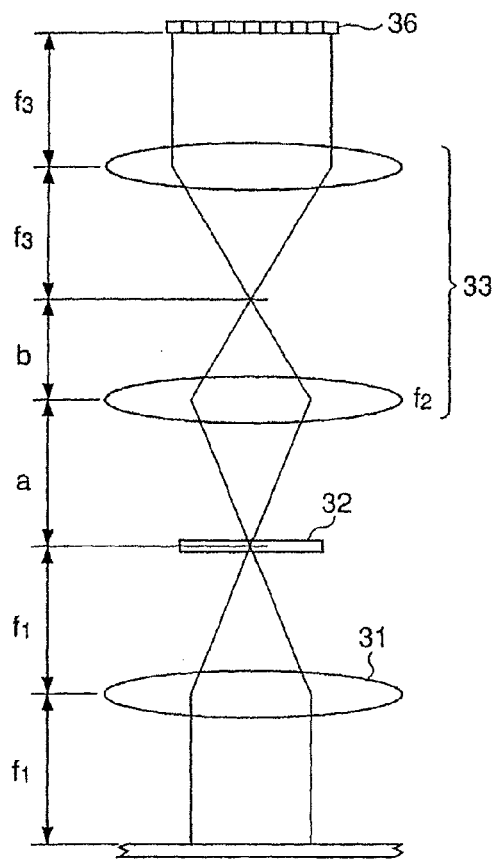
FIGS. 20A and 20B are diagrams that show examples of the detection optical system constructed to make a magnification variable in the present invention.
Figure 20B:
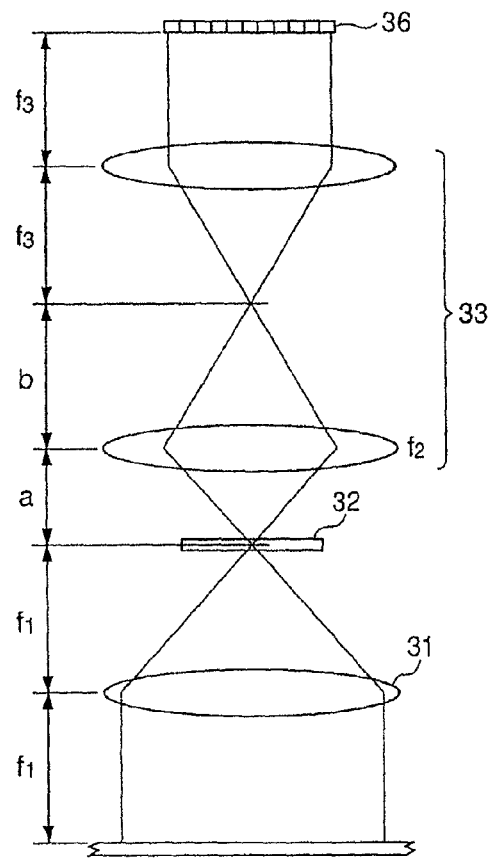

As an alternative measure, the detection optical systems 30 and 30' shown in FIGS. 2 and 19, respectively, may be adapted to have a zoom function to obtain a variable detection magnification, as shown in FIGS. 20A and 20B.

When an iterative pattern is irradiated with the slit-shaped beam 90, 90', such diffracted light from the iterative pattern as shown in FIG. 21B will interfere according to the particular pattern regions P1, P2, P3 in the chips arrayed on the wafer, as shown in FIG. 21A, and diffracted light patterns (diffraction images) FP1, FP2, FP3 will result. The diffracted light patterns (diffraction images) FP1, FP2, FP3 can each be light-shielded using the spatial filter 32 provided at a position conjugate to the pupil of the objective lens 31. For high-throughput inspection, however, the inspection field is likely to take a large field size of several μm or more on the wafer. Accordingly, the split-shaped beam 90, 90' is to be irradiated across a region 651 which includes plural kinds of pattern regions P1, P2, P3 of different pattern pitches. In this case, the Fourier transform image observed will, as shown in FIG. 21C, appear as a logical sum of FP1, FP2, FP3. If, in this state, inspections are conducted using a spatial filter that has synthesized the diffracted light patterns FP1, FP2, FP3, this offers the advantage that the diffracted light patterns FP1, FP2, FP3 from the pattern regions P1, P2, P3, can be simultaneously light-shielded for reduced signal levels of the signals sent from the iterative circuit pattern. At the same time, however, there is also the disadvantage that since the light scattered from the defects will also be significantly shielded, signals from the defects will be reduced in signal level. In order to avoid this disadvantage, therefore, the diffracted light patterns from the plural kinds of pattern regions are cleared by conversion into a Fourier transform image. That is to say, this can be accomplished by, for example, switching each diffracted light pattern of the spatial filter 32 to FP1, FP2, and FP3, according to the pattern regions P1, P2, P3, respectively, for each scan of the entire wafer surface. Since layout coordinates of the pattern regions p1, P2, P3 in the chips are based on CAD information and thus known, the signal obtained by the image sensor 36 through acquiring an image of the pattern region which has matched to the particular diffracted light pattern can be made effective as a defect detection signal in accordance with the known layout coordinates. The number of scans thus conducted on the entire wafer surface will increase with an increase in the number of spatial filters 32 used, but the light scattered from the defects can be received at the image sensor 36 without being significantly shielded, by switching each pattern to be light-shielded with a specific spatial filter 32, and thus, defect detection sensitivity can be improved.

Two methods are available to clear simultaneously the diffracted light patterns from the plural kinds of pattern regions by conversion into a Fourier transform image. One possible method is by inserting an irradiation range-limiting diaphragm into an optical path of the irradiation optical system to prevent the slit-shaped beam 90, 90' from being irradiated spanning different kinds of pattern regions, or by making the beam-expanding optics 24 movable and modifying a beam-expanding magnification for a limited irradiation range. The other possible method is by providing a diaphragm in order for the diffracted light incident on a Fourier transform plane to be restricted into diffracted light of a smaller angle of incidence to reduce an N.A. value of the Fourier transform lens 31 used.

Selecting either of the above methods makes it possible for only the diffracted light pattern from a specific pattern region to be formed on the Fourier transform plane. Consequently, a light-shielding pattern appropriate for the diffracted light pattern from the specific pattern region can be set as the spatial filter 32, and the defects in the specific pattern region can be inspected with high sensitivity.

Figure 22:
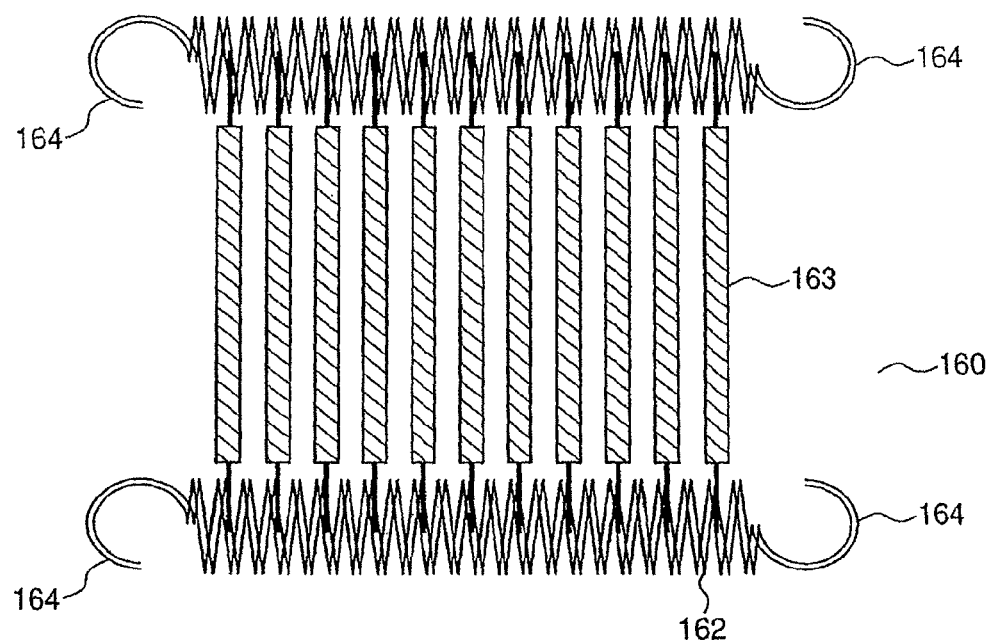
FIG. 22 is a diagram showing an example of a pitch-variable spatial filter in the present invention.
Figure 23:
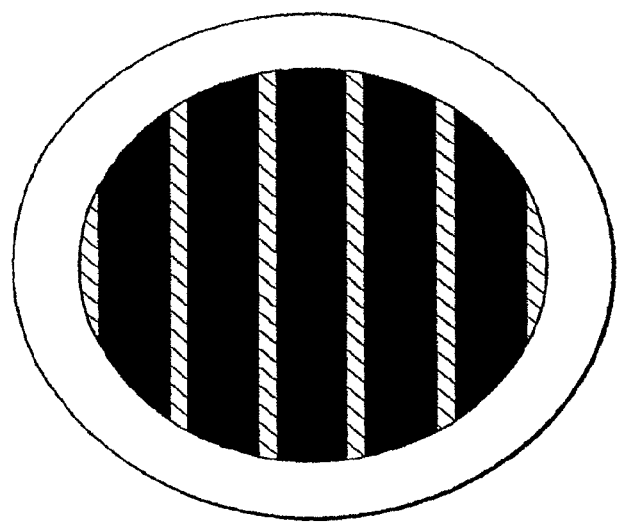
FIG. 23 is a diagram showing a light-shielding pattern formed by the spatial filter shown in FIG. 22.

The spatial filter 32 may otherwise be constructed using a pitch-variable filter 160 constituted by plate-shaped or rod-shaped optical shielding members 163 arrayed between springs 161 and 162 coiled in mutually inverse directions, as shown in FIG. 22. For the filter 160, pitches between the optical shielding members 163 can be varied by changing a distance between hooks 164, and the diffracted light patterns FP1 and FP3 shown in FIG. 21B can be light-shielded by using such a light-shielding pattern as shown in FIG. 23. Of course, light-shielding of the diffracted light pattern FP2 shown in FIG. 21B is also possible, which can be achieved by installing two spatial filters 160 in stacked form to make respective optical shielding member arrays 163 orthogonal to each other.

Figure 24:
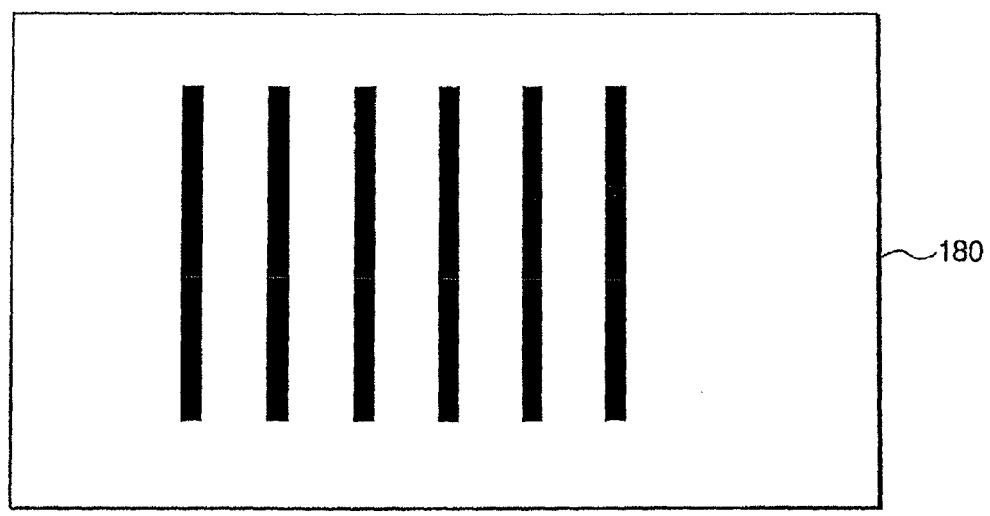
FIG. 24 is a diagram showing an example of a light-shielding pattern obtained when a liquid-crystal filter is used as the spatial filter in the present invention.
Figure 25:
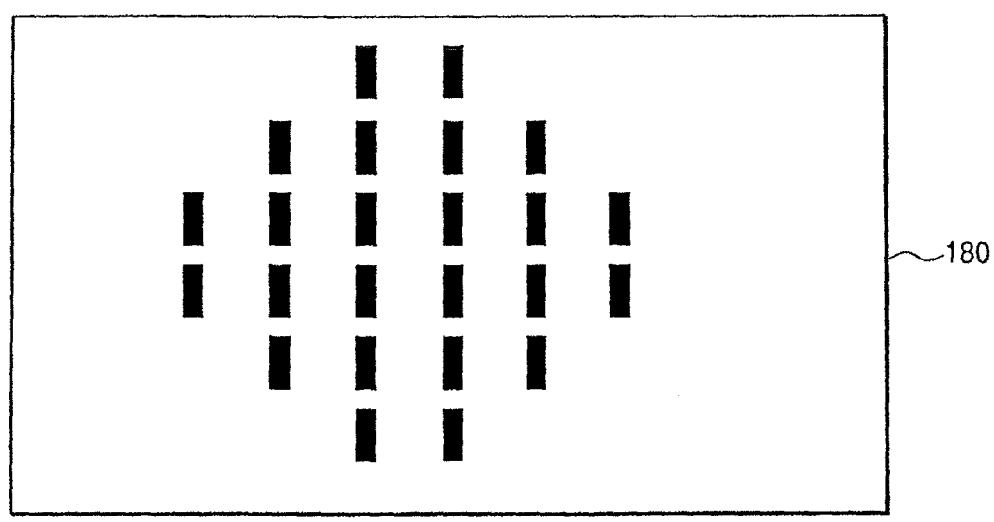
FIG. 25 is a diagram showing another example of a light-shielding pattern obtained when a liquid-crystal filter is used as the spatial filter in the present invention.

Further alternatively, the spatial filter 32 may be constructed using a liquid-crystal filter 180 capable of being formed with any pattern, as shown in FIGS. 24 and 25. FIG. 24 shows a filter having a linear light-shielding pattern, and FIG. 25 shows a filter having a light-shielding pattern of a chain-line shape.

The spatial filter 32 can otherwise be a filter having multiple kinds of light-shielding patterns printed thereon so as to be switchable from one pattern to another.

Next, a description is given below of an example of irradiating obliquely a polarized slit-shaped beam using the polarizing plate 23, and an example of detecting polarized light using the analyzer (polarizing filter) in the optical filter group

Figure 26:
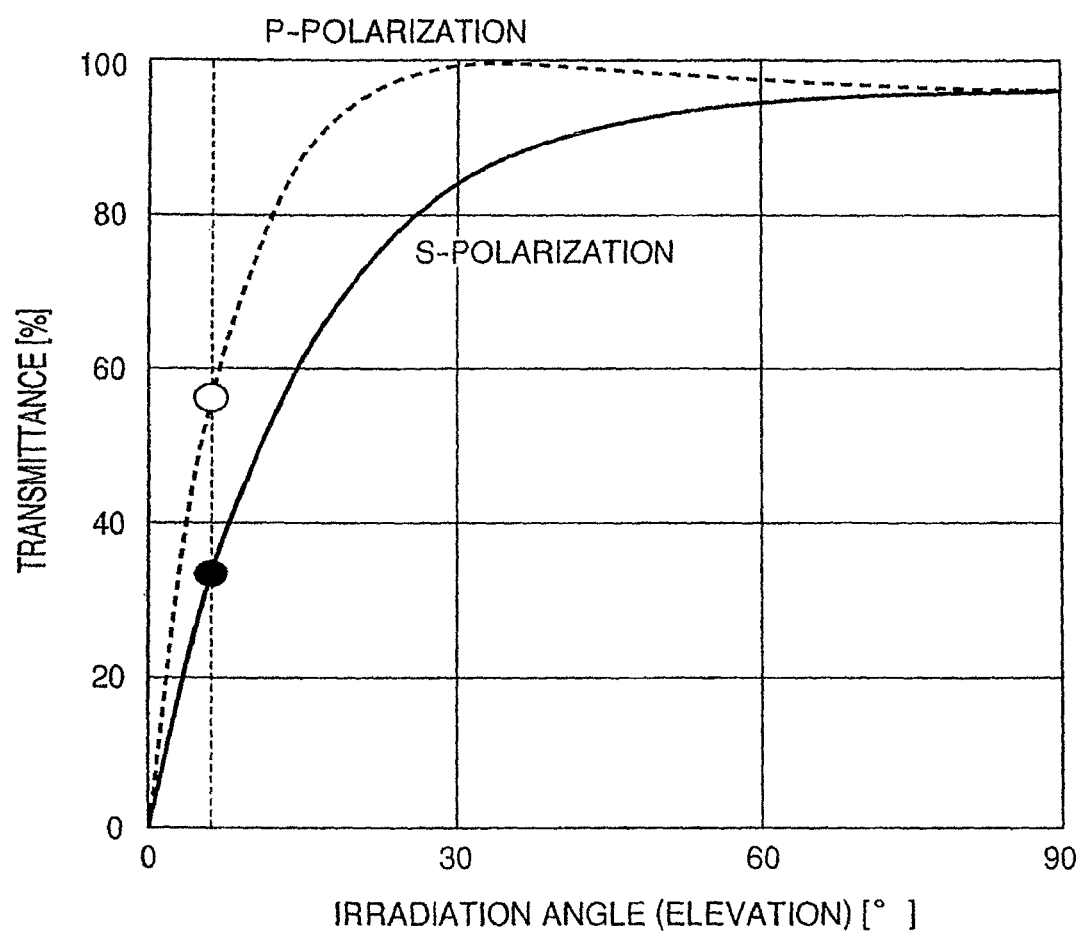
FIG. 26 is a diagram showing an elevation angle-transparent film transmittance relationship obtained during P-polarization and S-polarization process steps according to the present invention.
Figure 27:
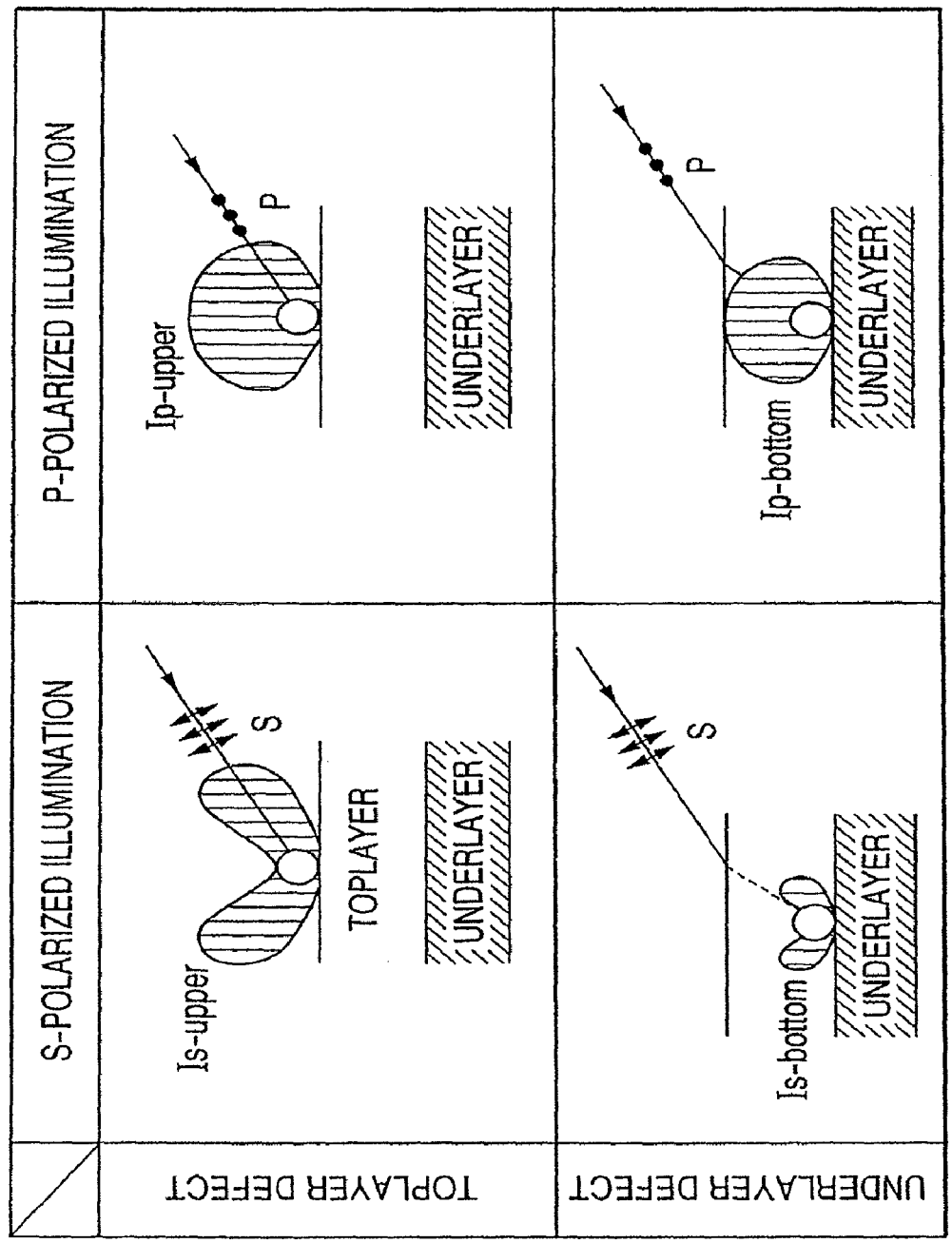
FIG. 27 is an explanatory diagram indicating that the defects observed during S-polarized illumination and P-polarized illumination process steps according to the present invention can be classified into toplayer defects and underlayer defects.
Figure 28:
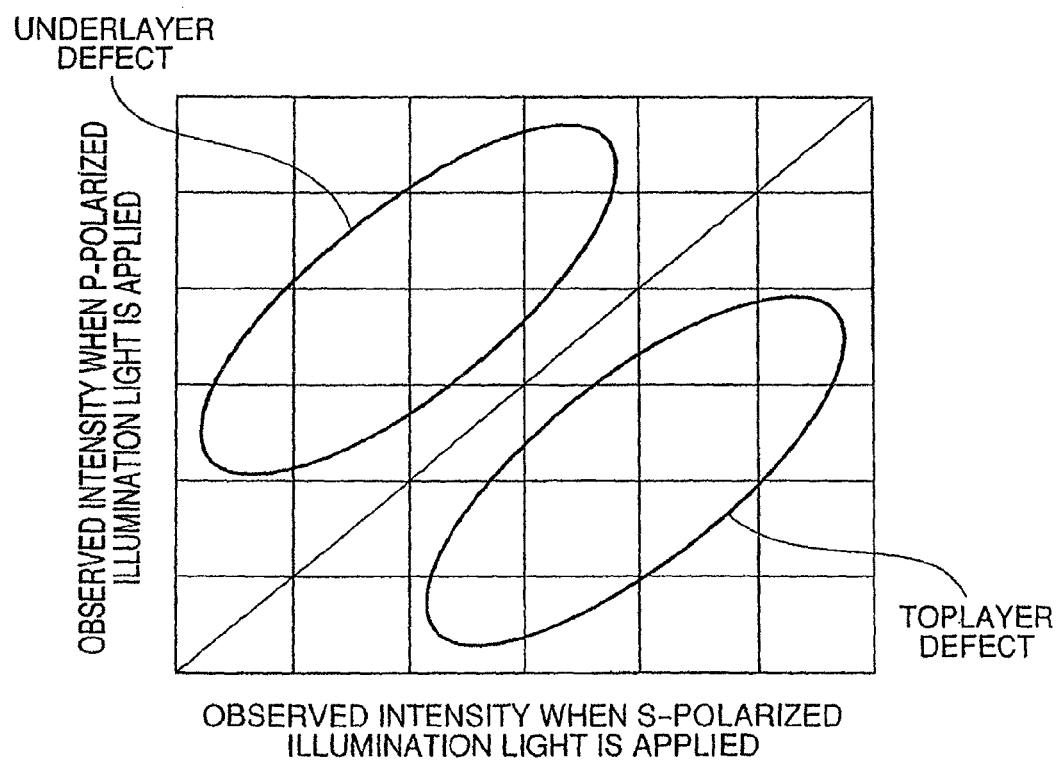
FIG. 28 is a diagram representing a relationship between P-polarized illumination and S-polarized illumination intensity levels for a toplayer defect and an underlayer defect.

34. FIG. 26 shows relationships between irradiation angle (elevation α, β) to and transmittance for S-polarization and P-polarization with respect to a transparent film formed on the wafer. When compared assuming that the elevation angles α, β are about 5 to 15 degrees, P-polarization is high in transmittance, relative to S-polarization. This indicates that as shown in FIGS. 27 and 28, for detection of any contamination and other defects on the transparent film, S-polarization is superior because of a stronger signal being obtained during the detection, and for detection of any contamination and other defects on an underlayer of the transparent film, P-polarization is superior because of a stronger signal being obtained during the detection. Whether a particular defect is a top layer defect or an underlayer defect can be determined by, as shown in FIG. 28, conducting a comparison between a signal detected from the defect during S-polarized light illumination, and a signal detected from the defect during P-polarized light illumination.

During S-polarized irradiation of a slit-shaped beam 90 using the polarizing plate 23, S-polarized components are returned from the iterative pattern, whereas a mixture of S-polarized components and P-polarized components is returned from the defect such as contamination. Using the analyzer (polarizing filter) 34 to light-shield the S-polarized components, therefore, makes it possible for the image sensor 36 to receive the P-polarized components obtained from the defect such as contamination. Thus, a signal identifying the defect can be detected and the top layer defect can be detected with high sensitivity.

During P-polarized irradiation of the slit-shaped beam 90 via the polarizing plate 23, S-polarized components are returned from the iterative pattern, whereas a mixture of S-polarized components and P-polarized components is returned from the defect such as contamination. Using the analyzer (polarizing filter) 34 to light-shield the P-polarized components, therefore, makes it possible for the image sensor 36 to receive the S-polarized components obtained from the defect such as contamination. Thus, a signal identifying the defect can be detected and the underlayer defect can be detected with high sensitivity.

Next, the transport system 10 is described below. The stages 11, 12 move a sample placement table 14 along an XY plane and have a function that moves the entire wafer (inspection target substrate) 1 to an irradiation area of the irradiation optical system 20. The stage 13 is a Z-stage having a function which moves the sample placement table 14 in the optical-axis direction (Z-direction) of the detection optical system 30. The sample placement table 14 holds the wafer 1 and has a function that rotates the wafer 1 in a horizontal direction. The stage controller 15 has a function that controls the stages 11, 12, 13, and the sample placement table 14.

Figure 29A:
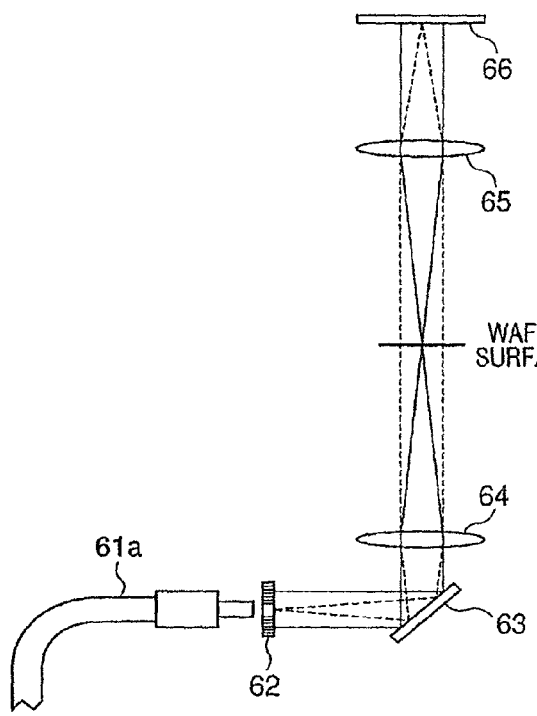
FIGS. 29A to 29C are diagrams showing an example of an in-focus control optical system according to the present invention.
Figure 29B:
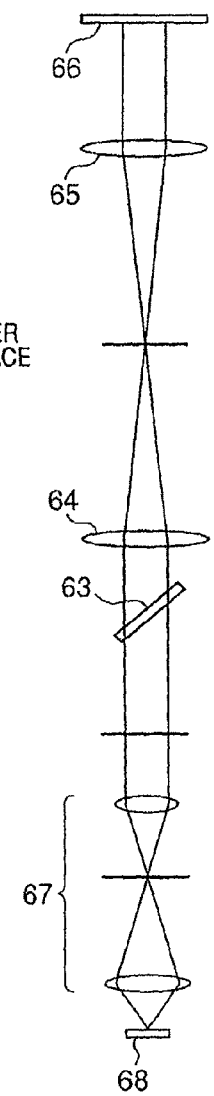
Figure 29C:
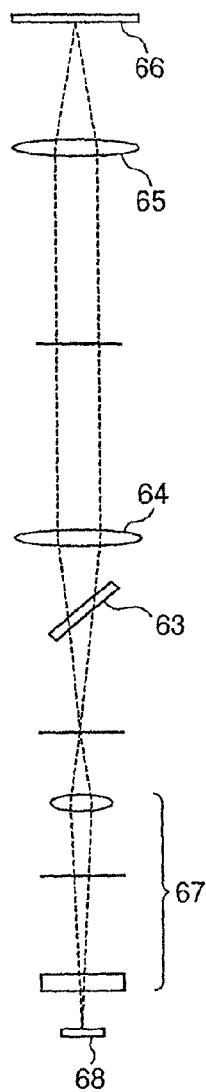
Figure 30:
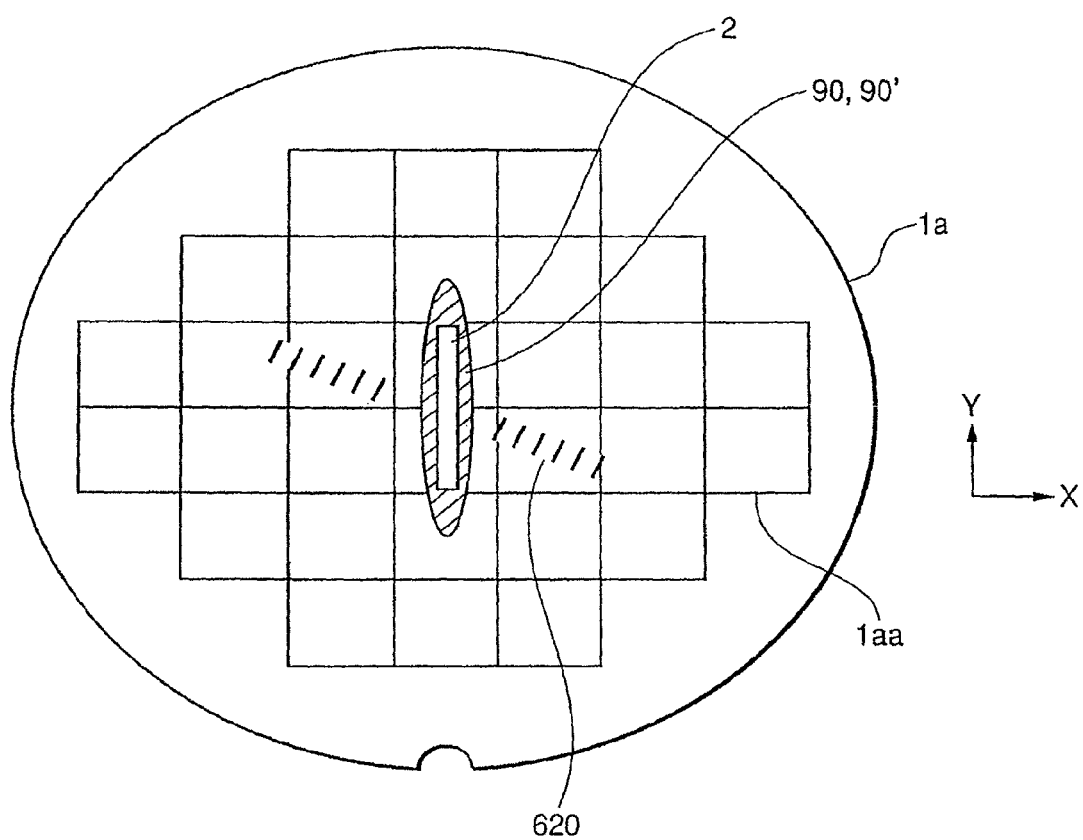
FIG. 30 is a diagram showing a relationship between a striped pattern projected onto the wafer according to the present invention, a slit-shaped beam, and a detection field.

Next, a more specific example of an in-focus control system 60 is described below using FIGS. 29A-29C and 30. FIG. 29A shows a projection optical path of a striped pattern 62, formed to extend from an optical fiber 61a for guiding the light emitted from the laser light source 61, to the mirror 66. FIGS. 29B and 29C show a reflection optical path extending from the mirror 66 to the linear sensor 68. FIG. 30 is a diagram representing a relationship between a striped pattern 620 projected onto the wafer "1a", and the slit-shaped beam 90, 90' irradiated. The striped pattern 620 is projected X-axially across the slit-shaped beam 90, 90'. In this way, the in-focus control system 60 is constructed such that: a striped regular reflection pattern of the striped pattern 620 which has been projected onto the surface of the wafer "1a" is imaged on the mirror 66 by the imaging lens 65; the striped regular reflection pattern that has thus been imaged is reflected by the mirror 66, then projected onto the surface of the wafer "1a" once again, and re-imaged by the imaging lens 67; and the striped regular reflection pattern that has thus been re-imaged is received as light by the linear sensor 68, from which a signal appropriate for a particular out-of-focus state on the wafer surface is output.

Autofocusing can therefore be realized by, for example, controlling the Z-stage 13 in accordance with the signal obtained from the linear sensor 68 according to the out-of-focus state.

Figure 31:
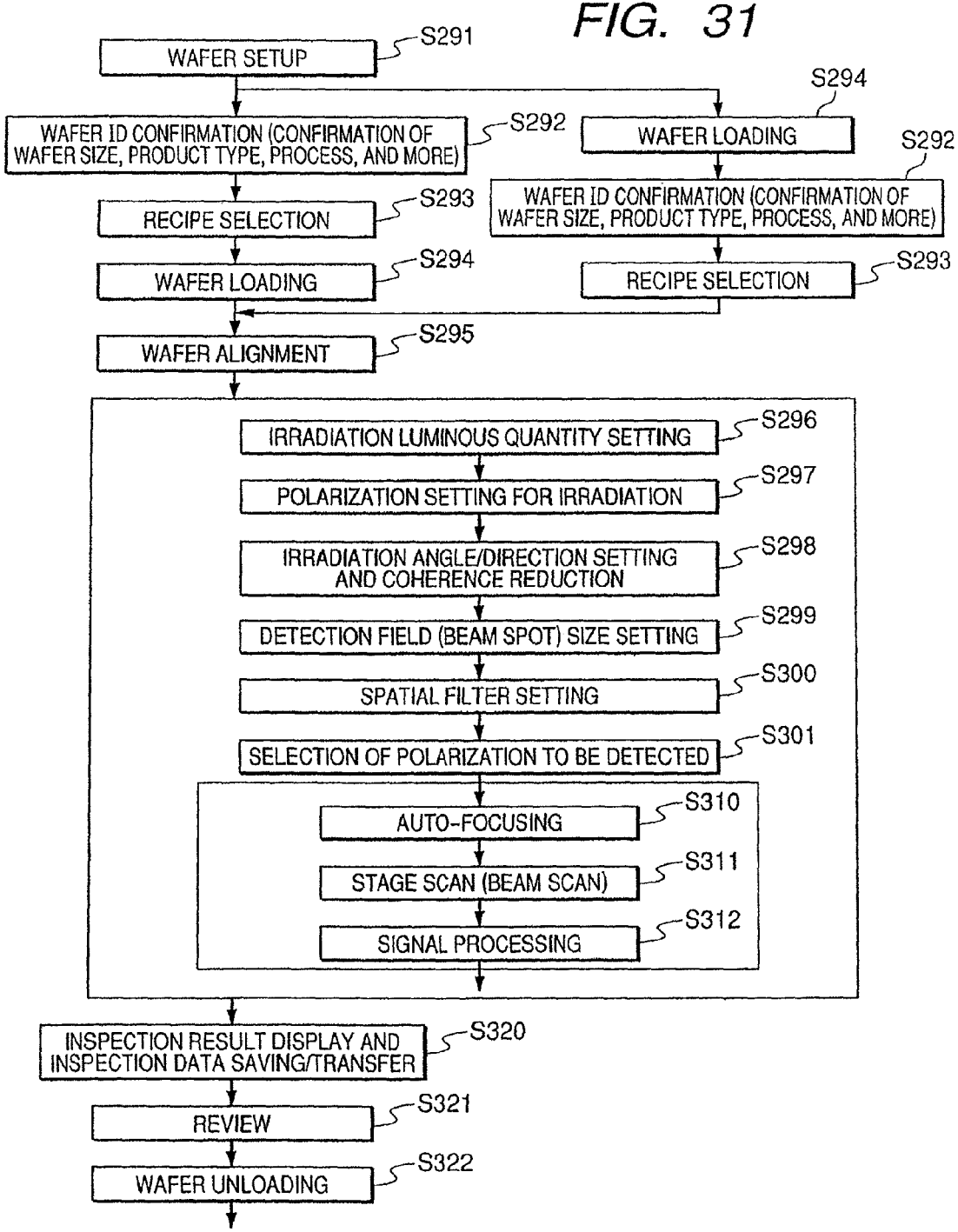
FIG. 31 is a diagram showing an example of a processing sequence of defect inspection according to the present invention.

Next, an example of a process sequence of inspecting defects such as contamination is described below using FIG. 31. First, a wafer cassette (such as SMIF) housing a plurality of wafers is set up automatically or manually in step S291. After this, a wafer ID is confirmed in step S292. The wafer ID is unique from which the wafer size, product type, process name, and other factors of the wafers can be identified. The wafer ID is entered from a database of, for example, a manufacturing line management system, into the total controller 70 via the input device 71. Next, in step S293, the total controller 70 examines the entered wafer ID and selects appropriate inspection parameters (recipe) stored within the storage unit 73. Next, the wafers are loaded onto the stages 11-14 of the apparatus in step S294. For a product having a wafer ID marked on the wafers themselves, a wafer is loaded in step S294, and the wafer ID is detected in step S292 during the loading and then a recipe is selected in step S293.

The above is followed by step S295, in which, while the stages 11-14 are being moved, a position of an alignment mark formed on the wafer is detected using wafer alignment optics (not shown) and the detected position is matched to a reference position to perform the wafer alignment.

Next, the process proceeds to the inspection of defects such as contamination. During the defect inspection, the total controller 70 conducts the following setting steps in accordance with a required recipe among a plurality of recipes provided in advance. That is to say, as described in JP Kokai No. 2000-105203, the total controller 70 first sets a wafer irradiation luminous quantity appropriate for the luminous quantity adjusting filter (luminous attenuation filter) 22, in step S296 in accordance with contamination detection sensitivity. Next, in step S297, depending on whether top layer or underlayer defects are to be detected, the total controller 70 sets the appropriate kind of polarized light to be irradiated onto the wafer via the polarizing plate 23, as described in FIGS. 27 and 28. In step S298, the total controller 70 sets the wafer irradiation angle α, β based on selection of the switchable inclined mirror 2604, 2624. In step S298, the total controller 70 also sets any one of the three irradiation optical systems 200a-200c to determine a direction of irradiation. In step S298, the total controller 70 also sets whether the coherency reduction optical system 255 is to be used. In step S299, the total controller 70 sets the size of the detection field 210 (longitudinal width of the rectangular light-receiving surface of the TDI sensor 36), that is determined by the beam width (equivalent to a 13.5% illuminance) of the beam expanded by a diaphragm (not shown) or the beam-expanding optics 24 or the like, as shown in FIG. 14. In step S300, the total controller 70 sets a light-shielding pattern of a spatial filter 32, corresponding to the particular pattern region P1, P2, P3 in the chips. In step S301, the total controller 70 sets either P-polarization or S-polarization for the analyzer (polarizing filter) 34 to fit the above-selected kind of polarized light to be used for wafer irradiation. In addition, if the detection optical system 30 is constructed such that its detection magnification is variable, the total controller 70 sets the detection magnification. In this manner, the irradiation parameters and detection parameters based on the wafer ID are set up as a recipe for the irradiation optical system 20 and the detection optical system 30.

After this, defects are actually inspected. As shown in FIG. 30, while the in-focus control system 60 is conducting auto-focusing on the wafer top layer in step S310, the wafer "1*a*" is irradiated with the slit-shaped beam 90, 90', the stage system is caused to travel for X-axial movement of the wafer, and an image of the detection field 210 is acquired by the image sensor 36 constructed using a TDI sensor, in step S311. In step S312, defects such as contamination are extracted by the image processor 40 through signal processing concurrent with auto-focusing and stage traveling.

When the defect inspection is completed, the total controller 70 conducts step S320 to display inspection results on a monitor 72, save inspection data in the storage unit 73, and transfer the data to a server and/or the like. After that, the total controller conducts step S321, as required, to review the contamination and other defects through the reviewing optical microscope 80, and then conducts step S322 to unload the wafer. This completes the successive inspection sequence.

Figure 32:
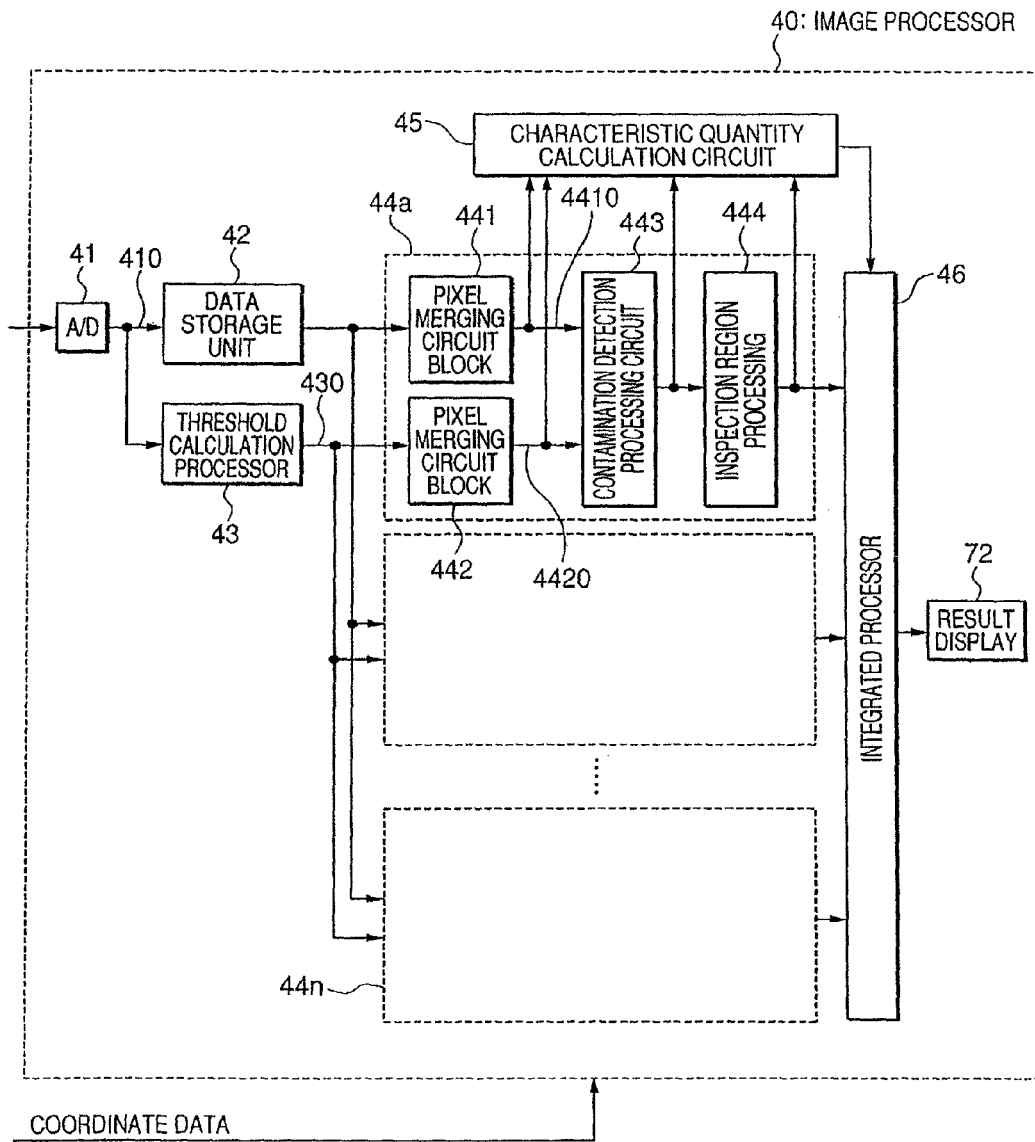
FIG. 32 is a schematic configuration diagram showing an example of an image processor in the present invention.

Next, a more specific example of an image processor 40 is described below using FIG. 32. This specific example of the image processor 40 is briefly described here since the example is already described in JP Kokai No. 2004-177284. The image processor 40 includes: an ND converter 41; a data storage unit 42 for storing an ND converted detection image signal "f(i, j)"; a threshold calculation processor 43 for calculating threshold levels from the detection image signal; contamination detection processors 44*a*-44*n* for conducting contamination detection processing for each pixel-merging operation, based on the detection image signal obtained from the data storage unit 42 and the threshold image signals [Th (h), Th (Hm), Th (Lm), Th (L)] 430 obtained from the threshold calculation processor 43; a feature calculating circuit 45 for calculating features such as the amount of scattered light that has been obtained from defect detection during low-angle illumination, the amount of scattered light that has been obtained from defect detection during high-angle illumination, and a detected pixel quantity indicating a spread of the defect; an integrated processor 46 that classifies on-semiconductor-wafer small/large contamination, pattern defects, micro-scratches, and other defects into various types of defects on the basis of the features obtained from the feature calculating circuit 45 during each merging operation; and a result display unit 72.

The contamination detection processors 44*a*-44*n* are associated with, for example, merge operators of 1×1, 3×3, 5×5, etc. up to n×n, and respectively include pixel-merging circuit blocks 441*a*-441*n*, 442*a*-442*n*, contamination detection processing circuits 443*a*-443*n*, and inspection region processors 444*a*-444*n*.

The present invention is characterized particularly by the contamination detection processors 44*a*-44*n*, the feature calculating circuit 45, and the integrated processor 46.

Next, the operation is described below. First, a contamination signal that has been obtained using the image sensor 36 is digitalized with the A/D converter 41. The thus-obtained detection image signal "f(i, j)" 410 is saved in the data storage unit 42 and sent to the threshold calculation processor 43. The threshold calculation processor 43 calculates a threshold image signal "Th (i, j)" 430, and in accordance with a signal that has undergone processing with the pixel-merging circuit 441, 442, the contamination detection processor 443 detects contamination for each merge operator. The inspection region processor 444 processes both the detected contamination signal and the threshold image signal with appropriate processing according to a location at which the contamination has been detected. At the same time, in accordance with the signals obtained from the pixel-merging circuit blocks 441*a*-441*n*, 442*a*-442*n*, contamination detection processing circuits 443*a*-443*n*, and inspection region processors 444*a*-444*n* of the contamination detection processors 44*a*-44*n* provided for each merge operator, the feature calculating circuit 45 calculates features such as the amount of scattered light obtained during low-angle irradiation (medium-angle irradiation included), the amount of scattered light obtained during high-angle irradiation, and the number of pixels detected on the defect. The above contamination signal and the above features are integrated by the integrated processor 46, and inspection results are displayed on the result display unit 72.

Figure 33:
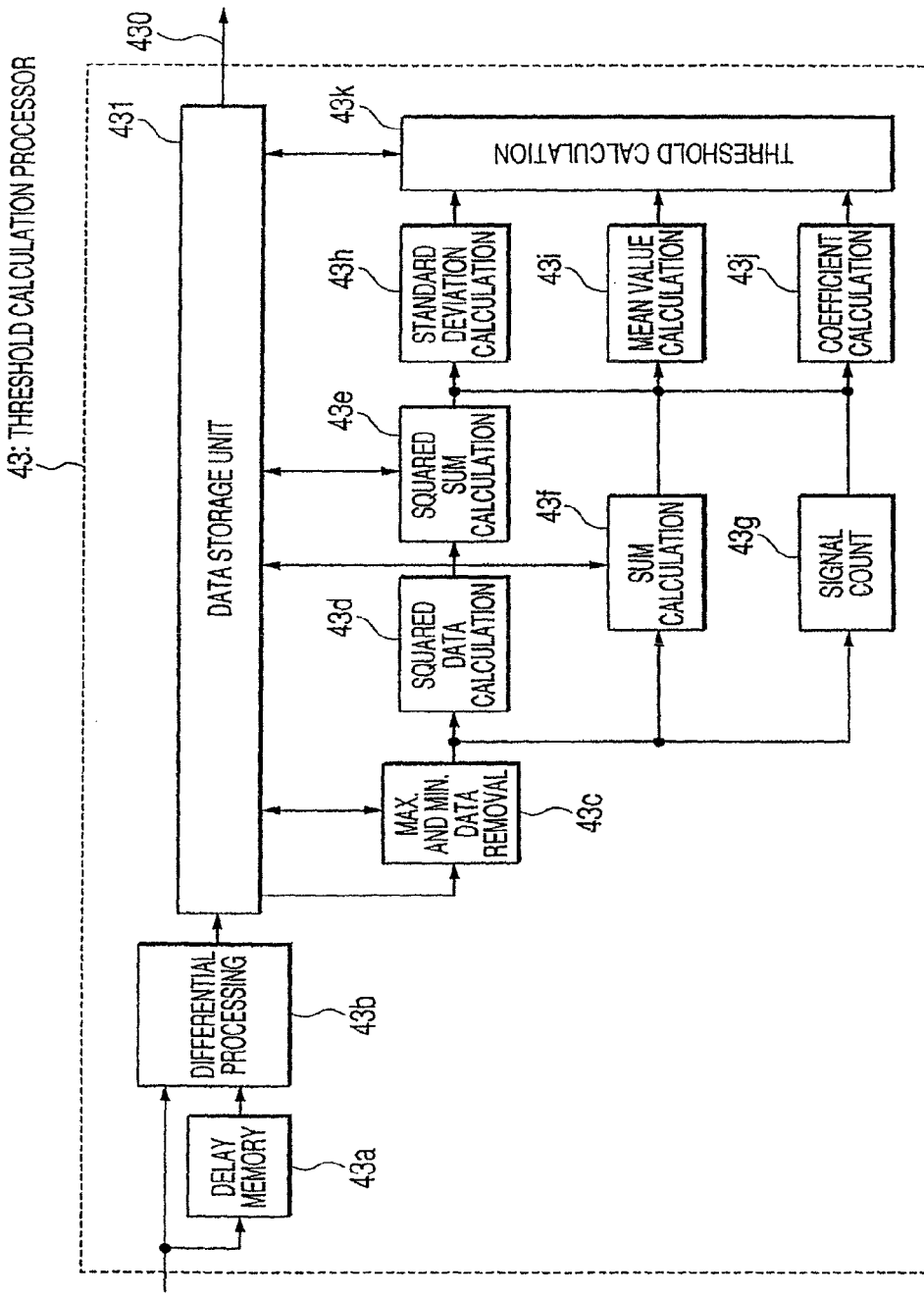
FIG. 33 is a configuration diagram showing an example of a threshold level calculation processor in the present invention.

The details are described below. The ND converter 41 is a circuit having a function that converts the analog signal that has been obtained by the image sensor 36, into a digital signal. The number of bits into which the analog signal is to be converted is desirably from about 8 to about 12. This is because there are the disadvantages that whereas conversion into a smaller number of bits results in lower resolution of signal processing and thus makes it more difficult to detect weak light, conversion into a larger number of bits makes the ND converter more expensive, resulting in increased device price. The data storage unit 42 is a circuit for storage of the digital signal that has been obtained from the A/D conversion. Next, the threshold calculation processor 43 will be described using FIG. 33. FIG. 33 is a diagram showing an example of the threshold calculation processor 43 described in JP Kokai No. 2000-105203. The threshold calculation processor 43 includes a delay circuit block 43*a* that creates a reference image signal "g(i, j)", a differential processing circuit block 43*b* that calculates a differential signal "ΔS(i, j)" between the detection image signal "f(i, j)" and the reference image signal "g(i, j)", a maximum/minimum data remover 43*c*, a squared data calculator 43*d* that calculates a squared value of the differential signal, a squared data sum calculator 43*e* that calculates a sum of the squared values, a signal sum calculator 43*f* that calculates a differential signal sum, a counter 43*g* that counts input signals, a standard deviation calculator 43*h* that calculates standard deviations, a mean value calculator 43*i* that calculates an average value, a coefficient calculator 43*j* that calculates a coefficient (n) based on the number of input signals that has been counted by the counter 43*g*, a threshold calculator 43*k* that calculates the image "Th(i, j)" 430 of threshold levels [Th(H), Th(L)], and a data storage unit 431.

Next, the operation is described below. The detection image signal "f(i, j)" that has been obtained by the ND converter 41 is input to the delay circuit block (delay memory block) 43*a* and the differential processing circuit block 43*b*, in which the input signal is then converted into the differential signal "ΔS(i, j)". For chip comparison, "(i, j)" denotes internal pixel coordinates of the chips. The delay circuit block 43*a* creates the reference image signal "g(i, j)" by delaying the input signal according to a particular iteration pitch of a circuit pattern present on the substrate under inspection. The delay circuit block 43*a* is only required to be a circuit that delays signal data for on-wafer chip. The amount of the signal data processed in this circuit block, however, does not always need to be equivalent to data for one chip, and the delay circuit block may function properly according to inspection target. That is to say, for a wafer having an iterative pattern in units of multiple chips, the delay circuit block may be required only to delay signal data for the multiple chips. Alternatively, for a DRAM product with an iterative pattern in chips, the delay circuit block may be required only to delay signal data according to the particular amount of iteration. The amount of signal delays can be modified under CPU instructions or the like.

The differential signal "$\Delta S(i, j)$" that has been processed in the differential processing circuit block 43b is next stored into the data storage unit 431. The squared data calculator 43d calculates a squared value ($\Delta S^2$) of the differential signal "$\Delta S$", and the squared data sum calculator 43e calculates a squared data sum ($\Sigma \Delta S^2$) of the differential signal "$\Delta S$". The sum calculator 43f calculates a sum ($\Sigma \Delta S$) of the differential signal "$\Delta S$". The counter 43g calculates a value denoting the number of input signals, "n". The maximum/minimum data remover 43c has a function that calculates maximum and minimum values from multiple sets of input data and then removes the maximum and minimum values from the multiple sets of input data. The standard deviation calculator 43h uses the above-processed calculation results to calculate a standard deviation [$\rho(\Delta S)=\sqrt{(\Sigma \Delta S^2/n - \Sigma \Delta S^2/n)}$] of the input data, and the mean value calculator 43i calculates a mean value [$\mu(\Delta S)=\Sigma \Delta S^2/n$]. Furthermore, the coefficient calculator 43j calculates coefficients (magnifications) "k" for setting the threshold levels associated with the number of sets of input data, "n".

The threshold calculator 43h uses the above-described data to calculate the image "Th(i, j)" 430 of the threshold levels [Th(H), Th(L)]. The threshold levels [Th(H), Th(L)] are calculated using expression (1) below, where, the value that has been calculated by the mean value calculator 43j is $\mu(\Delta S)$, the value that has been calculated by the standard deviation calculator 43h is $\rho(\Delta S)$, the value that has been calculated or set by the coefficient calculator 43j is "k", and a coefficient for verification is "m" (m is smaller than 1).

$$Th(H)=\mu+k\times\rho \text{ or } Th(L)=\mu-k\times\rho \text{ or } Th(Hm)=m\times(\mu+k\times\rho) \text{ or } Th(Lm)=m\times(\mu-k\times\rho) \quad (1)$$

The threshold images {detection threshold levels [Th(H), Th(L)] and verification threshold levels [Th(Hm), Th(Lm)]} that have thus been calculated by the threshold calculator 43k may be stored into the data storage unit 431, from which the threshold images may then be output as threshold image data. In addition, the threshold image data may be modified for each region which has been set up from the inspection region processors 444a-444n. In short, a threshold level map can be created and stored in the data storage unit 431. Furthermore, for reduced detection sensitivity in a certain region, the threshold levels in the region may be enhanced.

Figure 34:
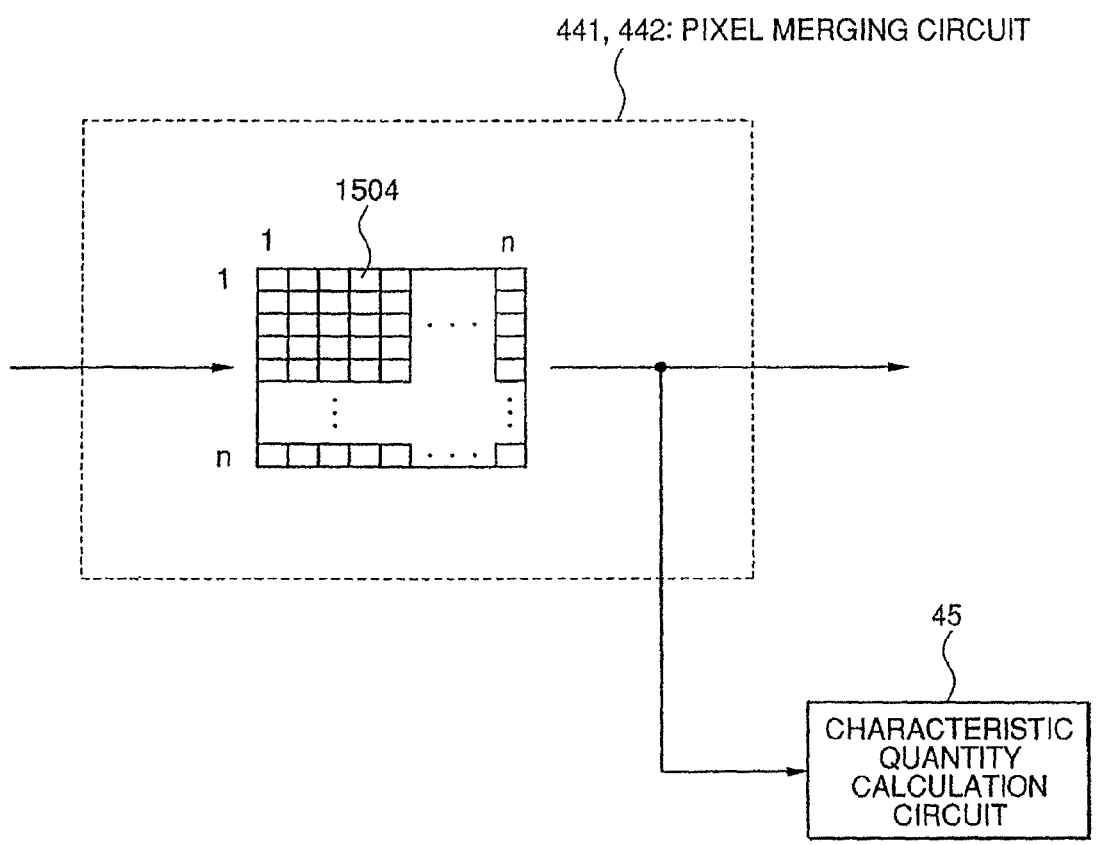
FIG. 34 is a configuration diagram showing an image-merging circuit in the present invention.

Next, signal pixel-merging circuit blocks 441, 442 are described below using FIG. 34. The pixel-merging circuits 441a-441n, 442a-442n each include a different merge operator 1504. The merge operator 1504 is a function that couples together in an "n×n" pixel range, the detection image signal "f(i, j)" 410 obtained from the data storage unit 431, and the detection threshold images "Th(H)", "Th(L)", and verification threshold images "Th(Hm)", "Th(Lm)", obtained from the threshold calculation processor 43. The merge operator 1504 is a circuit that outputs, for example, a mean value of "n×n" pixels. The pixel-merging circuit 441a, 442a includes a merge operator for merging in, for example, a "1×1" pixel format, the pixel-merging circuit 441b, 442b includes a merge operator for merging in, for example, a "3×3" pixel format, and the pixel-merging circuit 441c, 442c includes a merge operator for merging in, for example, a "5×5" pixel format. In this way, the pixel-merging circuit 441n, 442n includes a merge operator for merging in, for example, an "n×n" pixel format. Input signals 410 and 430 of the merge operator for "1×1" pixel merging is output without being changed.

Since each threshold image consists of four image signals [Th(H), Th(Hm), Th(Lm), Th(L)] as described above, four merge operators "Ops" are required in each pixel-merging circuit 442a-442n. Therefore, the detection image signal 410 is subjected to merging processing in various merge operators 1504 before being output as a merged detection image signal 4411a-4411n from each pixel-merging circuit 442a-442n. In the meantime, the four threshold image signals 430 [Th(H) (detection threshold level "a") 430(1), Th(Hm) (detection threshold level "a") 430(2), Th(Lm) (detection threshold level "b") 430(3), Th(L) (detection threshold level "b") 430(4)] are merged by merge operators "Op1"-"Opn" before being output as merged threshold image signals 4421a [4420a(1)-4420a(4) to 4420n (4420n(1)-4420n(4))] from the pixel-merging circuits 442a-442n, respectively. The merge operators in each pixel-merging circuit 442a-442n perform the same function.

A pixel-merging effect will be described here. In the defect inspection apparatus of the present invention, it is necessary to detect defects without overlooking not only microcontamination, but also large thin-film-like contamination spread over a range of several μm. However, since thin-film-like contamination does not always produce strong detection image signals, the detection image signals generated in one-pixel units may be too low in S/N ratio to prevent overlooking. If an average detection image signal level of defect sampling in one-pixel units is taken as S, and an average variation as σ/n, extracting pixels in "n×n" pixel units equivalent to a size of thin-film-like contamination and then conducting convolutional computations will result in a detection image signal level of $n^2 \times S$ and a variation (N) of n×σ. The S/N ratio obtained in this case, therefore, will be n×S/σ. Meanwhile, if thin-film-like contamination is detected in one-pixel units, the detection image signal level and variation obtained will be S and σ, respectively, and thus the S/N ratio obtained will be S/σ. Convolutional computation of the pixels extracted in "n×n" pixel units equivalent to the size of thin-film-like contamination, therefore, makes it possible to improve the S/N ratio by a factor of "n".

For contamination as small as about one pixel unit, the detection image signal level detected in one-pixel units is S and a variation is σ, so the S/N ratio obtained is S/σ. If pixels are extracted in "n×n" pixel units from an image of contamination as small as about one pixel unit and convolutionally computed, a detection image signal level of $S/n^2$ is obtained with a variation of n×σ, so the S/N ratio obtained is $S/n^3/\sigma$. For contamination as small as about one pixel unit, therefore, higher S/N ratios can be obtained by acquiring a signal in a pixel unit.

In addition, while the function of the merge operators described in the present embodiment has been described in the example of output of an "n×n" pixel mean value, the maximum and minimum values of "n×n" pixels or a median value thereof may be output instead. A stable signal is obtained if the median value is used. Furthermore, the output value may be a value obtained by multiplying or dividing the mean value of "n×n" pixels by a specific value.

Figure 35:
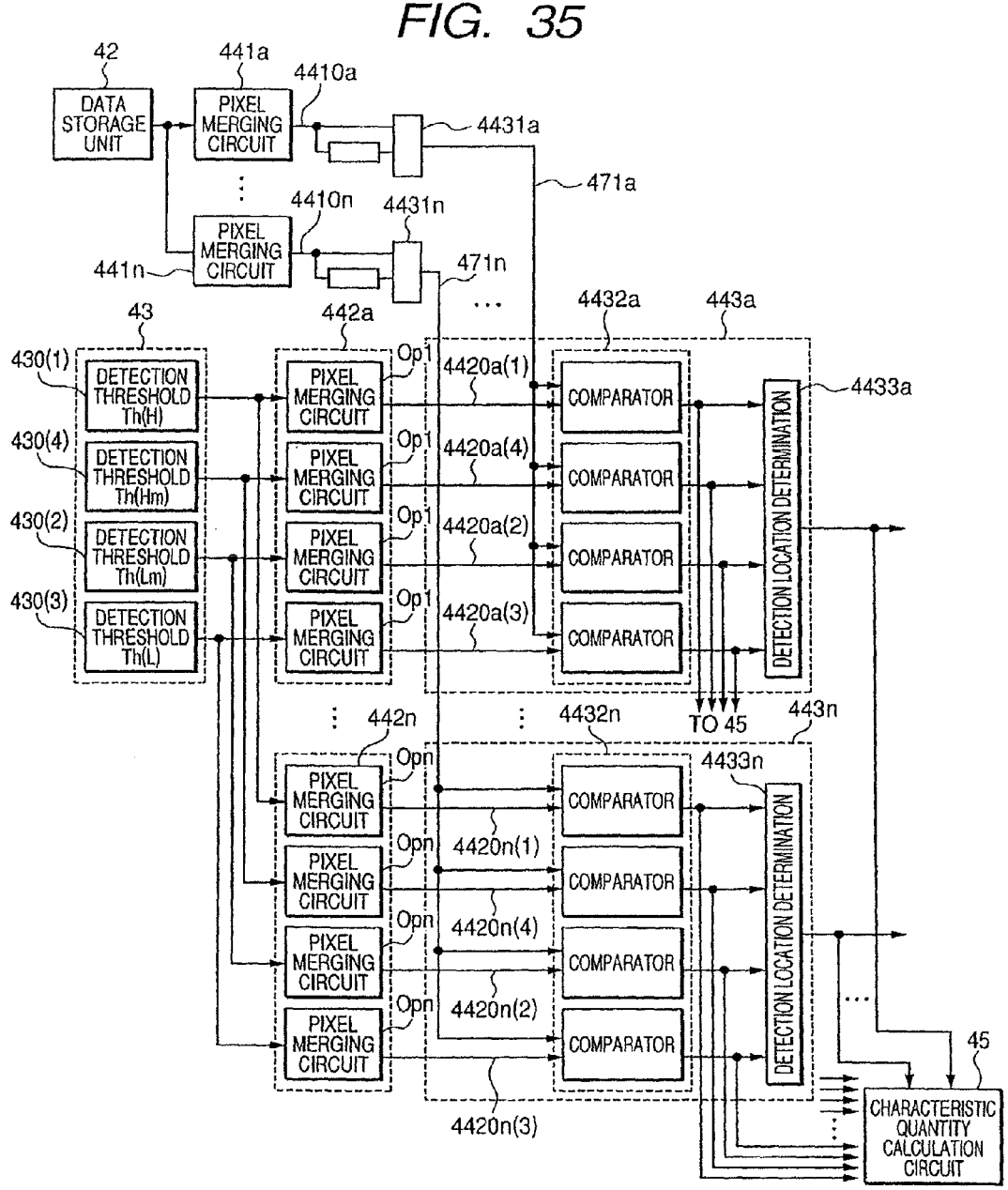
FIG. 35 is a configuration diagram showing a contamination detection processor in the present invention.

Next, a more specific example of the contamination detection processor 443 is described below using FIG. 35. FIG. 35 shows the pixel-merging circuit blocks 441a and 442a for merging in a "1×1" pixel format, and the pixel-merging circuit blocks 441n and 442n for merging in an "n×n" pixel format. The contamination detection processing circuits 443a-443n are associated with the respective merge operators and respectively include: comparators 4432a-4432n for conducting comparisons in magnitude between each of merged differential signals 471a-471n obtained from differential processing circuits 4431a-4431n, and each of merged threshold image signals 4420a(1)-4420a(4) to 4420n(1)-4420n(4); and detection locating processors 4433a-4433n for identifying a detection location of contamination. Each comparator 4432a-4432n has: a delay memory to delay, in accordance with the iteration, for example, in accordance with the chip, the detection image signal obtained from the associated pixel-merging circuit 441a-441n; and a differential processing circuit 4431a-4431n to form a differential signal between the pixel-merged detection image signal 4410a-4410n and the reference image signal obtained from the pixel-merging process, which has been delayed by the delay memory. Therefore, the comparators 4432a-4432n perform comparisons between the merged threshold images "Th(H) (i, j)", "Th(Hm) (i, j)", "Th(Lm) (i, j)", and "Th(L) (i, j)" obtained from pixel-merging circuits M1-M4 of the pixel-merging circuit blocks 442a-442n. For example, if the merged differential detection signal 471a-471n is greater than the merged threshold image "Th(i, j)" in magnitude, each comparator 4432a-4432n functions to judge that contamination exists. In the present example, four kinds of threshold levels are provided and the comparator 4432a-4432n conducts a contamination judgment process on the merged threshold image 430(1)-430(4), for each merge operator. The detection locating process is performed by the detection locating processors 4433a-4433n to identify the chip in which the contamination or defect that has been detected during signal processing is present. This process is based on the concept that the results obtained during the detection with the detection thresholds [Th(H), Th(L)] for detecting contamination or defects, and with the verification thresholds [Th(Hm), Th(Lm)] that are smaller values than the detection thresholds, are used to identify the chip where the contamination or defect was detected.

Next, the inspection region processors 444a-444n are described below. Each inspection region processor 444a-444n is used to remove data of regions not requiring inspection (including in-chip region) from the contamination or defect detection signal obtained from the particular chip by the contamination detection processing circuits 443a-443n. Each of the inspection region processors 444a-444n is also used to change detection sensitivity for each region (including the in-chip region), and to select a region to be inspected. For the inspection region processors 444a-444n, if detection sensitivity is allowed to be reduced for a specific region on the substrate 1 to be inspected, the threshold levels for the region, obtained from the threshold calculator 43k of the threshold calculation processor 43, may be set to be higher, or among all contamination data output from the contamination detection processing circuits 443a-443n, only data of the contamination existing in regions to be inspected may be left, based on the coordinates of the contamination.

The region for which the detection sensitivity is allowed to be reduced refers to a region of low circuit pattern density on the inspection target substrate 1. An advantage obtained from reducing the detection sensitivity is that a detection quantity can be reduced efficiently. That is to say, a highly sensitive inspection apparatus may need to detect several tens of thousands of foreign substances. If this is the case, contamination that may exist in the regions having a circuit pattern(s) is of major interest, and taking the proper measures against the contamination of major interest is a shortcut leading to improvement of device manufacture in yield. If all regions on the inspection target substrate 1 are inspected with the same sensitivity, however, this causes the contamination of major interest and contamination of minor interest to be mixed, thus impeding easy extraction of the former contamination. For these reasons, on the basis of in-chip CAD information or threshold level map information, the inspection region processors 444a-444n can extract the contamination of major interest efficiently by reducing the detection sensitivity of circuit pattern-free regions which are not so influenced on yield. A method of extracting the contamination is not limited to changing the detection sensitivity. An alternative extraction method for the contamination of major interest may be based on the classification of contamination that will be described later herein, or based on contamination sizes.

Next, the integrated processor 46 and its inspection result display unit 72 are described below. The integrated processor 46 has functions that integrate the contamination detection results that were concurrently processed by the pixel-merging circuits 441, 442, integrate the contamination detection results and the feature data that was calculated by the feature calculating circuit 45, and send the contamination detection results and the feature calculation results to the result display unit 72. This inspection result integration process is desirably performed using, for example, a personal computer (PC) to facilitate to change contents of the process.

First, the feature calculating circuit 45 is described below. The features here mean the values that represent features of the detected contamination or defects, and the feature calculating circuit 45 is a processing circuit that calculates the features. Examples of the features include the amounts of reflected/diffracted light (scattered light) (Dh, Dl) from contamination or defects, obtained during high-angle illumination/overhead detection, low-angle illumination/overhead detection, and low-angle illumination/oblique detection, the number of detected pixels, shapes of the contamination detection regions, directions of principal axes of inertia, the detection location of the contamination on the wafer, the kind of underlayer circuit pattern, the detection threshold levels of the contamination, and so on.

Next, an example of darkfield classification (DFC) by the integrated processor 46 is described below. Since the contamination detection signals that underwent various pixel-merging processes are input to the integrated processor 46, this processor can classify contamination into "Large contamination", "Microcontamination", and "Contamination small in height", as shown in FIG. 36.

Figures 36, 37:
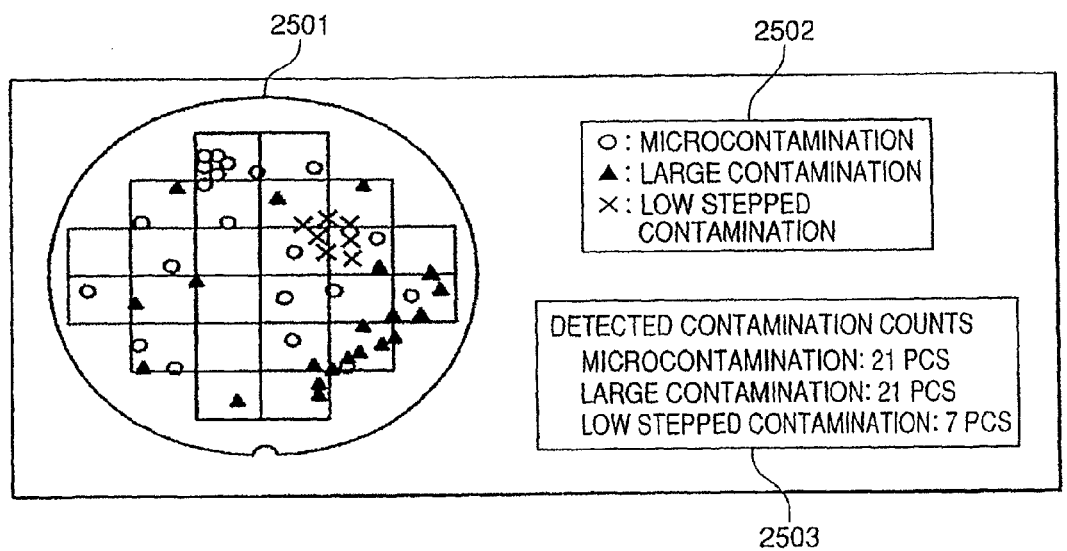
FIG. 36 is an explanatory diagram showing the kinds of contamination detected and undetected during image merging according to the present invention.
FIG. 37 is a diagram showing an example of displaying inspection results according to the present invention.

FIG. 37 shows an example of displaying the inspection results including the above classification results. The display of the inspection results consists of contamination position information 2501 obtained from the detection locating processors 4433a-4433n, category information 2502 on the classification results obtained from the integrated processor 46, and contamination counts 2503 for each category. In this example, the locations of all detected contamination and classification categories by notation symbols are displayed together as the contamination position information 2501. Details of each symbolically displayed classification categories are displayed as the classification results category information 2502. The contamination counts 2503 for each category denote the contamination counts that were classified into each category. There is the advantage that changing the display for each category in this way allows a user to readily confirm a distribution status of each kind of contamination.

Next, an example of a contamination size measuring method according to the present invention is described below. This method utilizes the fact that there is a proportional relationship between the contamination size and the luminous quantity detected by the image sensor 36. That is to say, both are maintained in the relationship that for small contamination, in particular, the luminous quantity detected, D, is proportional to the sixth power of contamination size G, subject to Mie scattering theory. In accordance with the detected luminous quantity D, the contamination size G, and a proportional coefficient "c", the feature calculating circuit 45 can measure the contamination size using expression (2) shown below, and supply measurement results to the integrated processor 46.

$$G = \epsilon \times D(1/6) \tag{2}$$

A value that has been calculated in advance from the luminous quantity detected from contamination of a known size is input as the proportional coefficient "ϵ".

The luminous quantity D detected from microcontamination is calculated by summing up pixel values of the contamination signal section. Calculation accuracy of the detected luminous quantity D can be improved by correcting a saturated portion of the contamination signal section by Gaussian distribution approximation. Although the present example uses the value of the signal sum of the contamination signal section as the detected luminous quantity, this value does not always need to be the signal sum and may be a maximum value of the contamination signal section instead. Using the maximum value yields an advantage in that an associated electrical circuit scale can be made smaller, and using the signal sum produces an advantage in that a signal-sampling error rate can be reduced for more stable results.

Figure 38:
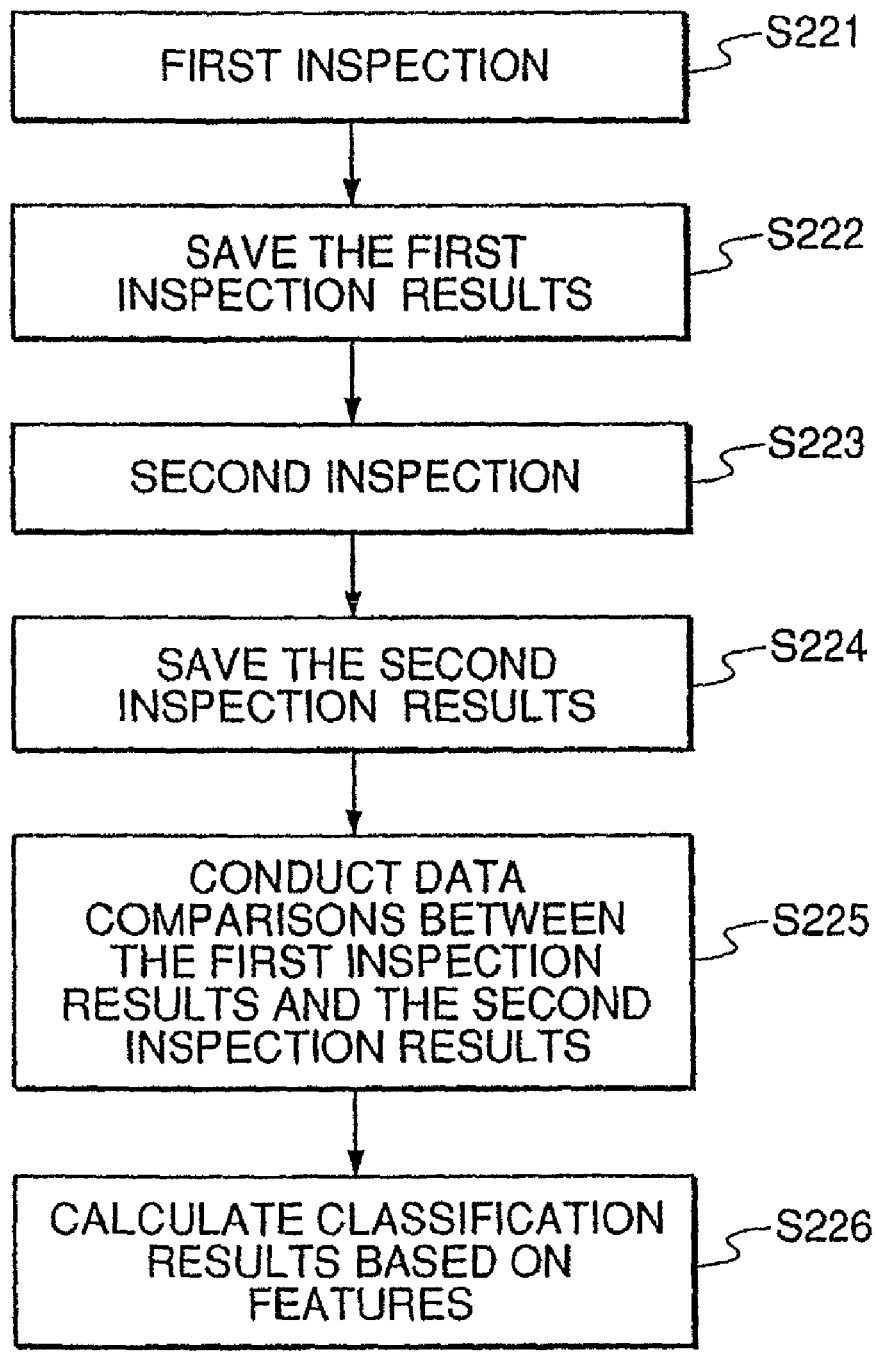
FIG. 38 is a diagram showing a contamination or defect classification sequence in a further example of the present invention.
Figure 39:
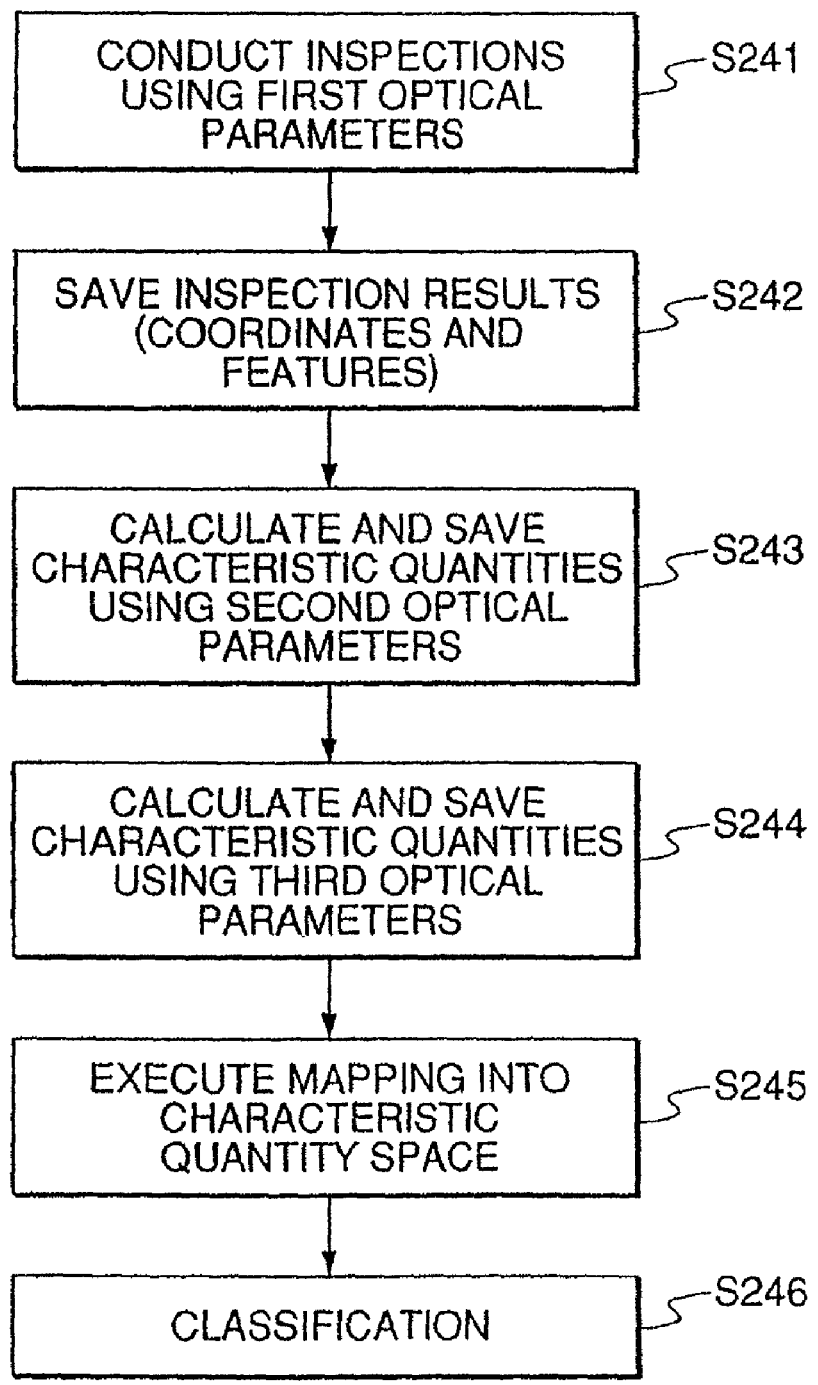
FIG. 39 is a diagram showing a contamination or defect classification sequence in a further example of the present invention.

Next, another example of contamination or defect classification by the integrated processor 46 is described below using FIGS. 38 and 39. FIG. 38 shows a sequence of classifying contamination on the basis of the results obtained during two inspecting operations by the integrated processor 46.

First, the wafer 1 is inspected using first inspection parameters in step S221. The coordinate data on various kinds of contamination, obtained from the contamination detection processing circuit 443 during the first inspection, and the features of each kind of contamination, obtained from the feature calculating circuit 45 during the first inspection, are saved in a storage unit (not shown) in step S222.

Next, in step S223, the wafer 1 is inspected using second inspection parameters different from the first ones. The coordinate data on various kinds of contamination, obtained from the contamination detection processing circuit 443 during the second inspection, and the features of each kind of contamination, obtained from the feature calculating circuit 45 during the second inspection, are saved in the storage unit (not shown) in step S222. For example, if the first inspection parameters are used for low-angle illumination, that is, for irradiating the wafer with illumination light from an angle close to the wafer surface, high-angle illumination parameters for irradiating the wafer with illumination light from an angle close to a normal line to the wafer surface are preferably selected as the second inspection parameters. In addition, when the wafer 1 is inspected using the second inspection parameters, the features at the coordinates where the contamination has been detected with the first inspection parameters are stored, regardless of whether some contamination is detected with the second inspection parameters.

Coordinate data that has been obtained from the first inspection results, and the coordinate data that has been obtained from the second inspection results are next compared in step S225. In step S226, if the two sets of coordinates are close to each other, the two pieces of contamination are regarded as identical contamination, and classified from the respective features. Here is an example of a method of judging the two sets of coordinate data to be close to each other: if the coordinate data obtained from the first inspection results is expressed as x1 and y1, and the coordinate data obtained from the second inspection results, as x2 and y2, and a comparison radius as "r", data falling under expression (3) below can be determined to be identical.

$$(x1-x2)^2 + (y1-y2)^2 < r^2 \tag{3}$$

where, "r" can be 0 or a value that allows for an error component inherent in the apparatus. This value can be measured by, for example, calculating a value of the left side of expression (3) for several sampling points of contamination coordinate data, then assigning associated mean value and standard deviation to expression (4), and assigning a value derived from expression (4), as "r".

$$r^2 = \text{Mean value} + 3 \times \text{Standard deviation} \tag{4}$$

While the present example has been described assuming that two inspecting operations are conducted, if increasing the number of kinds of features (such as a detected-pixel count equivalent to area Q of a defect) is likely to be effective for improving classification performance, inspection may be repeated at least three times to acquire the features of various kinds of contamination (detected-pixel counts).

Next, yet another example of contamination or defect classification by the inspection results integrated processor 46 is described below using FIG. 39. FIG. 39 shows a sequence of an example of conducting an inspection once and classifying detected contamination using the features calculated using three kinds of optical parameters. First, the wafer 1 is inspected using first optical parameters in step S241. Next, contamination coordinate data obtained from the contamination detection processing circuit 443, and contamination features obtained from the feature calculating circuit 45 are saved in step S242. The optical parameters that the defect inspection apparatus of the present invention adopts are modified after that. The optical parameters modified are, for example, an irradiation angle of the illumination optical system, an illumination direction thereof, and an overhead or oblique direction of detection with the detection optical system. In addition or alternatively, a magnification of the detection optical system may be changed or the optical filter to be used may be changed. The parameters to which such modifications or changes have been made are assigned as second optical parameters. After the optical parameters have been modified to the second optical parameters, step S243 is executed first to move the wafer 1 to the above-saved coordinate position of the contamination by means of the transport system 30. Next in step S243, detection with the image sensor 36 is conducted using the second optical parameters, and contamination's features are calculated from AD converted detection image signals by the feature calculating circuit 45. In step S244, operations similar to the above are further conducted to calculate features using third optical parameters. The first set of optical parameters, the second set of optical parameters, and the third set of optical parameters are desirably different from one another.

Figure 40:
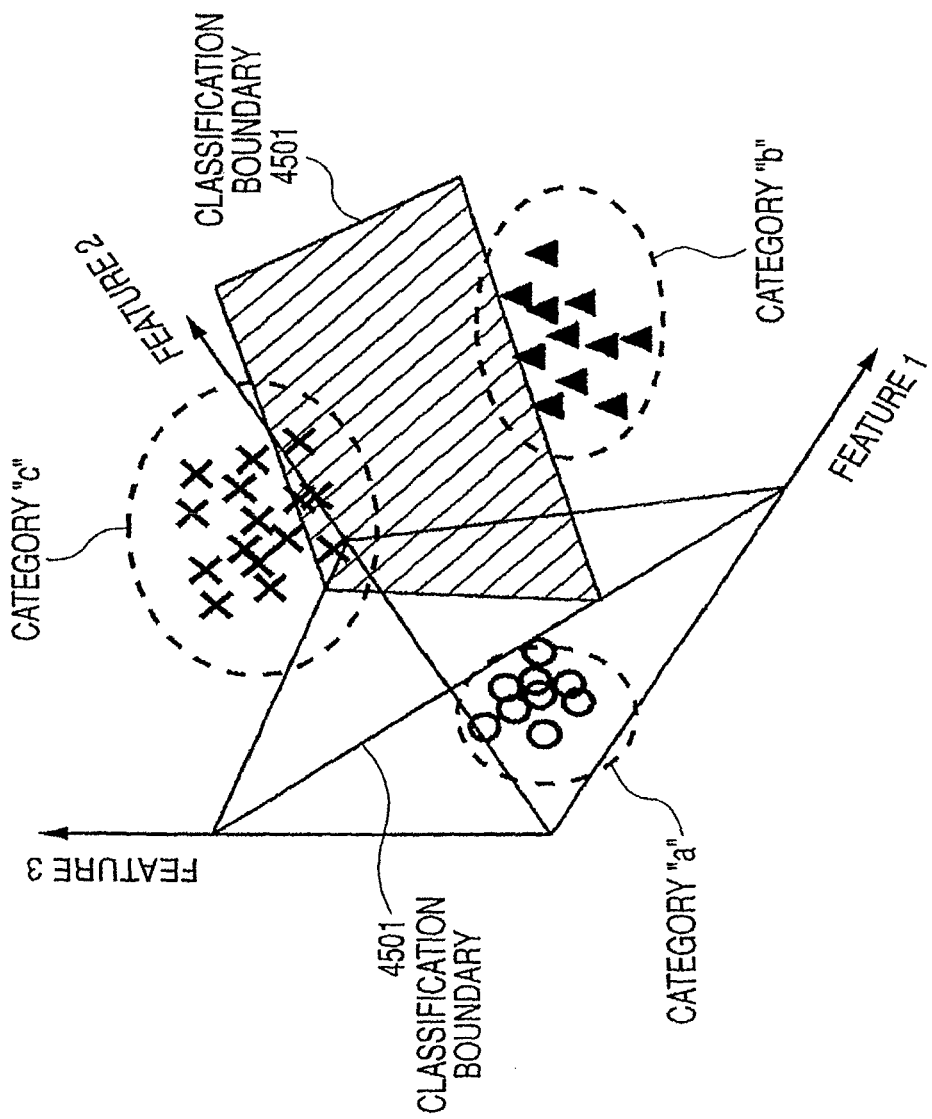
FIG. 40 is a diagram explaining a method of classifying contamination or defects from a plurality of kinds of their features according to the present invention.

Hereunder, concepts of classification methods are described using FIG. 40. FIG. 40 shows a features space in which three kinds of features are assigned to three axes. Details of the assignments to the three axes are as follows: for example, feature 1 is the defect's feature [e.g., amount of scattered light (Dh)] that has been acquired using the first optical parameters (e.g., for high-angle illumination), feature 2 is the defect's feature [e.g., amount of scattered light (Dl)] that has been acquired using the first optical parameters (e.g., for low-angle illumination), and feature 3 is the defect's feature (e.g., detected-pixel count equivalent to defect's planar area Q) that has been acquired using the third optical parameters (e.g., for a combination of high-angle illumination with the first optical parameters and low-angle illumination with the second optical parameters).

Classification boundaries (for total classification categories−1) are set in the features space. In FIG. 40, at least two classification boundaries suffice since an example of classifying defects into three kinds from three kinds of features is shown.

The defects can be classified into at least three categories (e.g., contamination defects, scratch defects, and circuit pattern defects) particularly by acquiring the amount of light scattered (Dh)] from the defect during high-angle illumination, the amount of light scattered (DI)] from the defect during low-angle illumination, and the number of pixels detected in the defect during the high-angle illumination and the low-angle illumination, as the three kinds of features. In this case, since the number of pixels detected in the defect (planar area Q of the defect) is acquired as a feature, contamination defects can be further categorized into large contamination and small contamination.

In addition, at least the sub-categorization of the contamination defects into large contamination defects and small ones becomes easy by acquiring three features, namely, the amount of light scattered from the defect at a high imaging magnification, the amount of light scattered from the defect at a low imaging magnification, and the number of pixels detected in the defect. Furthermore, classification of any microcontamination, scratches, and other defects that may exist on a transparent film becomes possible by acquiring features of a defect image obtained from a photodetector 640.

By the way, FIG. 40 shows an example in which classification boundaries 4501, 4502 are set. Here is how defects are classified in this example: first, the above-mentioned three features are plotted in the features space of FIG. 40, in step S245. Next, the contamination belonging to the regions divided by the classification boundaries 4501, 4502 is classified into category "a" (e.g., contamination defects), category "b" (e.g., scratch defects), and category "c" (e.g., circuit pattern defects), in step S246. In the example of FIG. 40, about 30 defects are classified into categories "a", "b", and "c", and a different notation symbol is assigned to each of the categorized defects. More specifically, the defects classified into category "a" (e.g., contamination defects) are marked as "○", the defects classified into category "b" (e.g., scratch defects) are marked as "▲", and the defects classified into category "c" (e.g., circuit pattern defects) are marked as "x".

It is also effective to display an isolation ratio, since a user can easily understand isolation performance. The isolation ratio here means, for example, a rate of the contamination that falls under one category and that is included in the regions isolated by an isolation boundary.

While the present example has been described assuming the use of the features calculated using three kinds of optical parameters, the number of kinds of optical parameters used does not always need to be limited to three and the present invention is applicable in cases where features can be calculated using multiple kinds of optical parameters, and where a plurality of features can be acquired using multiple kinds of optical parameters.

Figure 41:
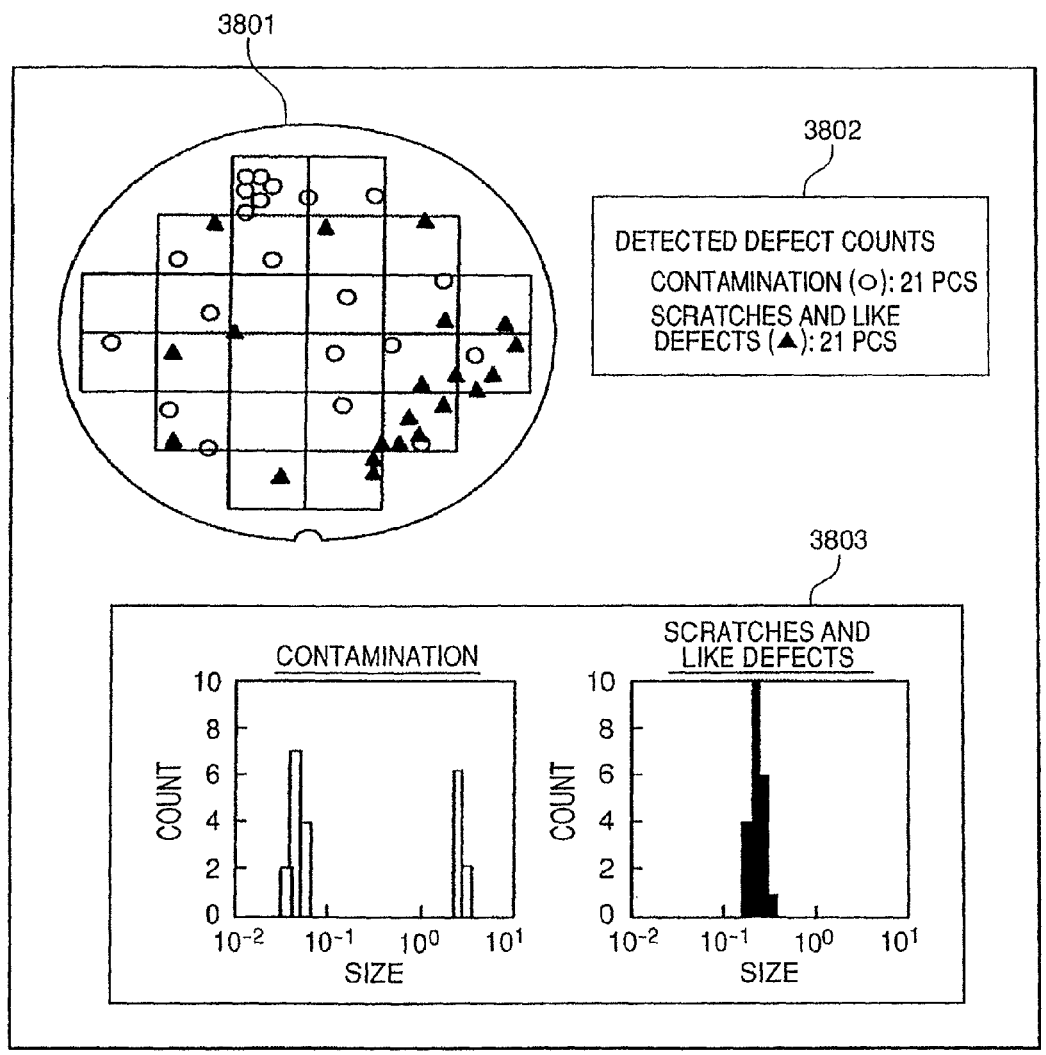
FIG. 41 is a diagram showing an example of displaying contamination or defect classification results and size measurement results together according to the present invention.

Next, a description is given below of another example in which the inspection results obtained from the image processor 40 are displayed on, for example, the display unit 72 by the total controller 70. FIG. 41 shows a display format consisting of position information 3801 on detected contamination or defects, detection counts 3802 of the contamination or defects, and histograms 3803 of the detected contamination or defect sizes. The present example shows the case scratches are detected as defects. The graphs 3803 are histograms of the sizes and detection counts of the contamination or scratches. Using this format to display the substances detected by the defect inspection apparatus of the present invention allows a distribution status of contamination or defects to be readily confirmed.

Figure 42:
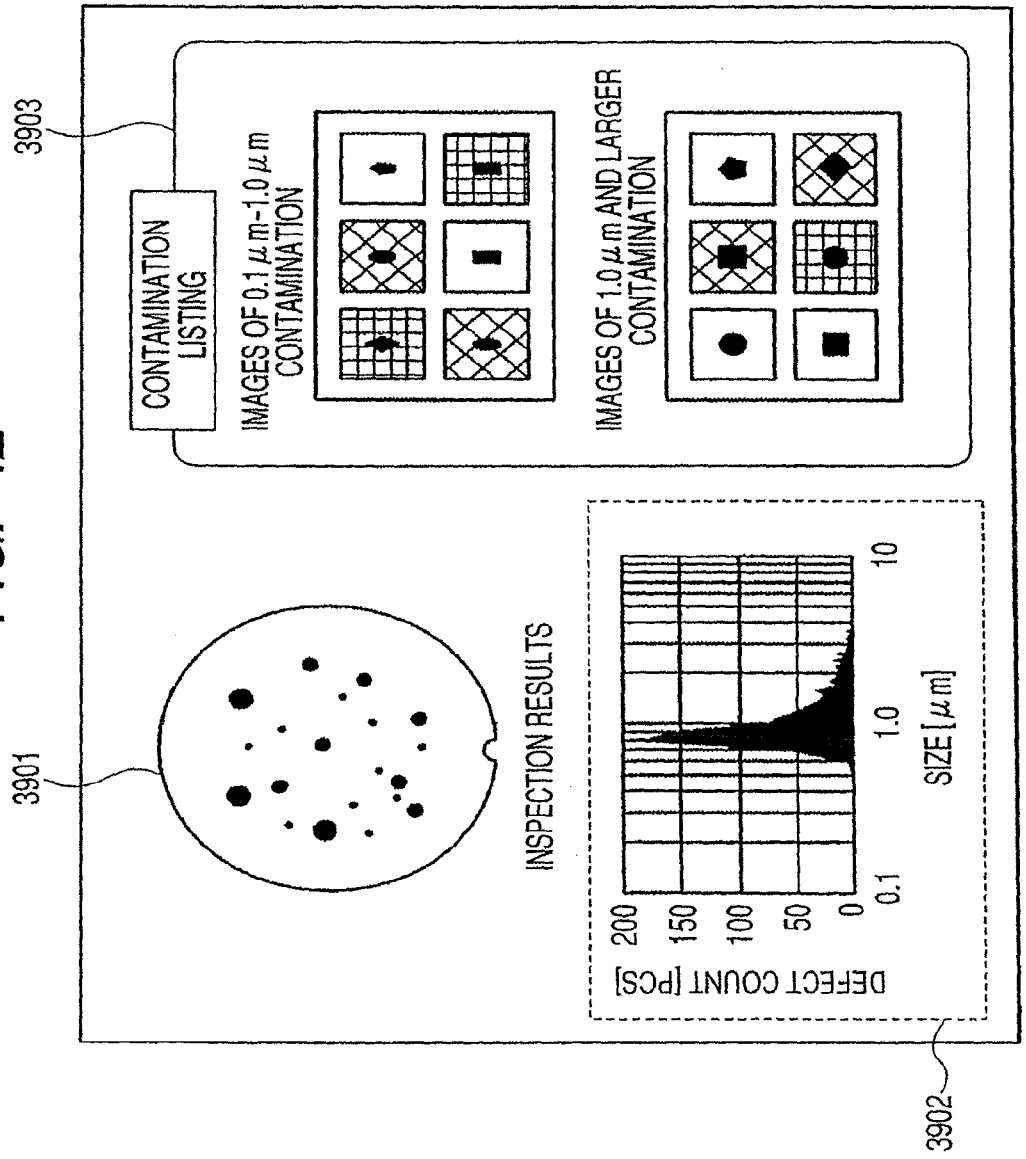
FIG. 42 is a diagram showing an example of displaying contamination or defect size measurement results and images of observed contamination or defects, according to the present invention.

FIG. 42 shows a display format consisting of an inspection map 3901 which shows detection positions of detected substances (contamination or defects), a histogram 3902 of sizes of the detected substances, and review images 3903 of the contamination. In the present example, all or part of the detected substances are displayed on the inspection map 3901 and the histogram 3902. Also, the review images 3903 are listed as review images of the substances which were sampled for each size from the detected substances. Six review images of the contamination measuring 0.1 μm or more and less than 1.0 μm in size, and six review images of the contamination measuring 1.0 μm or more are displayed in the present example. The review images 3903 here may be obtained using the reviewing optical microscope 80. Displaying the images that were acquired using laser light has the advantage that if the images are left in the storage unit 73 or the like during the inspection, the images can be displayed immediately after the inspection and thus the detected substances can be rapidly confirmed. During display of images to be acquired using the reviewing optical microscope 80, clear images can be obtained just by observing desired images in accordance with coordinates of the above-sampled substances after inspection, compared with laser light-acquired images. A higher-resolution microscope using an ultraviolet light source is desirable particularly for observing the contamination measuring less than 1.0 μm in size.

Alternatively, positions of the detected substances displayed as the review images 3903 may also be displayed on the inspection map 3901, or detection numbers of the detected substances may also be displayed on the review images 3903. In addition, while the present embodiment has been described assuming the display of six review images per set, the display format does not need to be limited to the display of six review images per set; all detected contamination or defects may be displayed or only a fixed rate of substances with respect to a detection count thereof may be displayed.

In a further alternative display format, the detected substances that have been classified into two kinds such as contamination and scratches may be displayed and their classification accuracy may also be displayed together.

Figure 43:
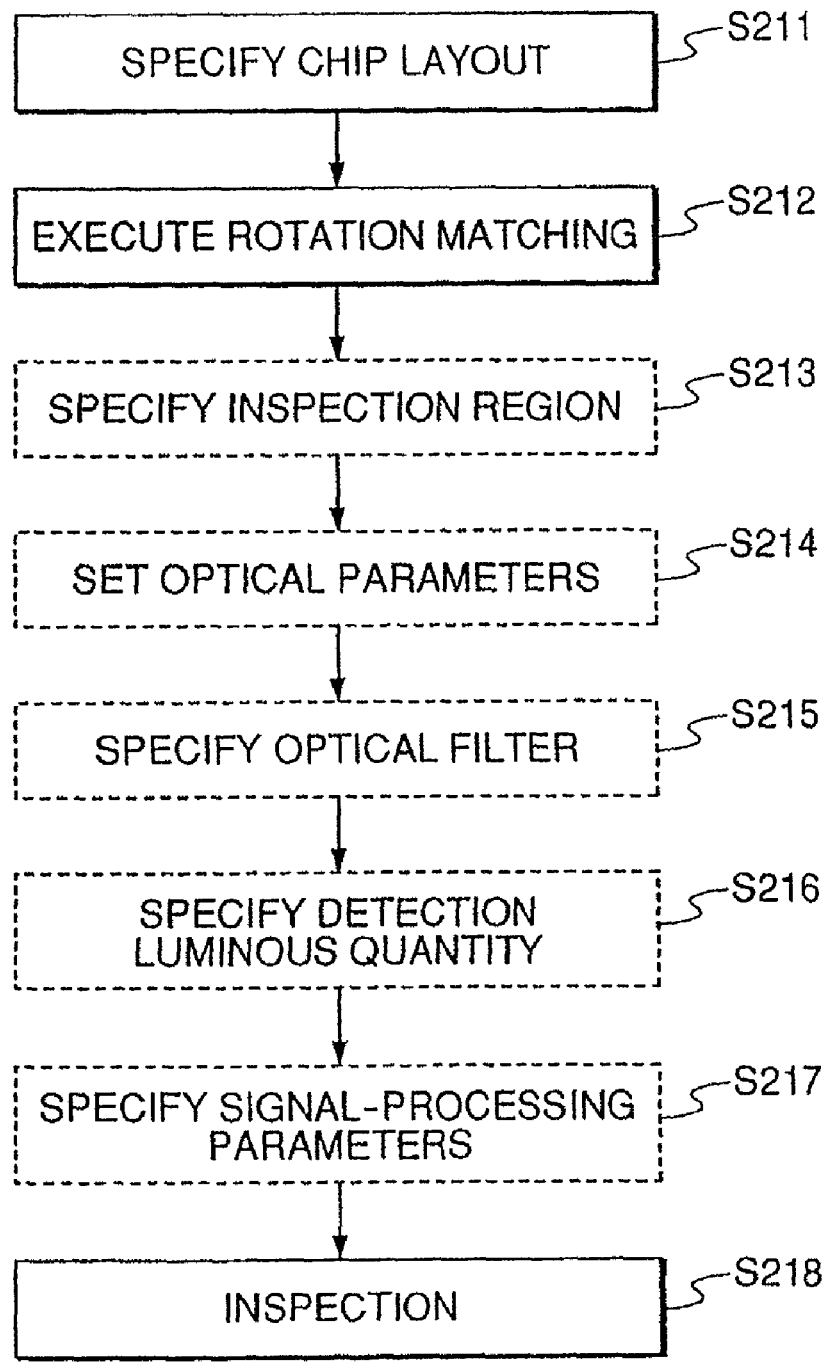
FIG. 43 is a diagram showing an inspection parameter setup sequence in the defect inspection apparatus according to the present invention.

Next, the inspection parameter (inspection recipe) setup and other processes performed in the total controller 70 and/or the like are described below using FIGS. 43 to 45. FIG. 43 is a diagram showing a process flow of the inspection parameter (inspection recipe) setup. First, the total controller 70 performs the inspection parameter (inspection recipe) setups before an inspection is executed. The inspection parameter setups include a chip layout setting step (S211) for the inspection target, a rotational matching step (S212) for the inspection target, an inspection region setting step (S213), an optical parameter setting step (S214), an optical filter setting step (S215), a luminous quantity detection setting step (S216), and a signal-processing parameter setting step (S217). Step S218 is an actual inspection.

Next, each setting step that the total controller 70 executes is described below. In the chip layout setting step (S211), chip sizes and whether a chip is present on the wafer are set to the image processor 40 and the like in accordance with CAD information and the like. The chip sizes must be specified since they corresponds to the distances required for comparative processing. Next, rotational matching (step S212) is executed to rotate the wafer 1 for its rotational shift of about "0". In other words, step S212 is executed to rotate the wafer 1 such that a layout direction of the chips on the wafer 1 rested on the stage which the total controller 70 causes the transport system 10 to control is adjusted to be parallel to the pixel direction in the image sensor 36. The execution of the rotational matching step arranges the iterative patterns on the wafer 1 uni-axially, hence making it possible to easily execute chip comparative signal processing. In the inspection region setting step (S213), desired inspection locations on the wafer where the inspection is to be executed, and detection sensitivity for each specified region are specified for the image processor 40 controlled by the total controller 70. Each region on the wafer can be inspected with optimal sensitivity by executing the inspection region setting step (S213).

In the optical parameter setting step (S214), an irradiation direction and irradiation angle of the wafer irradiation with the slit-shaped beam 90, 90', whether the coherency reduction optical system 230 is to be used, and a magnification of the detection optical system 30 are selected for the irradiation optical system 20 and detection optical system 30 controlled by the total controller 70. The above selections can be conducted in such an optical parameter setting window as shown in FIG. 44, for example. The optical parameter setting window includes an illumination direction parameter list 3001 for the illumination optical system, an illumination angle parameter list 3002 for the illumination optical system, and a detection optical parameter list 3003 (including an overhead/oblique detection direction) for the detection optical system.

Figure 44:
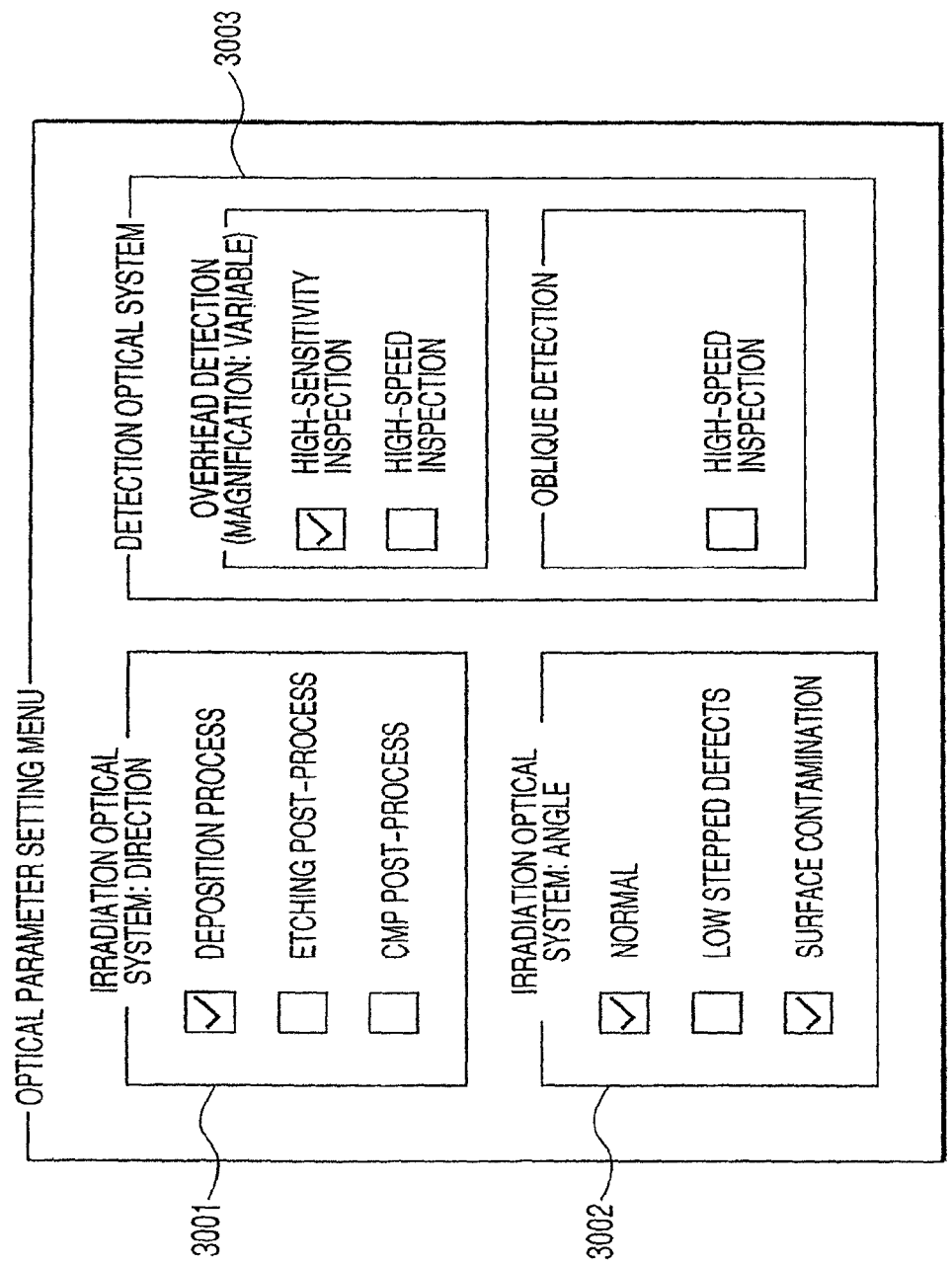
FIG. 44 is a diagram explaining an optical parameter setup menu according to the present invention.

FIG. 44 shows an example in which it is possible to select any of three parameters from the illumination direction parameter list 3001, select any of three parameters from the illumination angle parameter list 3002, and select any of two parameters from the detection optical parameter list 3003. A user of the defect inspection apparatus can select appropriate parameters from contents of the parameter lists 3001, 3002, 3003. For example, if the inspection target 1 is a wafer deposited with metallic films, highly sensitive inspection of the surface contamination existing on the wafer can be conducted by selecting "Deposition process" in the illumination direction parameter list 3001, selecting "Surface contamination" in the illumination angle parameter list 3002, and selecting "Overhead detection (Magnification: Variable): High-sensitivity inspection" in the detection optical parameter list 3003. This example is shown in FIG. 44. Highly sensitive inspection of the contamination, scratches, or other defects existing on oxide films of the wafer 1 can be conducted, for example, by selecting "CMP post-process" in the illumination direction parameter list 3001, selecting "Surface contamination" in the illumination angle parameter list 3002, and selecting "Oblique detection: High-speed inspection" in the detection optical parameter list 3003.

In the optical filter setting step (S215), whether the spatial filter 32 and polarizing filter 24b shown in FIG. 2 are to be used is set for the detection optical system 30 controlled by the total controller 70. Since the spatial filter 32 is a filter for shielding the light reflected/diffracted from the iterative patterns formed on the wafer, although the use of this filter should be set for a wafer having iterative patterns, the use of the filter does not need to be set for a wafer not having iterative patterns. The polarizing element 24b is effective for a wiring pattern whose edges were etched at nearly right angles.

In the luminous quantity detection setting step (S216), the amount of light entering the image sensor 36 is adjusted for the irradiation optical system 20 or detection optical system 30 controlled by the total controller 70. For the light reflected/scattered from the circuit patterns formed on the wafer, the component type of the light scattered differs according to the particular shape of the pattern. More specifically, for a flat wafer surface, scattered light does not occur so much and most of the light is regularly reflected light. For a very rough wafer surface, however, a great deal of scattered light occurs. In other words, the amount of light reflected/scattered from the circuit pattern varies according to the particular state of the wafer surface, that is, the kind of device-manufacturing process. However, since the image sensor 36 has its own dynamic range, adjustments are desirably conducted such that an appropriate amount of light according to the dynamic range will enter. For example, adjustments are desirably conducted such that the amount of light reflected/scattered from the circuit pattern on the wafer will be about 1/10 of the dynamic range of the image sensor 36. The amount of light entering the image sensor 36 may be adjusted by controlling an output luminous quantity with the luminous quantity adjusting filter 22 or by conducting adjustments with the ND filter 34.

The signal-processing parameter setting step (S217) is executed to set up the contamination/defect detection parameters that the total controller 70 causes the image processor 40 to control.

The user can perform inspections with desired parameters by starting the inspection process (step S218) after the above steps have been executed.

The parameters that have been described in the present example may be set up, for example, by manually entering data based on design information of the inspection target, by entering data with an input assist function accompanying the defect inspection apparatus of the present invention, or by acquiring information from a host system via a network.

Of all data settings of the parameters in the above-described setting steps, at least data settings of the parameters in inspection region setting step S213, optical parameter setting step S214, optical filter setting step S215, detection luminous quantity setting step S216, and signal-processing parameter setting step S217 do not always require modification for the particular inspection target and may remain fixed, irrespective of the kind of inspection target. Although maintaining fixed parameter settings leads to reduced inspection parameter setting time, each parameter is desirably tuned for higher sensitivity. In addition, inspection region setting step S213 does not always need to precede optical parameter setting step S214 and may be conducted in any phase before inspection process step S218 is conducted.

Figure 45:
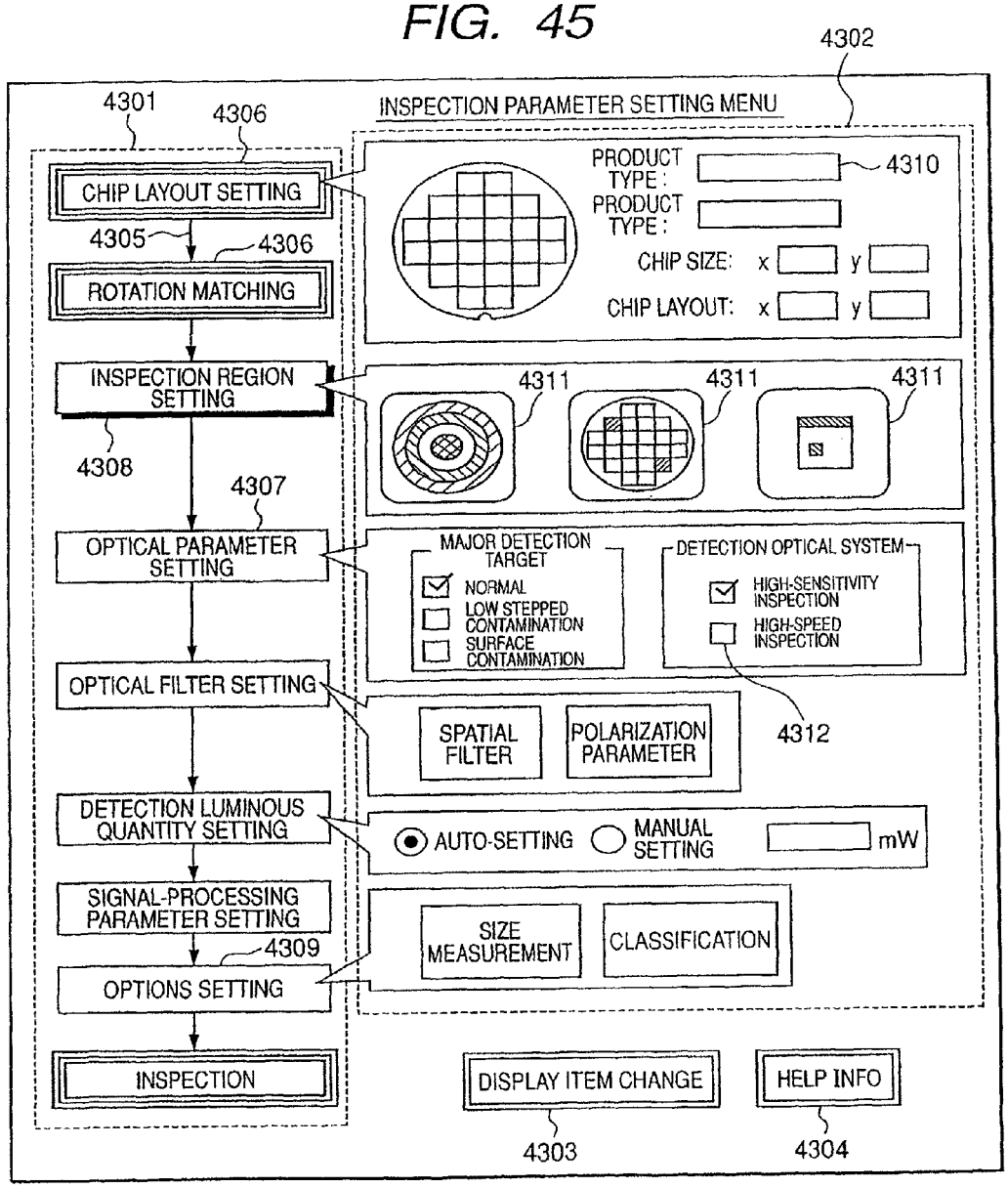
FIG. 45 is a diagram explaining an inspection parameter setup menu according to the present invention.

An example of a display screen menu for setting up the above-described parameters is shown in FIG. 45. This menu includes a parameter setting sequence diagram 4301, a detailed setup parameter list 4302, a settings display change button 4303, and a help information button 4304.

Next, details are described below. The parameter setting sequence diagram 4301 indicates a process flow of the inspection parameter setup in the defect inspection apparatus of the present invention. The user sets up parameters in order from "Chip layout setting" in accordance with the parameter setting sequence diagram.

A feature of the parameter setting sequence diagram 4301 is that since the process flow of the parameter setting is indicated by arrow 4305, the user can set each parameter most efficiently without making a mistake in the setting order. Another feature exists in that all items are divided into items that are necessary to be set (mandatory items) and items that are not necessary to be set (non-mandatory items). The latter items are those whose predefined values can be used. Since the display items are divided in this way, the user can understand the minimum setup items required. In addition, to obtain inspection results immediately, the user needs only to set up the mandatory items. Also, to tune detection sensitivity, the user needs only to set up parameters in the non-mandatory setup items. That is to say, parameter setup levels can be modified to fit particular needs of the user. For example, a button 4306 is displayed in a triple-frame format to indicate that the item is a mandatory one, and a button 4307 displayed in a single-frame format indicates that the item is low in importance of setup. Yet another feature is that the menu explicitly indicates an item currently being set up by the user. A button 4308, for example, is shaded for distinction from the buttons 4306, 4307. Explicitly indicating the current setup item in this way offers an advantage in that the user can readily confirm the number of remaining setup items.

In the present example, an optional parameter setting step 4309 is added to the sequence described using FIG. 43. Parameters that can be set up as options in the optional parameter setting step 4309 are, for example, function parameters on contamination size measurement, and classification parameters on contamination and defects.

The detailed setup parameter list 4302 is a window for setting up details of each parameter item. In order to enter or select an item, the item may have a keyboard input field as with an input box 4310, or may be of an icon-based input item selection scheme using with input icons 4311, for example. The input icons 4311 are an example of icons displayed for three input items such that a press of either icon displays another window to allow further detailed parameter setup. Additionally, a necessary item may be selected, as with an input checkbox 4312.

The settings display change button 4303 changes or customizes a display item. For example, when there is an item that the user always needs to set up for each inspection operation or when the user needs to set up more items, the user can conduct changes by using the button 4303 to customize the display into a more easily usable one for enhanced inspection parameter setup efficiency. The help information button 4304 outputs user assistance information when pressed by the user to obtain further detailed information on setup procedures or on parameter settings. Details of each setup item may be output as vocal guidance messages, or information on operations may be supplied as video images in a format such as MPEG. Yet another form of supplying the user help information may be such that the user can talk with a manufacturer's designer of the defect inspection apparatus of the present invention on-line through a network or a telephone line.

As described above, according to the present invention, very small particle-like contamination (including microcontamination of about 0.1 µm or less in size), thin-film-like contamination, scratches, and other defects present on various inspection target substrates each having various regions can be inspected with high speed and high accuracy with a simple configuration.

According to the present invention, a highly efficient manufacturing line for substrates can be constructed with a simple configuration by using the above-described apparatus as an in-line monitor with a low cost.

The invention may be embodied in other specific forms without departing from the spirit or essential characteristics thereof. The present embodiment is therefore to be considered in all respects as illustrative and not restrictive, the scope of the invention being indicated by the appended claims, rather than by the foregoing description, and all changes that come within the meaning and range of equivalency of the claims are therefore intended to be embraced therein.

What is claimed is:

1. A defect inspection apparatus comprising:
    an irradiation optical system that focuses a beam flux emitted from a laser light source and formed into a slit-shaped beam by fluxes of light that are substantially parallel in a longitudinal direction, from a direction having a required inclination with respect to a surface of a substrate to be inspected, so as to irradiate the beam flux onto the surface of the substrate to be inspected;
    a detection optical system that detects light from the substrate that has been irradiated with the slit-shaped beam; and
    a signal processor that processes a signal output from the detection optical system;
    wherein the irradiation optical system includes a cylindrical lens for focusing the beam flux that has been emitted from the laser light source onto the substrate to be inspected, as the slit-shaped beam;
    wherein the cylindrical lens is disposed so as to obtain a distance between an incidence surface or emitting surface thereof and the slit-shaped beam upon the substrate to be inspected to be equal to a focal distance of the cylindrical lens; and
    wherein the cylindrical lens is set at an inclination angle with respect to an optical axis of the beam flux emitted from the laser light source.

2. The defect inspection apparatus according to claim 1, wherein the irradiation optical system further includes an inclined mirror which is configured so as to allow the slit-shaped beam to be switched for irradiation at a high angle of inclination and for irradiation at a low angle of inclination.

3. The defect inspection apparatus according to claim 1, wherein the irradiation optical system includes an optical path switching unit which switches an optical path emitted from the laser light source to a first optical path or a second optical path.

4. The defect inspection apparatus according to claim 1, wherein, in the detection optical system, a spatial filter that light-shields an interference pattern formed from an iterative circuit pattern present on the substrate is disposed at a position conjugate to a pupil of an objective lens.

5. The defect inspection apparatus according to claim 1, wherein:
    in the irradiation optical system, the beam flux emitted from the light source is guided to a first optical path, a second optical path and a third optical path after being guided to a principal optical path; and
    a luminous quantity adjusting filter is disposed in the principal optical path for adjusting the amount of light.

6. The defect inspection apparatus according to claim 1, wherein:
    in the irradiation optical system, the beam flux emitted from the laser source is guided to a first optical path, a second optical path and a third optical path after being guided to a principal optical path;
    a polarizing plate is disposed in the principal optical path for conducting polarization control; and
    the detection optical system further includes an analyzer for controlling and detecting polarization.

7. The defect inspection apparatus according to claim 1, wherein the light source is configured so as to emit UV or DUV laser light.

8. The defect inspection apparatus according to claim 1, wherein the detection optical system is configured so as to make a detection imaging magnification variable.

9. A defect inspection method, comprising:

an irradiation step of focusing a beam flux emitted from a light source and formed into a slit-shaped beam by fluxes of light that are substantially parallel in a longitudinal direction, from a direction having a required inclination with respect to a surface of a substrate to be inspected, so as to irradiate the beam flux onto the surface of the substrate to be inspected;

a detection step of detecting light from the substrate that has been irradiated with the slit-shaped beam; and a signal processing step of processing a signal obtained from the detection of light at the detection step;

wherein, in the irradiation step, the beam flux is focused onto the substrate to be inspected, as the slit beam, by using a cylindrical lens which is set at an inclination angle with respect to an optical axis of the beam flux emitted from the light source and which is disposed so as to obtain a distance between an incidence surface or an emitting surface thereof and the slit-shaped beam upon the substrate to be inspected to be equal to a focal distance of the cylindrical lens.

10. The defect inspection apparatus according to claim 1, wherein the cylindrical lens has a curved surface and an opposite flat surface, the flat surface of the cylindrical lens being set at the inclination angle which is an oblige angle with respect to the optical axis of the beam flux emitted from the laser light source.

11. The defect inspection method according to claim 9, wherein the cylindrical has a curved surface and an opposite flat surface, the flat surface of the cylindrical lens being set at the inclination angle which is an oblique angle with respect to the optical axis of the beam flux emitted from the laser light source.

* * * * *